United States Patent
Torti et al.

(10) Patent No.: US 10,473,662 B2
(45) Date of Patent: Nov. 12, 2019

(54) DIAGNOSTIC AND PROGNOSTIC MARKERS FOR CANCER

(71) Applicant: Wake Forest University Health Sciences, Winston-Salem, NC (US)

(72) Inventors: Frank M. Torti, Avon, CT (US); Suzy V. Torti, Avon, CT (US); Lance Miller, Winston-Salem, CT (US)

(73) Assignee: WAKE FOREST UNIVERSITY HEALTH SCIENCES, Winston Salem, NC (US)

( * ) Notice: Subject to any disclaimer, the term of this patent is extended or adjusted under 35 U.S.C. 154(b) by 0 days.

(21) Appl. No.: 15/272,396

(22) Filed: Sep. 21, 2016

(65) Prior Publication Data

US 2017/0082629 A1    Mar. 23, 2017

Related U.S. Application Data

(63) Continuation of application No. 13/571,854, filed on Aug. 10, 2012, now abandoned, which is a
(Continued)

(51) Int. Cl.
*C12Q 1/6886* (2018.01)
*G01N 33/50* (2006.01)
(Continued)

(52) U.S. Cl.
CPC ..... *G01N 33/57484* (2013.01); *C12Q 1/6886* (2013.01); *G01N 33/57415* (2013.01);
(Continued)

(58) Field of Classification Search
CPC ....... G01N 33/57484; G01N 33/57434; G01N 33/57415; G01N 2800/54; C12Q 1/6886; C12Q 2600/158; C12Q 2600/118
See application file for complete search history.

(56) References Cited

U.S. PATENT DOCUMENTS

2006/0286565 A1   12/2006   Baker et al.
2007/0054271 A1*   3/2007   Polyak .................. C07K 14/47
                                                              435/6.14
(Continued)

FOREIGN PATENT DOCUMENTS

WO    2008/046182    4/2008
WO    2008/077165    7/2008
(Continued)

OTHER PUBLICATIONS

Kijima, H. et al., "Expression of hepcidin mRNA is uniformly suppressed in hepatocellular carcinoma", BMC Center, 9: 167 (2008.
(Continued)

*Primary Examiner* — Jeremy C Flinders
(74) *Attorney, Agent, or Firm* — Robert C. Netter, Jr.; Dann, Dorfman, Herrell & Skillman

(57) ABSTRACT

Compositions and methods useful for diagnosis and prognosis of cancer are provided. More particularly, methods for detecting breast or prostate cancer protein or nucleic acid biomarkers consisting of iron homeostasis biomarkers in a biological sample obtained from a subject are provided.

8 Claims, 34 Drawing Sheets

Specification includes a Sequence Listing.

Related U.S. Application Data continuation-in-part of application No. 13/500,957, filed as application No. PCT/US2010/052072 on Oct. 8, 2010, now abandoned.

(60) Provisional application No. 61/249,912, filed on Oct. 8, 2009, provisional application No. 61/351,767, filed on Jun. 4, 2010, provisional application No. 61/370,579, filed on Aug. 4, 2010, provisional application No. 61/522,018, filed on Aug. 10, 2011.

(51) Int. Cl.
*G01N 33/574* (2006.01)
*C40B 30/06* (2006.01)

(52) U.S. Cl.
CPC . *G01N 33/57434* (2013.01); *C12Q 2600/118* (2013.01); *C12Q 2600/158* (2013.01); *G01N 33/5011* (2013.01); *G01N 33/57449* (2013.01); *G01N 2333/575* (2013.01); *G01N 2333/705* (2013.01); *G01N 2800/54* (2013.01)

(56) References Cited

U.S. PATENT DOCUMENTS

| | | | |
|---|---|---|---|
| 2008/0064055 A1 | 3/2008 | Bryant et al. | |
| 2008/0261891 A1 | 10/2008 | Weimer | |
| 2008/0267872 A1 | 10/2008 | Raitano et al. | |

FOREIGN PATENT DOCUMENTS

| | | |
|---|---|---|
| WO | 2008/079877 | 7/2008 |
| WO | 2009/100029 | 8/2009 |
| WO | 2010/065940 | 6/2010 |

OTHER PUBLICATIONS

Liu, K.B. et al., "Regulation of hepcidin and ferroportin expression by lipopolysaccharide in splenic macrophages", Blood Cells Mol. Dis., 35(1): 47-56 (2005).

Pinnix, Z.K. et al., "Ferroportin and iron regulation in breast cancer progression and prognosis", Sci. Transl. Med., 2 (43): 43ra56 (2010).

Brooks, M.J. et al., "Modulation of iron transport proteins in human colorectal carcinogensis", Gut, 55(10): 1449-1460 (2006).

Huang, X., "Iron overload and its association with cancer risk in humans: evidence for iron as a carcinogenic metal", Mutat. Res., 533(1-2): 153-71 (2003).

Vecchi, M. et al., "Breast cancer metastases are molecularly distinct from their primary tumors", Oncogene, 27(15); 2148-58 (2008) (Supplemental Information & Supplemental Table 2).

Vecchi, M. et al., "Breast cancer metastases are molecularly distinct from their primary tumors", Oncogene, 27(15); 2148-58 (2008) (Supplemental Information 1-14).

Vecchi, M. et al., "Breast cancer metastases are molecularly distinct from their primary tumors", Oncogene, 27(15); 2148-58 (2008) (Supplemental Information 1-57).

Recalcati, S. et al., "Differential regulation of iron hemeostasis during human macrophage polarized activation", Eur. J. Immunol., 40(3): 824-35 (2010).

Toet, H. et al., "Autoantibodies to iron-binding proteins in pigs infested with Sarcoptes scabeie", Veterinary Parasitology, 205: 263-270 (2014).

Affymetrix 2007, "GeneChip Human Genome U133 Arrays Data Sheet".

\* cited by examiner

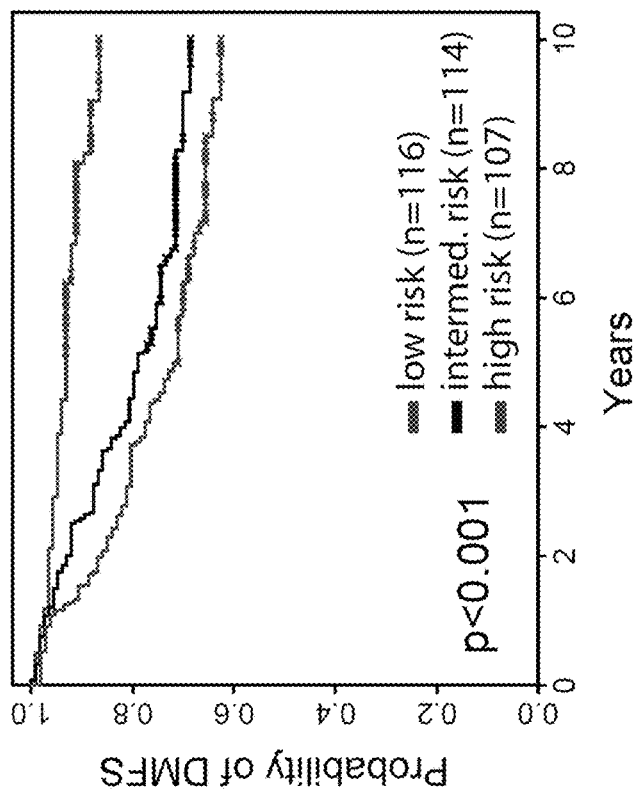
FIG. 22A Training Cohort (n=337)
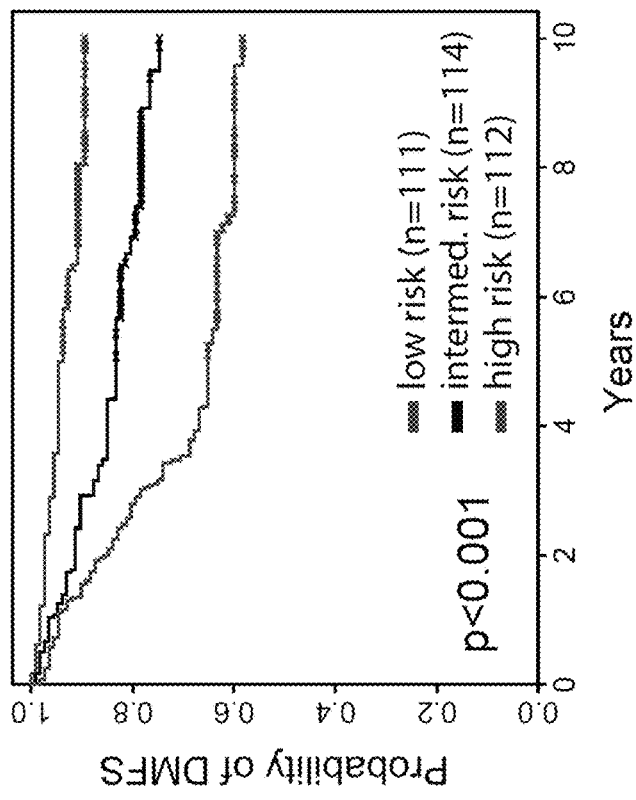
FIG. 22B Test Cohort (n=337)

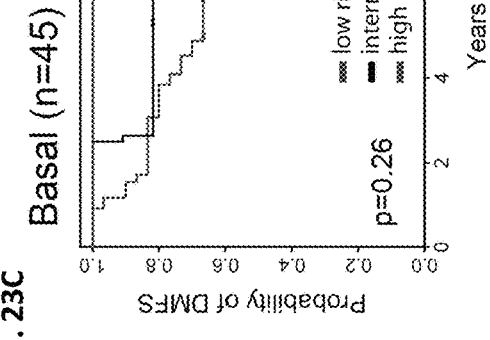
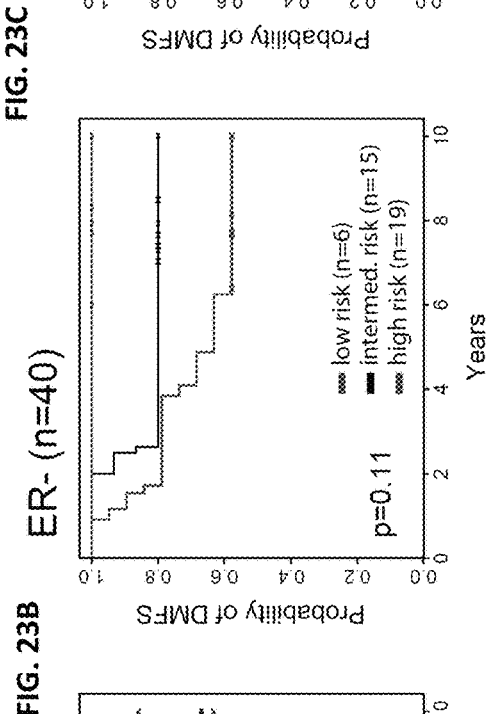
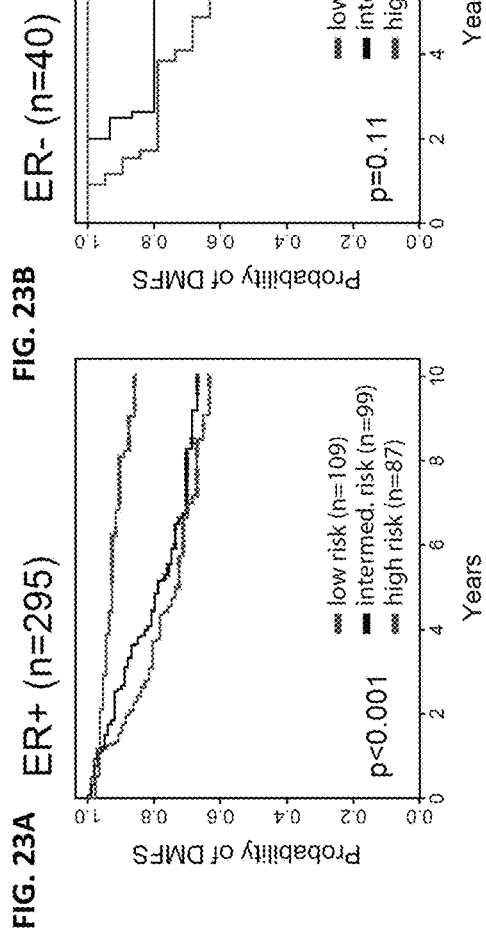
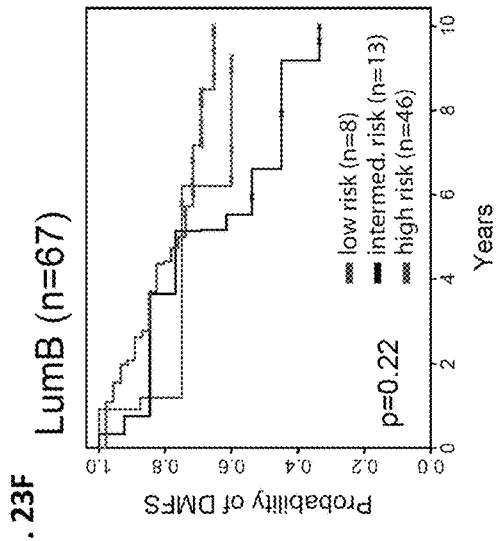
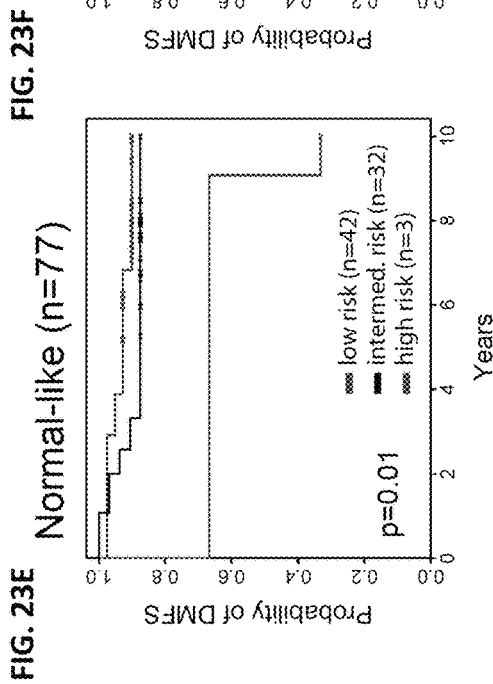
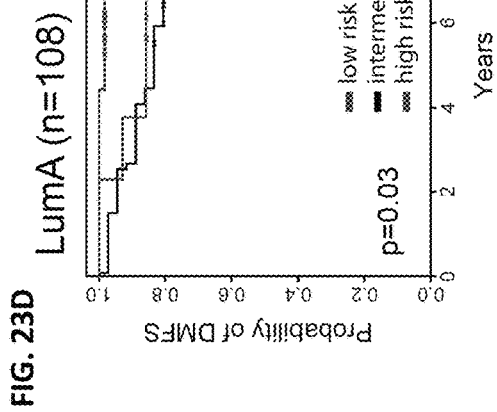
FIG. 23A
FIG. 23B
FIG. 23C
FIG. 23D
FIG. 23E
FIG. 23F

FIG. 26A
FIG. 26B
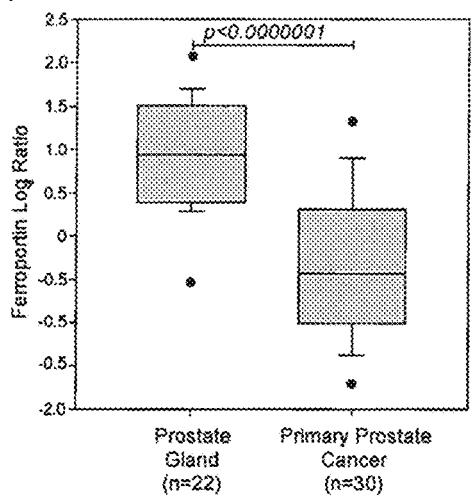
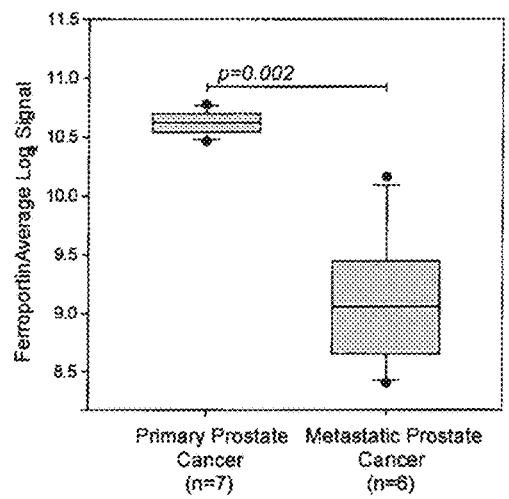
Ferroportin is down-regulated in primary and metastatic prostate cancer. Shown are box plots of log-transformed Ferroportin mRNA expression levels in 2 prostate cancer gene profiling studies: (A) Tomlins, et. al., and (B) Varambally, et. al. T test p-values that reflect differential expression between sample groups are shown.

DIAGNOSTIC AND PROGNOSTIC MARKERS FOR CANCER

This application is a continuation of U.S. patent application Ser. No. 13/571,854 filed Aug. 10, 2012 which claims benefit of US Provisional application 61/522,018 filed Aug. 10, 2011. U.S. patent application Ser. No. 13/571,5854 is a continuation in part of U.S. patent application Ser. No. 13/500,957 filed Aug. 22, 2012, which is a § 371 of PCT/US10/52072 filed Oct. 8, 2010 which claims priority to U.S. Provisional Applications 61/249,912, 61/351,767 and 61/370,579 filed Oct. 8, 2009, Jun. 4, 2010 and August 2010, respectively, each of the aforementioned applications being incorporated herein by reference.

Pursuant to 35 U.S.C. § 202(c) it is acknowledged that the U.S. Government has rights in the invention described, which was made with funds from the National Institutes of Health, Grant Numbers R37DK42412, and RO1 DK071892.

FIELD OF THE INVENTION

The present invention relates to the fields of medicine and oncology. More specifically, the invention provides compositions and methods useful for the prognosis, diagnosis and treatment of cancer, particularly breast, prostate and ovarian cancer.

BACKGROUND OF THE INVENTION

Several publications and patent documents are cited throughout the specification in order to describe the state of the art to which this invention pertains. Each of these citations is incorporated herein by reference as though set forth in full.

Ferroportin (ferroportin 1, also termed Ireg1, MTP1, SLC40A1) is a cell surface transmembrane protein and is the only known export protein for non-heme iron (1-3). Ferroportin is expressed at high levels on duodenal enterocytes, placenta, hepatocytes, and macrophages (1-3), and is an essential component of systemic iron homeostasis (4). Ferroportin is regulated by at least three mechanisms: transcriptional regulation, which controls levels (5) and splice variants (6) of the mRNA; translational regulation, which regulates ferroportin through an iron regulatory element in the 5' UTR of ferroportin mRNA (7); and organismal iron status, which regulates ferroportin mediated iron efflux through a direct interaction of ferroportin with the peptide hormone hepcidin (8). Hepcidin is secreted by the liver and binds to a specific extracellular loop domain on ferroportin (9). This results in phosphorylation (10) of ferroportin on the cell surface, which in turn leads to internalization and proteosome-mediated degradation of ferroportin (8).

Ferroportin has not been extensively studied in cancer (11, 12), and only limited examination has been made of ferroportin outside the tissues generally thought to be important in systemic iron homeostasis, such as the intestine, the liver, the bone marrow, and the reticulo-endothelial system (13).

SUMMARY OF THE INVENTION

In accordance with the present invention, a method of predicting the likelihood of long-term survival of a cancer patient without the recurrence of cancer, following surgical removal of the primary tumor or any other procedure suitable from treating or removing the cancer, is provided. An exemplary method entails obtaining a biological sample from a patient, determining the expression levels of at least two iron homeostasis associated (IHA) markers provided in Tables I or II in the patient; and comparing the expression levels of the at least two IHA markers in the patient sample to predetermined expression levels of IHA markers observed in a cohort of cancer patients having a known clinical outcome of recurrent or non recurrent disease, thereby determining said patients risk for recurrence of cancer. In one embodiment, the predetermined expression levels are the mean expression levels observed across the entire patient cohort.

In a preferred embodiment the cancer is breast, ovarian or prostate cancer, the at least two markers are ferroportin and hepcidin, and high ferroportin levels in the presence of low hepcidin levels relative to said predetermined expression levels are indicative of a lowered risk of recurrent disease.

In yet another embodiment, the cancer is breast cancer, the at least two markers are DcytB and TFRC, and high DcytB levels in the presence of low TFRC levels relative to said predetermined expression levels are indicative of a lowered risk of recurrent disease. In another or additive approach the two markers are HFE and TFRC, and high HFE levels in the presence of low TFRC levels are indicative of a lowered risk of recurrent disease. Embodiments of the invention include analyzing the expression levels of all 79 markers in Table II, analysis of the markers provided in Tables I and III or analysis of the subcombination of markers shown in Table IV. Analysis of the expression levels of the IRGS comprises a preferred embodiment of the invention.

In another aspect, the cancer is breast cancer and expression levels of six IHA makers are determined. In this approach, the markers are ferroportin, CyBRD1, STEAP1, STEAP2, ISCU and TFRC, and high expression levels of CyBRD1, STEAP1, STEAP2, ISCU in the presence of a low expression level for TFRC relative to the predetermined mean expression levels is associated with a decreased risk of recurrent disease.

The method optionally entails determining levels of additional iron homeostasis associated marker molecules selected from the group consisting of ferritin L protein, IREB2 protein, transferrin receptor protein 1, transferrin, TMPRSS6 and ferritin H. Markers include both IHA polypeptides, nucleic acids encoding the same and fragments thereof. Another embodiment of the method includes the step of determining at least one parameter selected from the group consisting of estrogen receptor (ER) status, her2-neu status, progesterone receptor status histological grade, tumor size, patient age, tumor stage and nodal status of the patient.

The method can also include creating a report summarizing the data obtained by the determination of said IHA marker expression levels. This report can also include a prediction of the likelihood of long term survival of said patient without the recurrence of breast cancer following surgical removal of the primary tumor or any other procedure suitable to remove the cancer. Finally, the report can include a recommendation for a treatment modality of said patient. The method of the invention can be performed at any time following a diagnosis for cancer, e.g., when a patient has been diagnosed with breast cancer is undergoing treatment for breast cancer, when the patient has completed treatment for cancer or when the patient diagnosed with breast cancer is in remission. The biological sample includes without limitation, formalin fixed paraffin embedded tissue or cells, frozen tissue, blood cells, breast cancer cells, ovarian cancer cells and prostate cancer cells. In a preferred embodiment, the sample is a biopsy sample.

In yet another aspect, the invention provides a kit for practicing the method described above. Such kits include reagents for detection of either marker proteins or polypeptides or marker encoding nucleic acids or fragments thereof. A kit for determining ferroportin and hepcidin protein levels includes for example, antibodies immunologically specific for ferroportin and hepcidin or fragments thereof, means for detecting immune complex formation between said ferroportin, hepcidin and said antibodies and instructional materials comprising ranges of expression levels associated with aggressive metastatic breast cancer and ranges of expression levels associated with non-aggressive non metastatic breast cancer. A kit for determining ferroportin and hepcidin nucleic acid levels in said sample, includes for example, nucleic acids which specifically hybridize to ferroportin and hepcidin encoding nucleic acids, means for detecting hybridization between said ferroportin, hepcidin nucleic acids and instructional materials comprising ranges of expression levels associated with aggressive metastatic recurrent breast cancer and ranges of expression levels associated with non-aggressive non metastatic non recurrent breast cancer.

Finally, the invention also includes a method for identifying agents which modulate iron homeostasis. In one embodiment, the method entails contacting a cell comprising at least one iron homeostasis related protein; and assessing the effect of said agent on modulation of iron homeostasis relative to untreated cells. Such proteins include without limitation, ferroportin, hepcidin, ferritin L protein, IREB2 protein, transferrin receptor protein 1, transferrin, TMPRSS6 and ferritin H. Modulatory effects assessed by the method include, without limitation, iron transport, iron metabolism and cellular iron levels.

BRIEF DESCRIPTION OF THE DRAWINGS

(FIG. 1A) Levels of ferroportin in normal and malignant breast cells. 50 μg of protein from each cell type was analyzed for ferroportin expression by Western blotting. Equal loading was confirmed by probing with antibody to GAPDH and by staining with Ponceau S. (FIG. 1B) Labile iron pool in normal and malignant breast cells. Cells were loaded with calcein using acetomethoxyl-calcein, and fluorescence was measured before and after addition of iron chelator (SIH). Labile iron was calculated based on the fractional increase in fluorescence and the intracellular calcein concentration as described in Materials and Methods. Graphs show mean and standard deviation of triplicate determinations.

(FIG. 3A) Western blot of pro-hepcidin protein in normal and malignant breast cells. (Pro-hepcidin was detected in all cells on prolonged exposure [not shown]). (FIG. 3B) Hepcidin treatment increases the labile iron pool. HME cells were treated with 700 nM hepcidin or vehicle control and the labile iron pool measured as described in Materials and Methods. (FIG. 3C) Hepcidin treatment increases levels of ferritin protein. HME cells were treated with vehicle, 300 nM or 700 nM hepcidin for 6 hours and ferritin H assessed by Western blotting. GAPDH was used as a loading control. (FIG. 3D) Ferroportin is degraded in normal mammary epithelial (HME) cells treated with hepcidin. Cells were incubated with vehicle, 300 or 700 nM hepcidin for 6 hours and ferroportin measured by Western blotting. GAPDH was used as a loading control.

(FIG. 4A) Ferroportin variant I mRNA was quantified in primary human mammary epithelial cells and breast cell lines by real-time RT-PCR as described in Materials and Methods. (FIG. 4B) Ferroportin mRNA splice variants were assessed by non quantitative RT-PCR in the same cell lines. All splice variants were observed in K562 cells; in contrast, none were observed in breast cells. Variant IIB corresponds to the IRE-negative FPN IB previously described (6). GAPDH was used as a positive control.

MDA-MB-231-luc breast cancer cells were transfected with an expression vector for ferroportin or control empty vector. Two independent ferroportin clones were isolated (FPN7 and FPN13). $2 \times 10^6$ control or ferroportin-expressing cells were suspended in matrigel and injected orthotopically into the mammary fat pad of nu/nu mice. Tumor growth was monitored in a subset of mice by bioluminescent imaging. Tumors were also weighed at the conclusion of the experiment. (FIG. 5A) Final tumor weights (n=10, 8, 13 for controls, FPN7, and FPN13, respectively); *p=0.013; **p=0.029 difference from controls, Student's t-test. (FIG. 5B) Representative bioluminescent images of individual mice within each group; (FIG. 5C) Quantified bioluminescence in control and FPN tumors. Means and standard deviations are plotted. p-value represents test for the time by group interaction indicating a highly significant difference among the 3 groups.

Figure 1A:
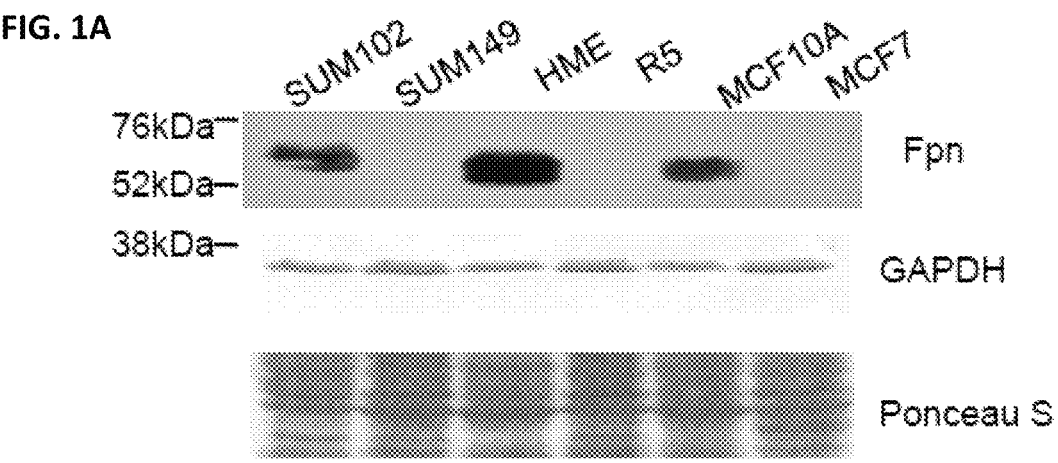
FIG. 1A-FIG. 1B. A decrease in ferroportin in breast cancer cell lines is associated with an increase in the labile iron pool.

Expression of hepcidin was analyzed in normal and malignant breast cells by non-quantitative RT PCR as described in Materials and Methods. K562 erythroleukemia cells are a positive control; these cells exhibit levels of hepcidin mRNA that are roughly comparable to those of HepG2 cells (data not shown).

FIG. 7A-FIG. 7F. Ferroportin is decreased in human breast cancer tissue. (FIG. 7A-FIG. 7C) Ferroportin staining in tissue. Tissue was isolated from a patient diagnosed with invasive ductal carcinoma. Within this single tissue, normal epithelium, ductal carcinoma in situ and invasive breast cancer cells were observed. The tissue was stained with antibody to ferroportin-1. Original magnification ×220. (FIG. 7A) Normal tissue exhibits strong staining of ferroportin (FIG. 7B) Ductal carcinoma in situ exhibits an intermediate staining intensity; (FIG. 7C) invasive breast cancer exhibits lowest staining intensity relative to normal epithelium and ductal carcinoma in situ. (FIG. 7D-FIG. 7F) Ferroportin staining of breast tissue microarrays. Breast tissue microarrays were stained with antibody to ferroportin and intensity of staining scored as described hereinbelow. Range of scores was 0-2 (low to high). (FIG. 7D) Mean and standard deviation of intensity score of normal breast tissue versus cancer tissue; (FIG. 7E) Percent of cells with a staining intensity of 2; (FIG. 7F) Percent of tissue specimens with a staining intensity of 1.

FIG. 8A-FIG. 8D. Relative levels of ferroportin protein in MDA-MB-231 cells and transfectants and specific detection of ferroportin by Western blotting. (FIG. 8A) Levels of ferroportin protein were assessed by Western blotting in normal human mammary epithelial cells (HME) and MDA-MB-231 breast cancer cells; ferroportin protein is decreased in MDA-MB-231 cells relative to HME. *ns; non-specific band. (FIG. 8B) Levels of ferroportin protein in MDA-MB-231 cells stably transfected with a ferroportin expression vector were compared to HME cells by Western blotting. (FIG. 8C) Ferroportin protein was analyzed by Western blotting in normal and malignant breast cells in the presence and absence of 5 µg blocking peptide. (FIG. 8D) Hela cells were transiently transfected with a ferroportin expression vector or empty vector. 24 hours post-transfection, ferroportin protein was analyzed by Western blotting.

FIG. 9A-FIG. 9D. Ferroportin expression is correlated with clinical and molecular features of breast cancer. (FIG. 9A) Ferroportin expression in Sorlie-Perou molecular subtypes. Shown are box and whisker-plots of ferroportin gene expression as a function of molecular subtype in consecutive breast cancer patients from Uppsala Sweden (21). Of the 251 tumors in this cohort, 228 showed correlation of >0.1 with at least one subtype; the remaining 23 were classified as "no subtype" and were censored. Shaded rectangles represent interquartile range; line in the middle of each rectangle represents median value. Lines extending from the interquartile range mark the $5^{th}$ and 95th percentile values and the individual open circles represent values that are either above the 95th percentile or below the 5th percentile for each distribution. Molecular subtypes were assigned by Calza et al. (22). P-values are shown above bridges linking the subtypes. LumA=luminal A, LumB=luminal B, ERBB2+= ErbB2/HER2 neu-positive-like. (FIG. 9B) Ferroportin expression is correlated with histologic grade. Shown are box and whisker-plots of ferroportin gene expression as a function of histologic grade (1,2,3) in the Uppsala cohort. P-values (Student's t-test) are shown above bridges linking grade categories. (FIG. 9C) Ferroportin expression is correlated with breast tumor ER status. Shown are box and whisker-plots of ferroportin gene expression as a function ER status (+,−) in the Uppsala cohort. P-values (student's t-test) are shown above bridges linking grade categories. (FIG. 9D) Ferroportin expression is correlated with lymph node (LN) status. Shown are box and whisker-plots of ferroportin gene expression as a function LN status (+, −) in the Uppsala cohort. P-values (student's t-test) are shown above bridges linking grade categories.

Figure 10:
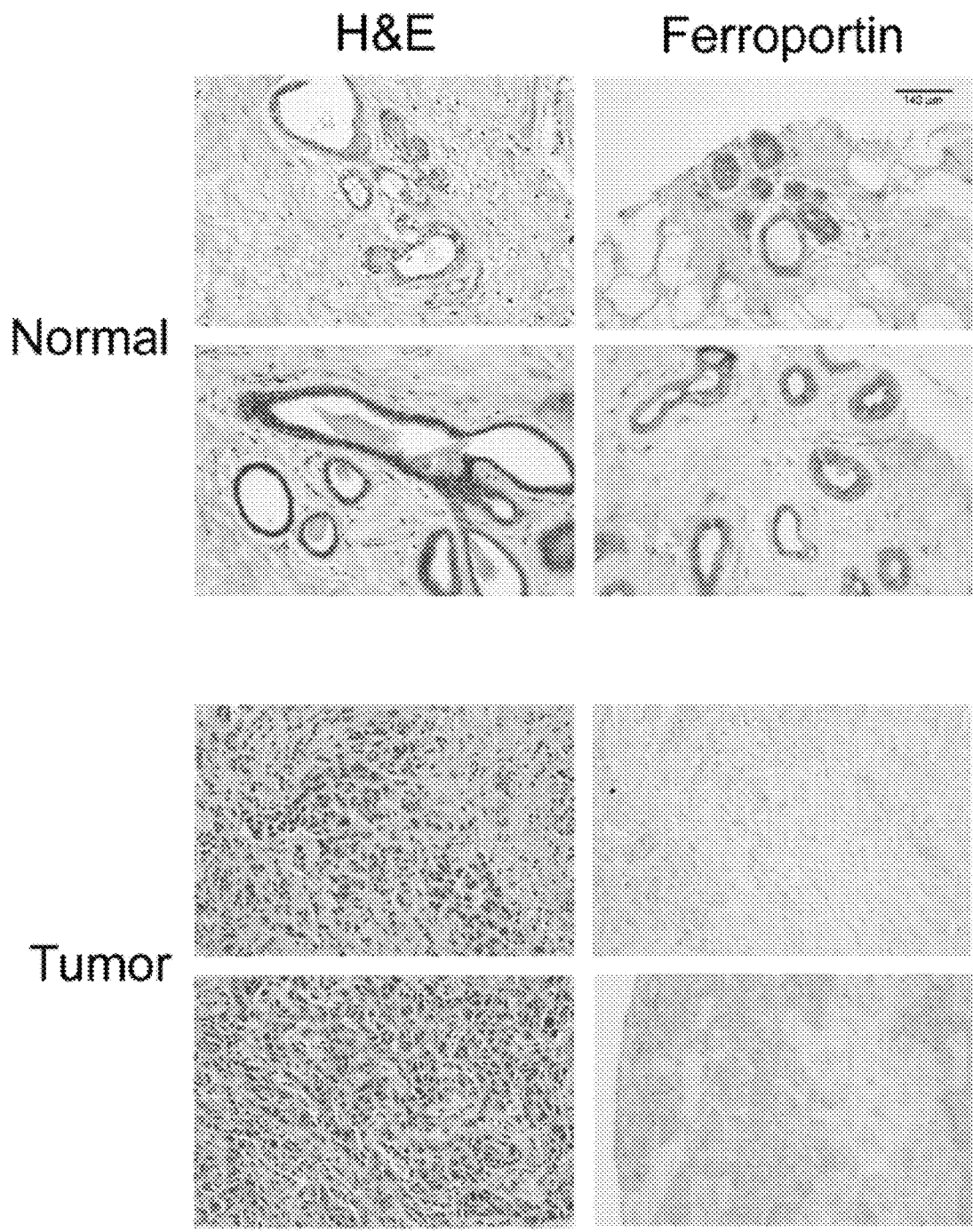
Figure 11A:
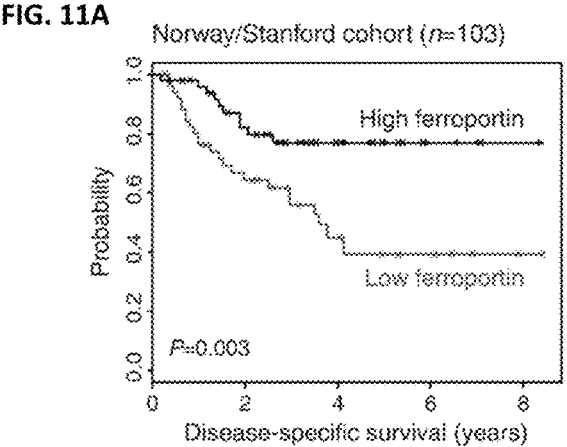
Figure 11B:
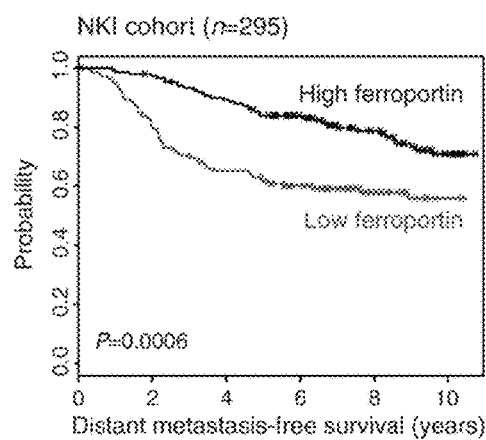
Figure 11C:
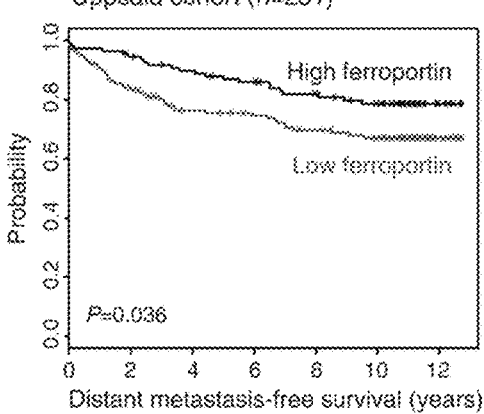
Figure 11D:
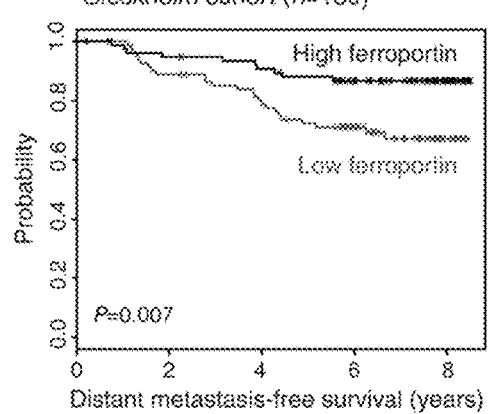

FIG. 10. Ferroportin protein is decreased in breast cancer. Two normal and two malignant breast specimens were examined for ferroportin expression by immune histochemical analysis. Original magnification ×72.

FIG. 11A-FIG. 11D. Ferroportin expression in primary breast tumors is prognostic of low risk of recurrence in multiple independent microarray datasets. Breast cancer patients were ranked according to ferroportin expression levels, and disease-specific survival or distant metastasis-free survival of patients with below-mean expression was compared to that of patients with above-mean expression by Kaplan-Meier (KM) analysis. KM plots are shown for (FIG. 11A) the Norway/Stanford cohort (23) (included were 103 tumors with reported expression values for ferroportin; data for 19 tumors was reported as "missing" in the original dataset and these were excluded from the analysis); (FIG. 11B) the Netherlands Cancer Institute (NKI) cohort (24); (FIG. 11C) The Uppsala cohort (25); and (FIG. 11D) the Stockholm cohort (21). Log rank tests were used to compare the survival curves between groups and generate the p-values for these comparisons.

Figure 12:
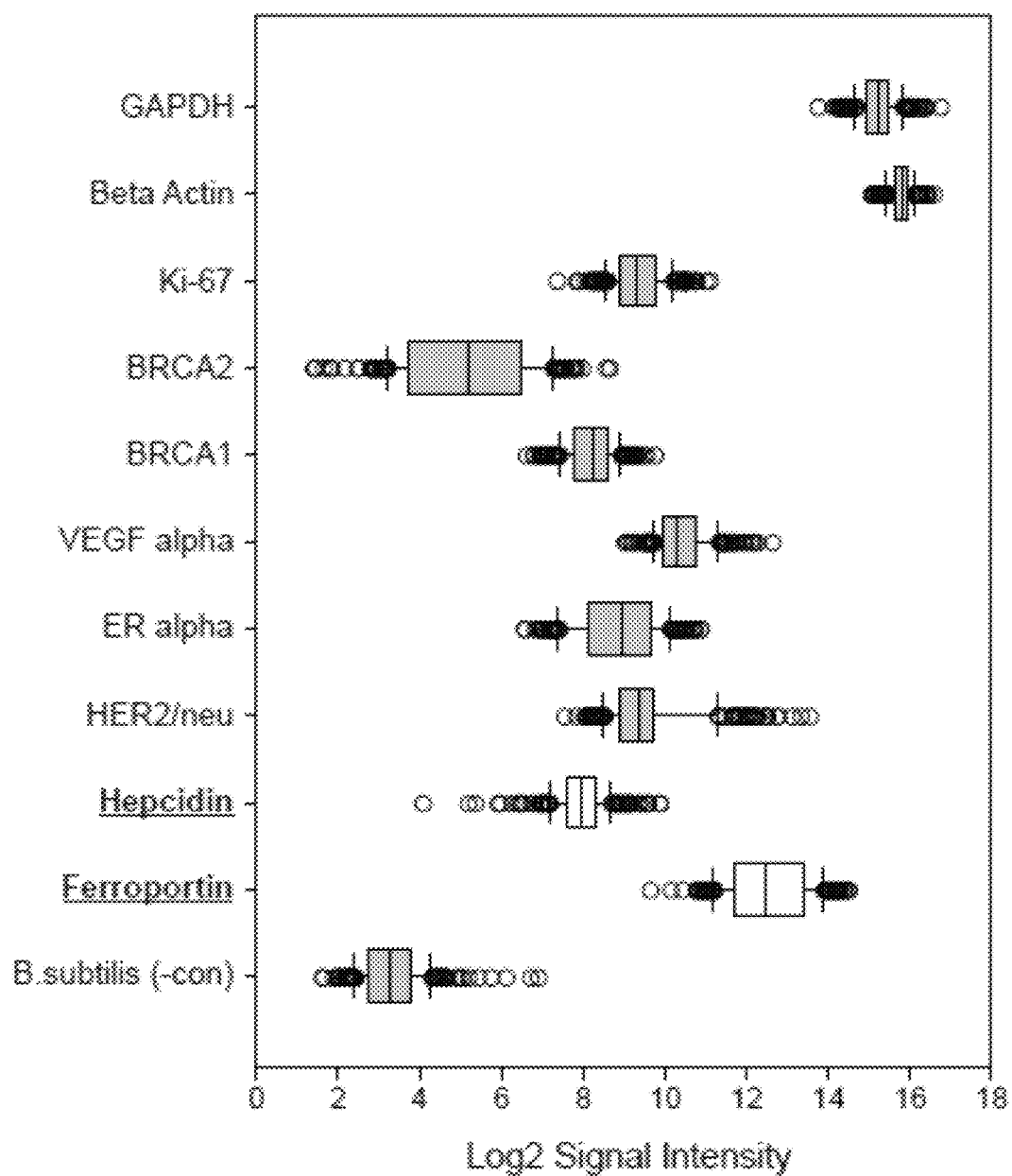

FIG. 12. Signal intensities of ferroportin and hepcidin relative to control genes and other breast cancer genes in the Uppsala cohort. Gene expression distributions from the Uppsala cohort dataset are shown. Rectangles represent interquartile range; mid-line represents median expression. Lines extending from the interquartile range mark the 5th and 95th percentiles of expression; open circles indicate cases with >$95^{th}$ percentile or <5th percentile expression. In cases where multiple probe sets map to the same gene, average expression intensities are plotted. Both ferroportin and hepcidin expression distributions (unshaded boxes) are significantly higher than that of the *B. subtilis* negative control, lower than housekeeping genes GAPDH and beta actin, and comparable to other genes important in breast cancer.

Figure 13A:
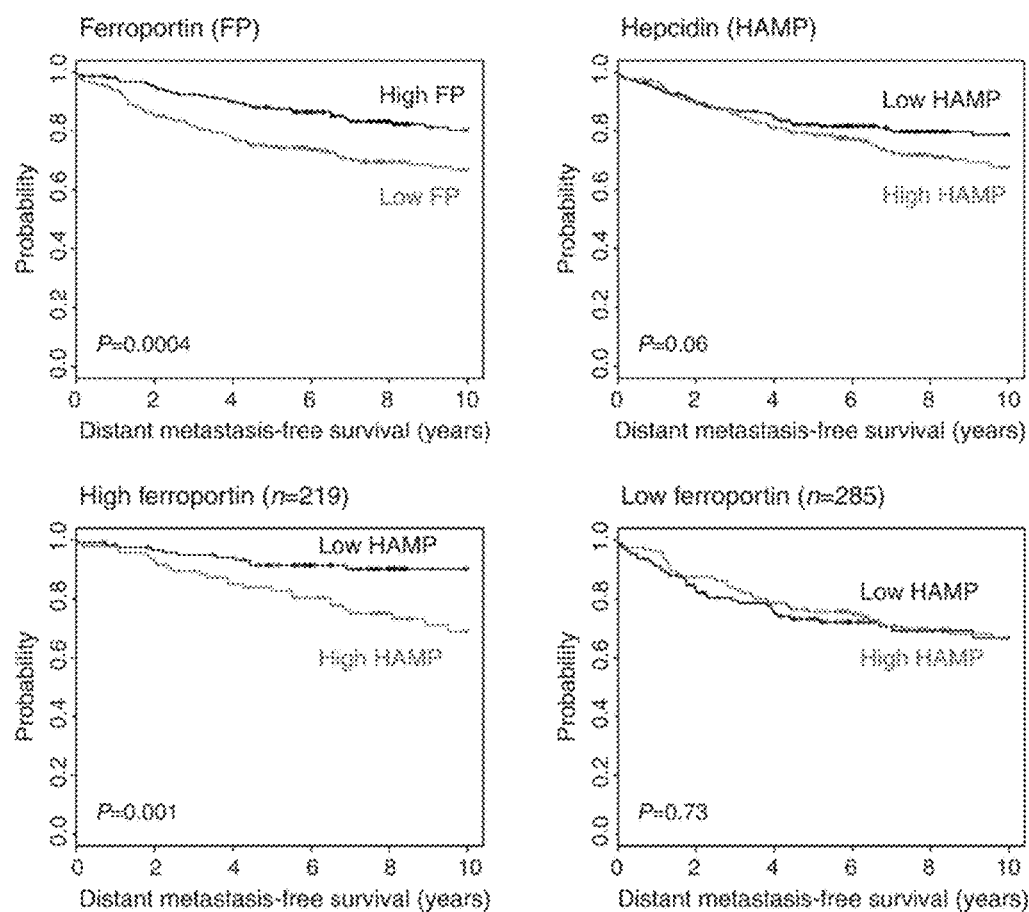
Figure 13B:
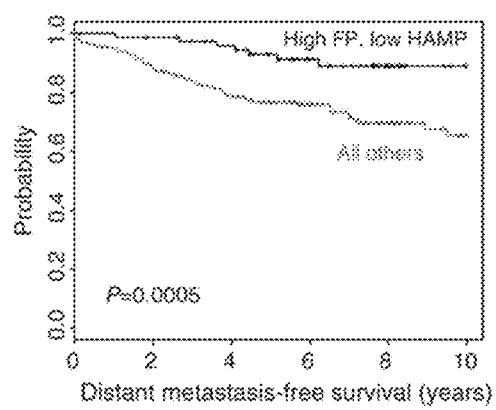

FIG. 13A-FIG. 13B. Ferroportin and hepcidin prognostic interactions. (FIG. 13A) Associations between distant metastasis-free survival and high/low ferroportin and hepcidin expression levels (based on mean partitioning) in a combined multi-institutional population-based cohort consisting of 504 breast cancer cases. Kaplan-Meier plots and log rank p values are shown for (1) ferroportin expression, (2) hepcidin expression, (3) high ferroportin dichotomized by low versus high hepcidin, and (4) low ferroportin dichotomized by low versus high hepcidin. (FIG. 13B) Prognostic value of high ferroportin-low hepcidin expression in a combined multi-institutional cohort of 518 ER+ breast cancer cases. The Kaplan-Meier plot compares the combined effects of ferroportin and low or high hepcidin expression on distant metastasis-free survival in patients treated with tamoxifen monotherapy.

Figure 14A:
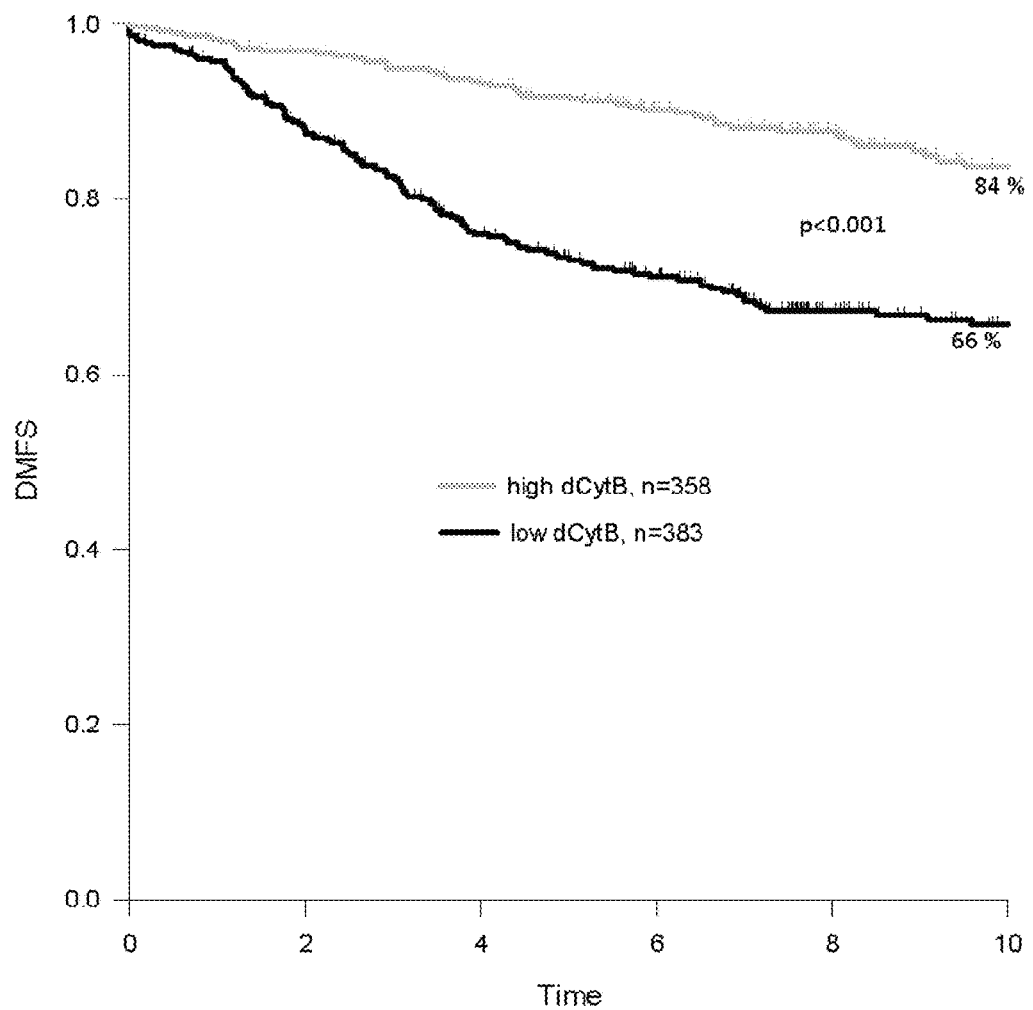
Figure 14B:
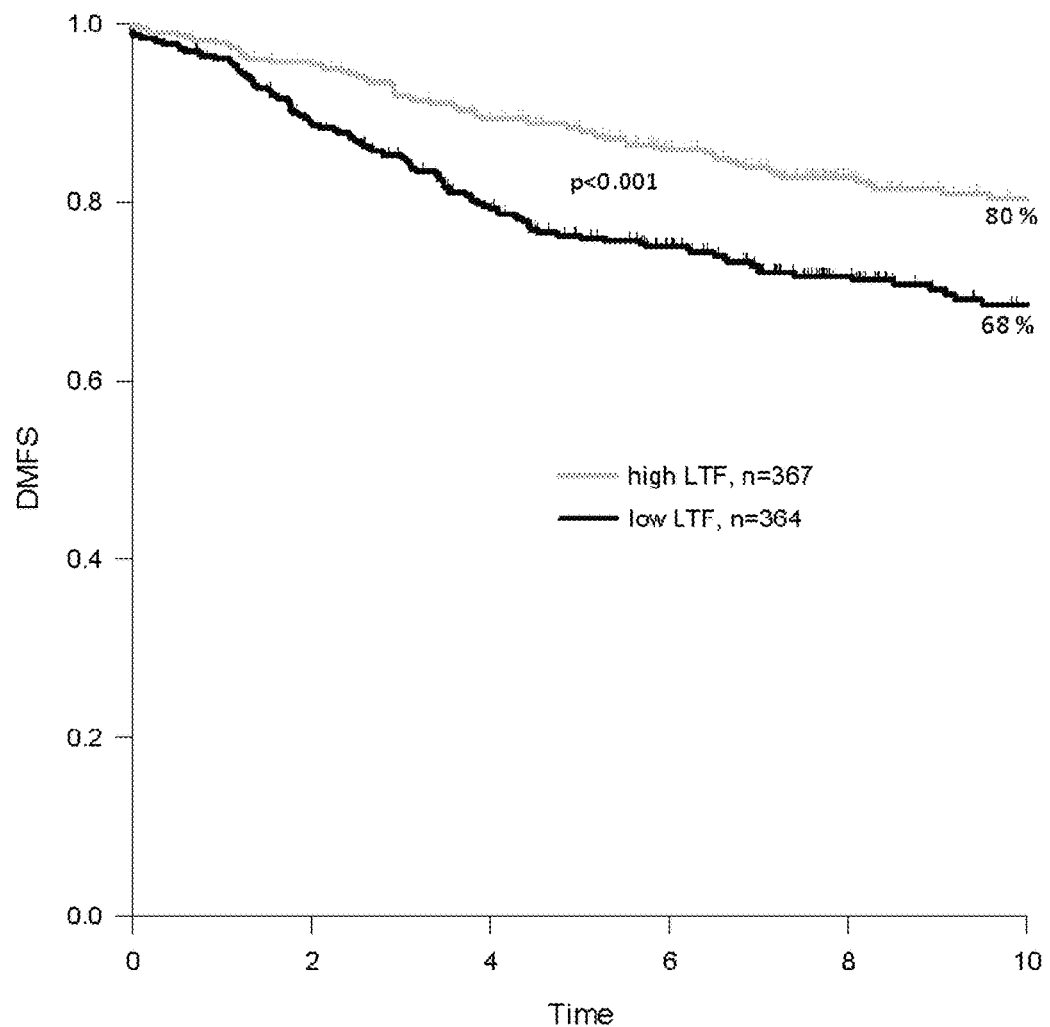
Figure 14C:
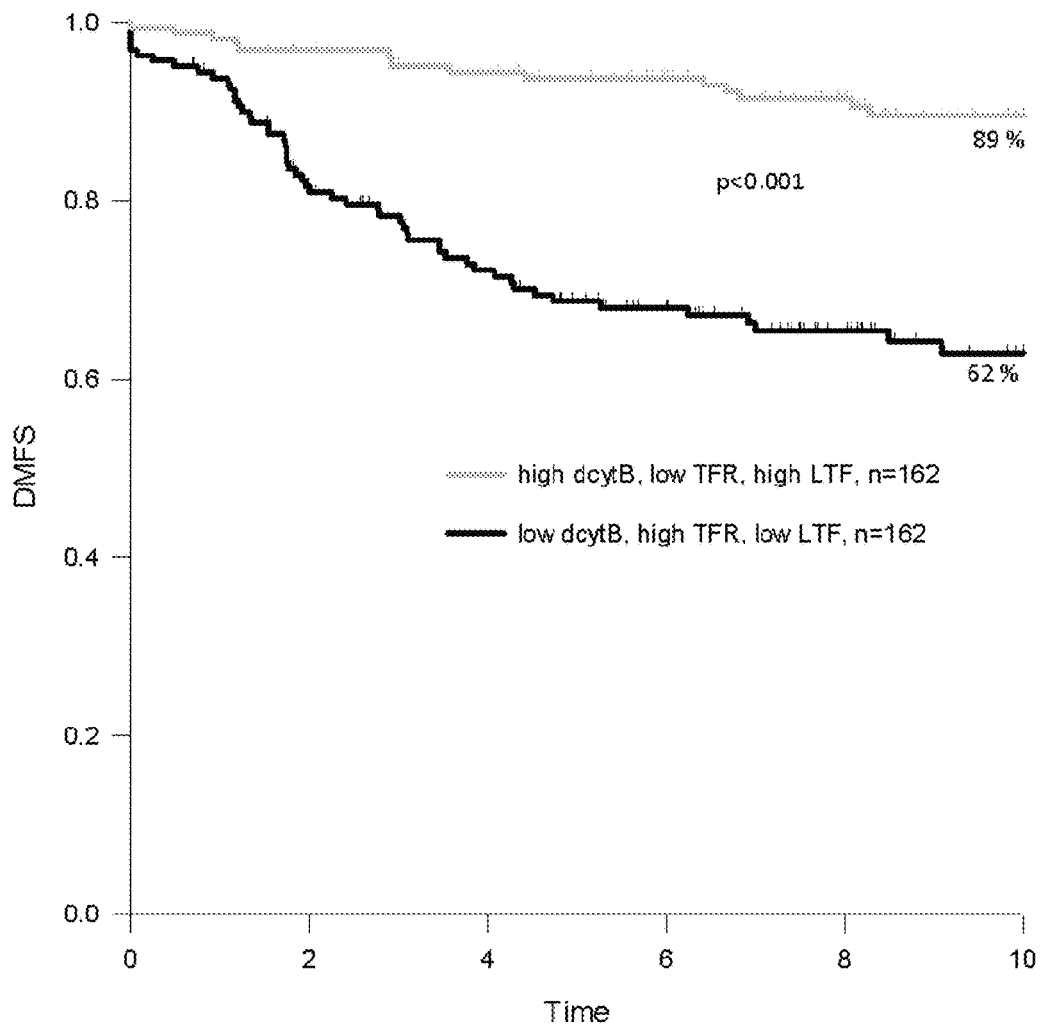
Figure 14D:
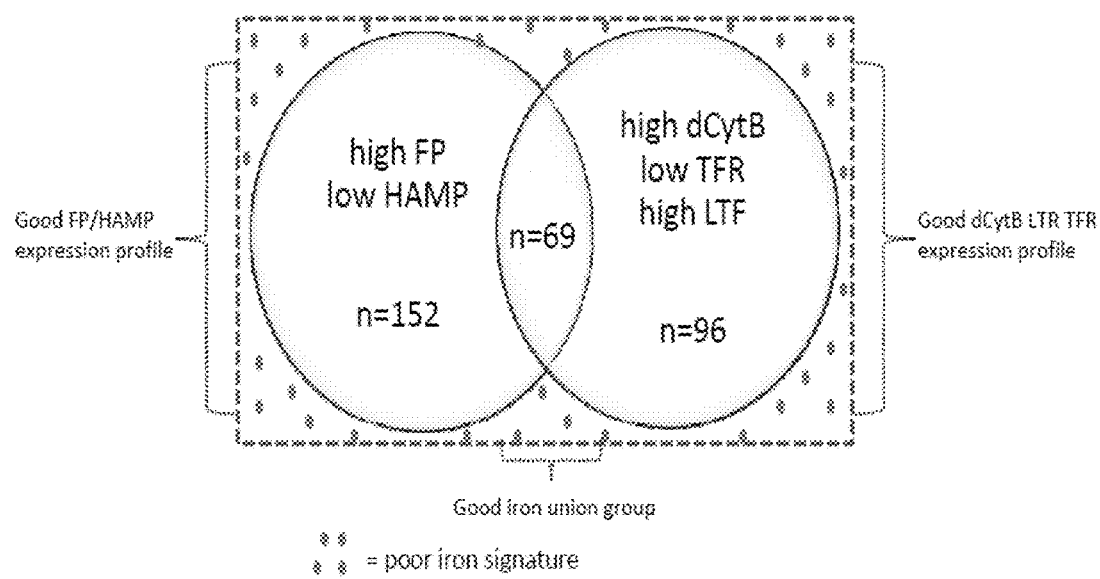
Figure 14E:
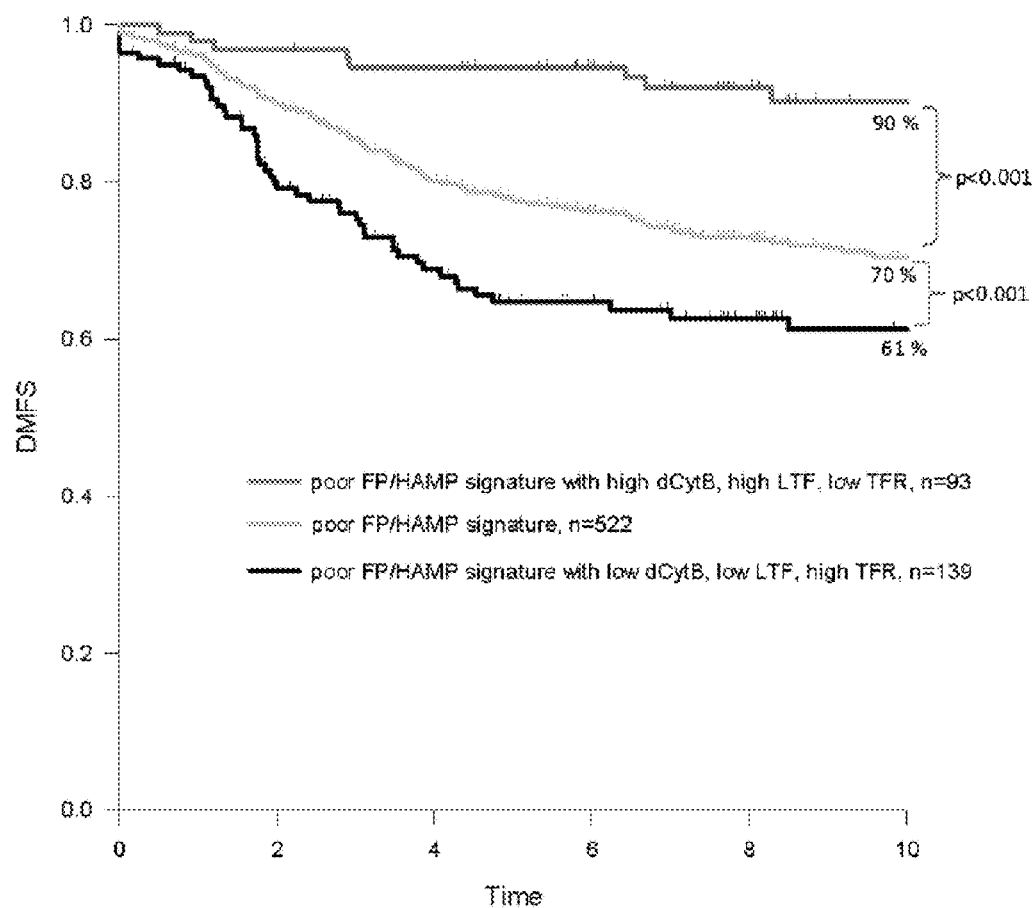

FIG. 14A-FIG. 14E. FIG. 14A provides a Kaplan-Meier survival curve of tumors divided by dCytB expression. FIG. 14B provides Kaplan-Meier survival curve of tumors divided by LTF expression. FIG. 14C provides a Kaplan-Meier survival curve of tumors divided by dCytB, LTF and TFR expression. For FIG. 14A-FIG. 14C: high=tumors with expression levels at or above the mean, low=tumors with expression levels below the mean. Figure FIG. 14D provides a diagram of iron gene expression groups. Good FP/HAMP expression profile=tumors expressing high FP and low HAMP. Good dCytB, LTF, TFR expression profile=tumors expressing high dCytB, high LTF, low TFR. Good iron union group=tumors expressing both high FP and low HAMP and high dCytB, high LTF and low TFR. Poor iron signature=all tumors that do not fall into the good iron expression groups. FIG. 14E provides Kaplan-Meier survival curves of tumors with poor FP/HAMP signature divided by dCytB, LTF and TFR expression. High=tumors with expression levels at or above the mean, low=tumors with expression levels below the mean.

Figure 15:
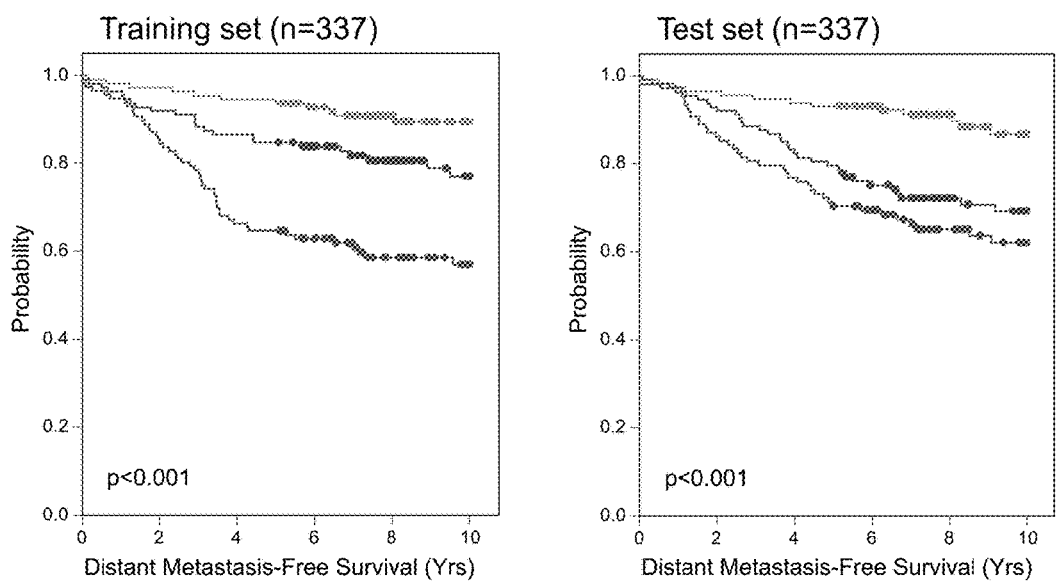

FIG. 15. Results of Kaplan-Meier analysis on different patient cohorts which reveals three distinct statistically significant low, intermediate and high risk survival curves using the genetic signatures described herein.

Figure 16:
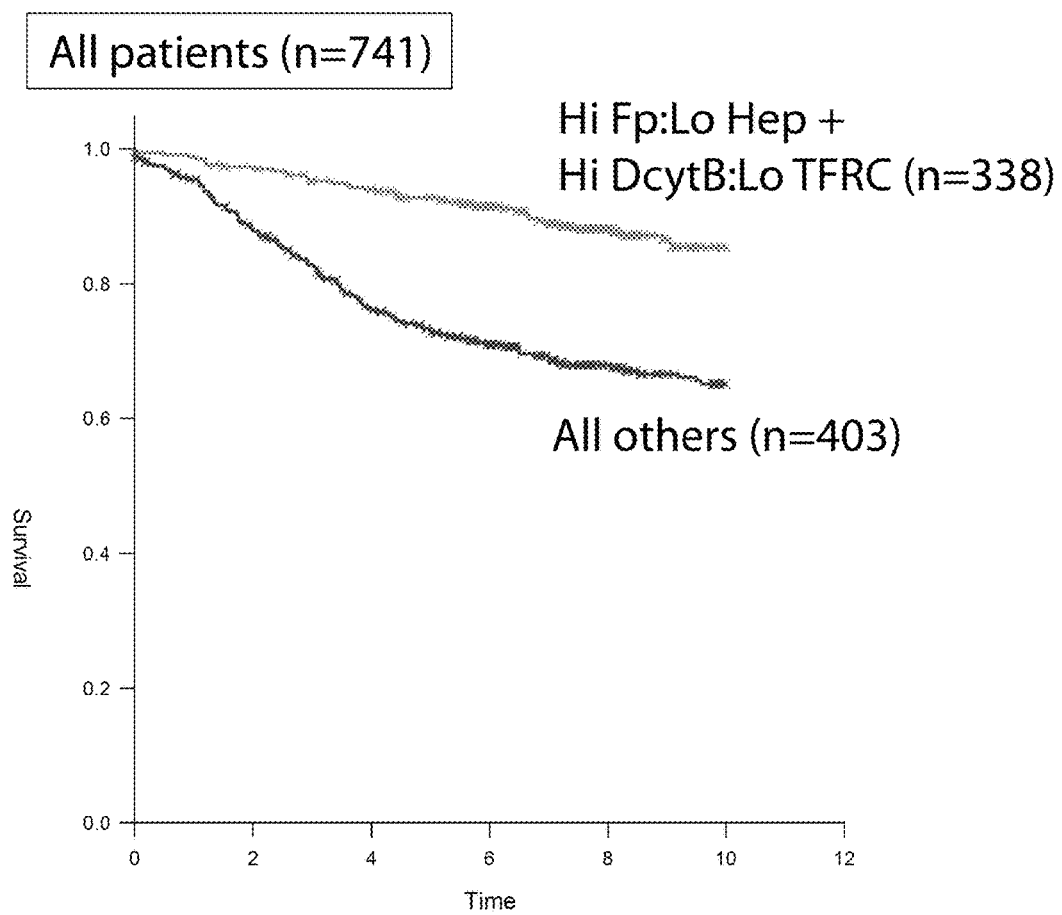

FIG. 16. Kaplan-Meier plot is shown for 741 patients divided into two groups: low risk group and high risk group. The low risk group (green survival curve) is defined as those patients whose tumors express 1) high Feroportin (Fp) and low Hepcidin (Hep), or 2) high DcytB (also known as CYBRD1) and low transferring receptor (TFRC) (n=338). The high risk group (red survival curve) is defined as patients with tumors whose gene expression patterns do not meet the low risk criteria (n=403).

Figure 17:
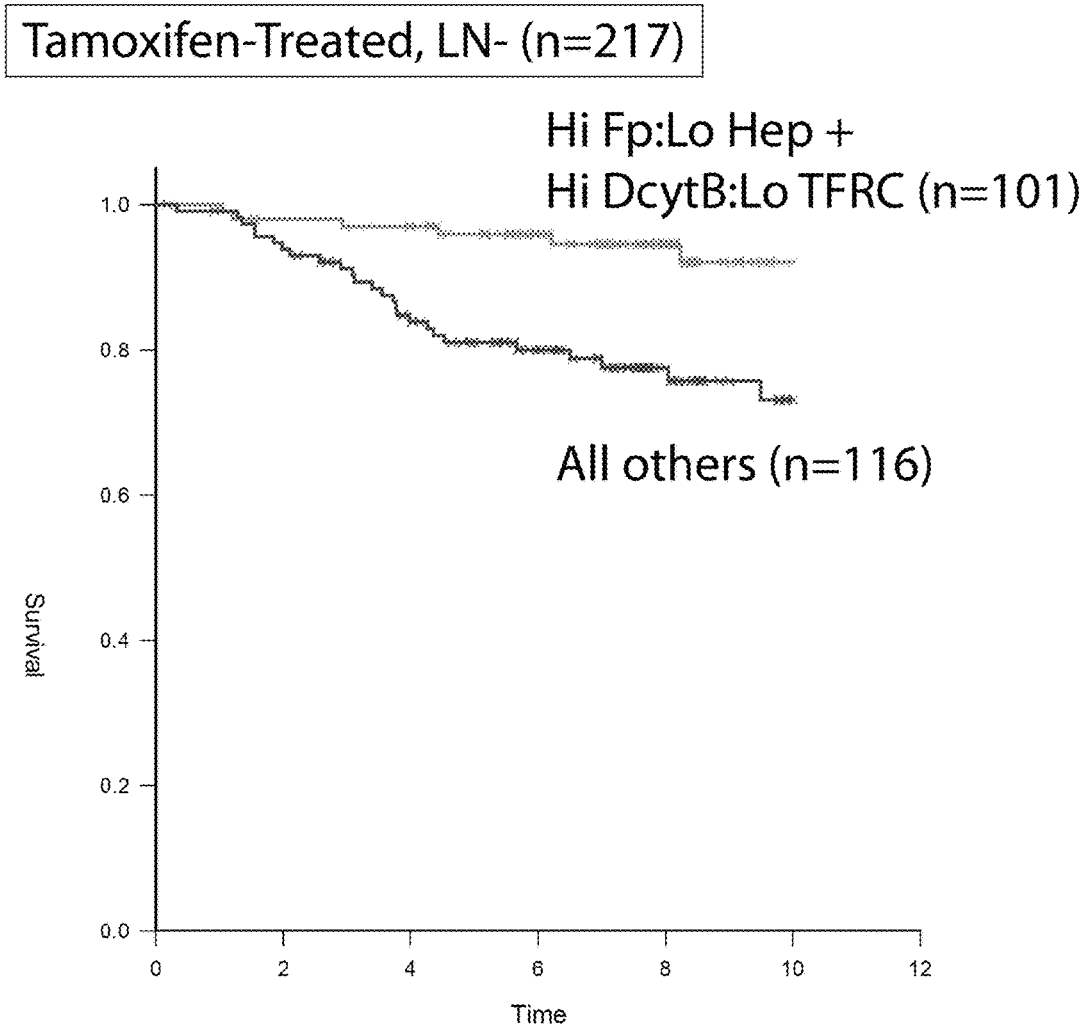

FIG. 17. Kaplan-Meier plot is shown for Tamoxifen-treated, LN− patients divided into two groups: low risk group and high risk group. The low risk group (green survival curve) is defined as those patients whose tumors express 1) high Feroportin (Fp) and low Hepcidin (Hep), or 2) high DcytB (aka, CYBRD1) and low transferring receptor (TFRC) (n=101). The high risk group (red survival curve) is defined as patients with tumors whose gene expression patterns do not meet the low risk criteria (n=116).

Figure 18:
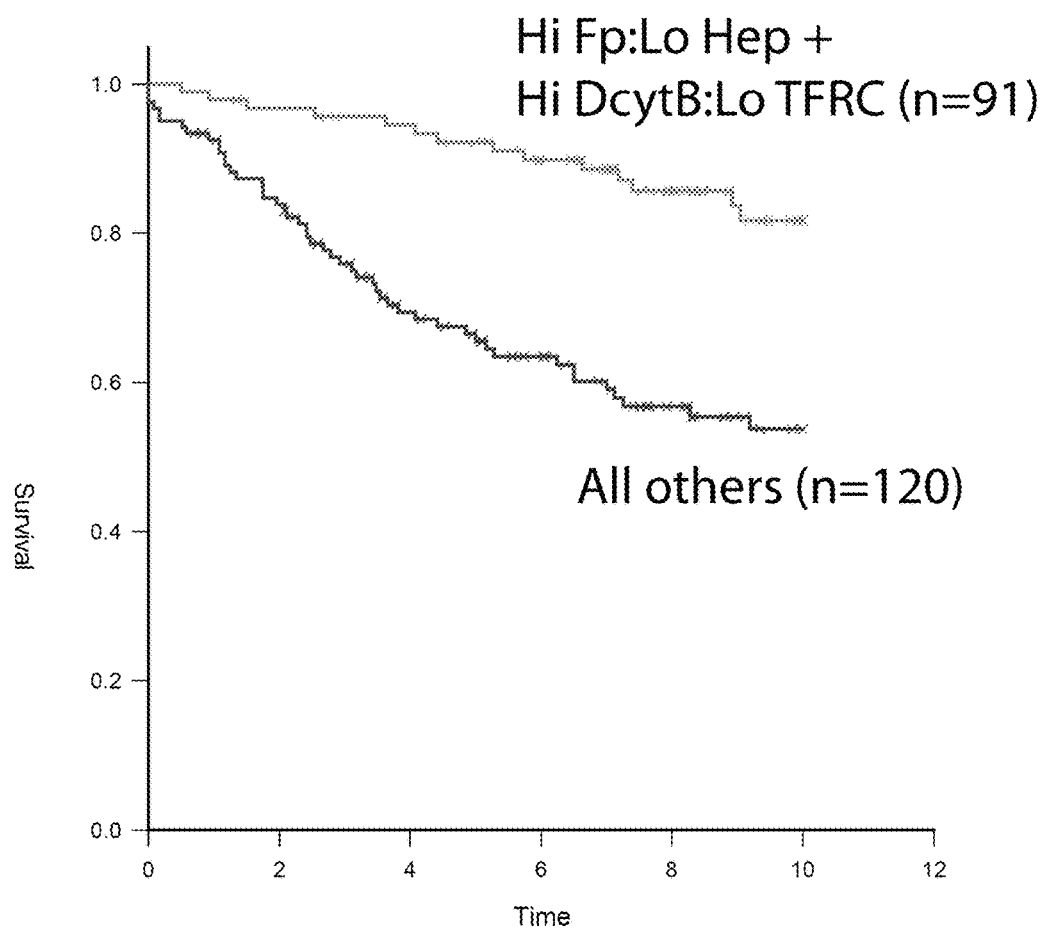

FIG. 18. Kaplan-Meier plot is shown for Tamoxifen-treated, LN+ patients divided into two groups: low risk group and high risk group. The low risk group (green survival curve) is defined as those patients whose tumors express 1) high Feroportin (Fp) and low Hepcidin (Hep), or 2) high DcytB (aka, CYBRD1) and low transferring receptor (TFRC) (n=91). The high risk group (red survival curve) is defined as patients with tumors whose gene expression patterns do not meet the low risk criteria (n=120). High and Low expression of the genes is defined as above and below the mean of the population of the original 759 breast cancer cases (only 741 have associated outcome data). Outcome is defined as distant metastasis-free survival).

Figure 19:
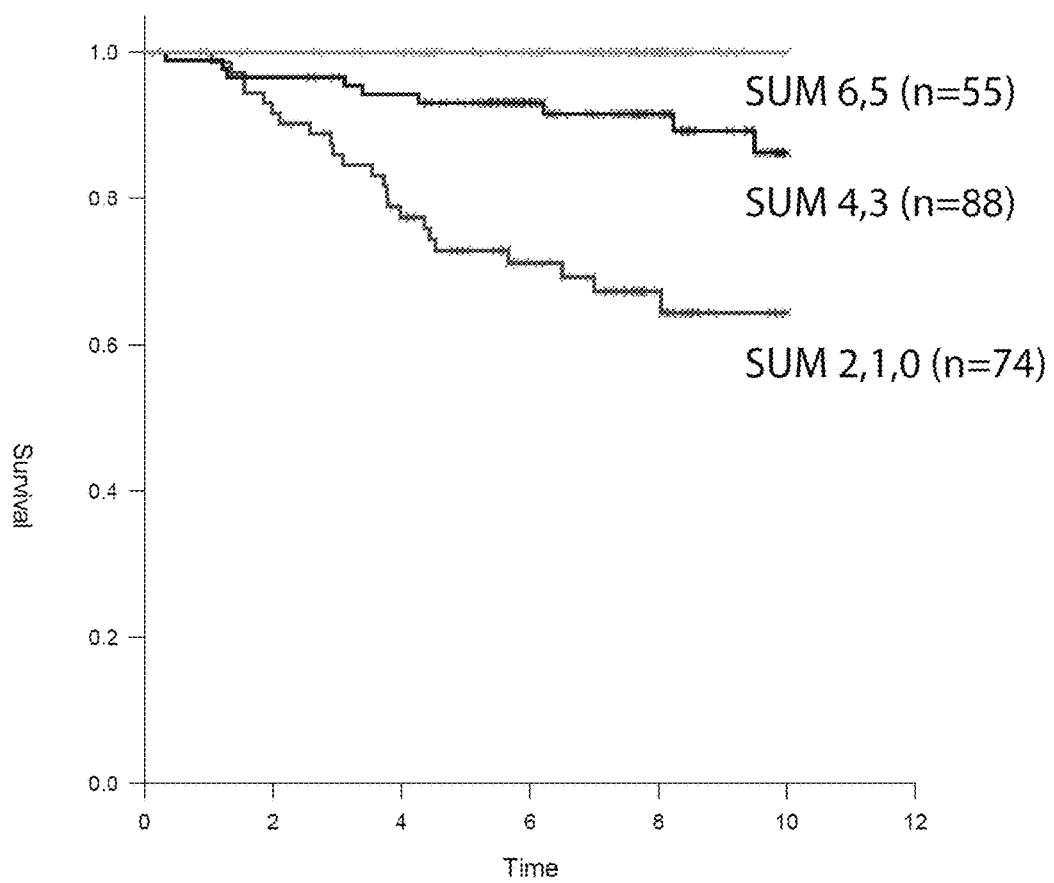

FIG. 19. Kaplan-Meier plot is shown for Tamoxifen-treated, LN− patients divided into 3 groups: low risk group, intermediate risk group and high risk group. The low risk group (green survival curve) is defined as those patients whose 6-gene model scores summed to 5 or 6 (n=55); the intermediate risk group (blue curve) is defined as those patients whose 6-gene model scores summed to 4 or 3 (n=88); and the high risk group (red curve) is defined as those patients whose 6-gene model scores summed to 0, 1 or 2 (n=74).

Figure 20:
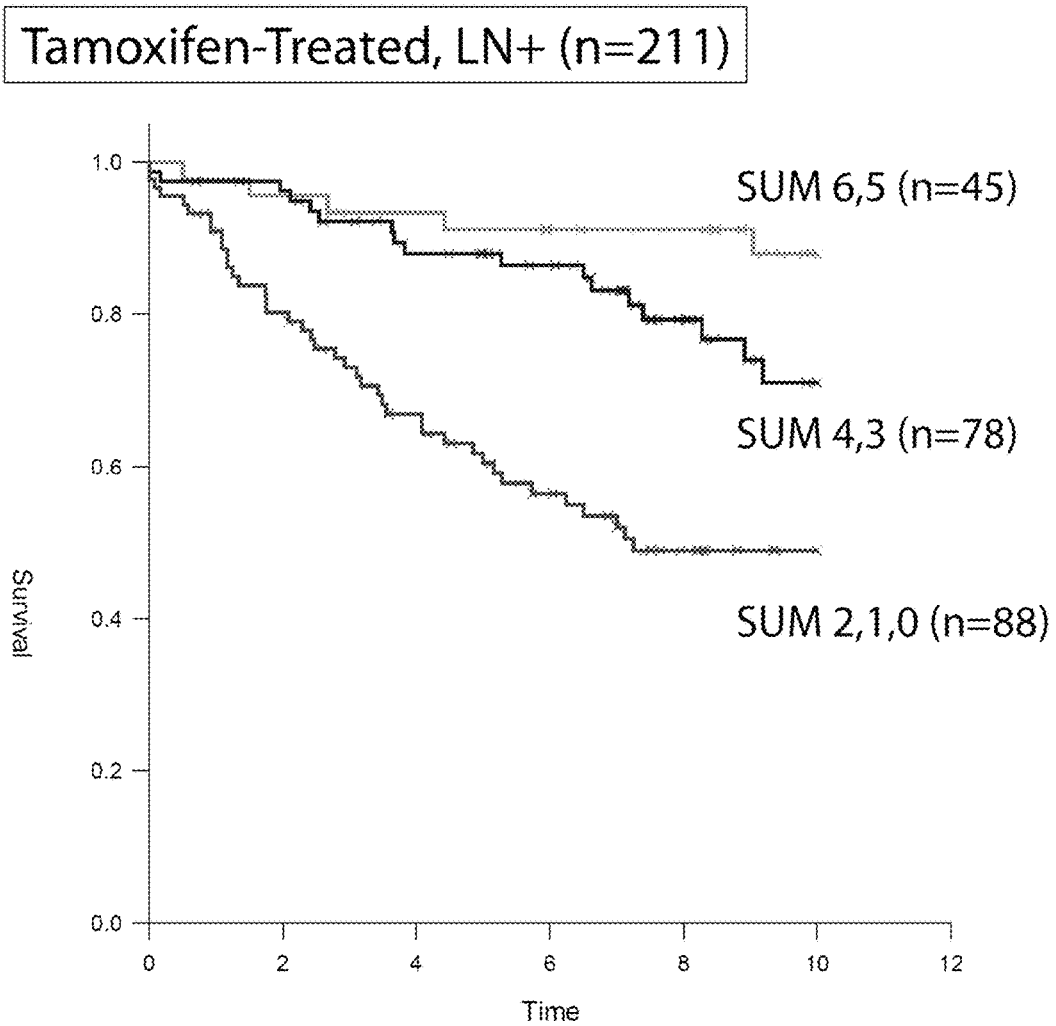

FIG. 20. Kaplan-Meier plot is shown for Tamoxifen-treated, LN+ patients divided into 3 groups: low risk group, intermediate risk group and high risk group. The low risk group (green survival curve) is defined as those patients whose 6-gene model scores summed to 5 or 6 (n=45); the intermediate risk group (blue curve) is defined as those patients whose 6-gene model scores summed to 4 or 3 (n=78); and the high risk group (red curve) is defined as those patients whose 6-gene model scores summed to 0, 1 or 2 (n=88).

Figure 21:
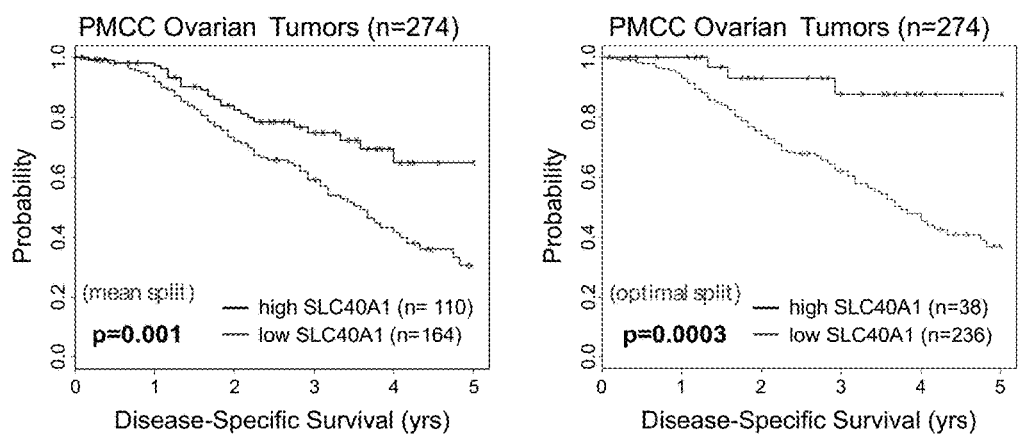

FIG. 21. Kaplan-Meier survival plot showing that expression levels of ferroportin are also positively correlated with survival of ovarian cancer patients.

FIG. 22A-FIG. 22B. Iron regulatory gene signature (IRGS) and distant metastasis-free survival (DMFS) in breast cancer cohorts. Training and test cohorts were stratified into low, intermediate and high risk groups using an iron regulatory gene signature ($\alpha$=0.01, 2 principle components). DMFS was assessed using Kaplan-Meier plots. FIG. 22A. Training cohort (n=337); FIG. 22B. Test cohort (n=337). Logrank test p-values reflect the significance of the hazard ratios.

FIG. 23A-FIG. 23F. IRGS and breast cancer subtypes. FIG. 23A, FIG. 23B. The test cohort was divided into ER+ and ER− groups. Within each group, patients were stratified according to IRGS risk and DMFS was analyzed using Kaplan-Meier plots. A. ER+ patients (n=295); FIG. 23B. ER− patients (n=40). FIG. 23C-FIG. 23F. Patients in the test cohort were assigned to molecular subtypes as described in Materials and Methods. Within each subtype, patients were stratified into IRGS risk groups and DMFS was analyzed using Kaplan-Meier plots. FIG. 23C. Basal subtype (n=45); FIG. 23D. LumA subtype (n=108); FIG. 23E. Normal-like subtype, (n=77); FIG. 23F. LumB subtype (n=67).

Figure 24A:
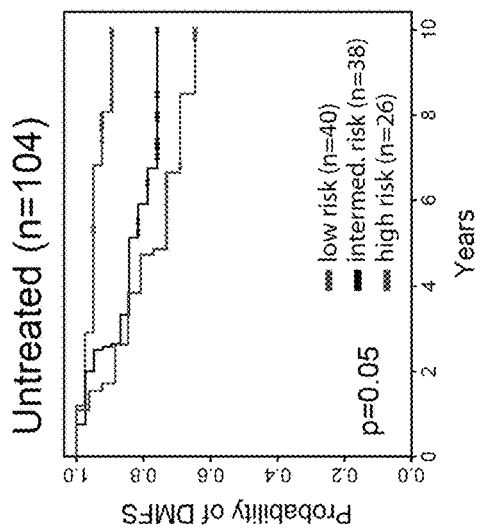
Figure 24B:
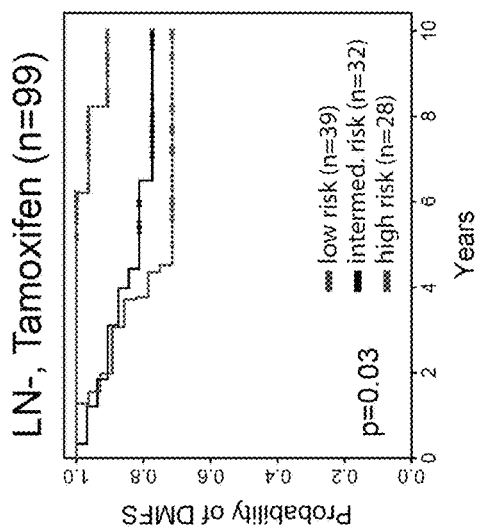
Figure 24C:
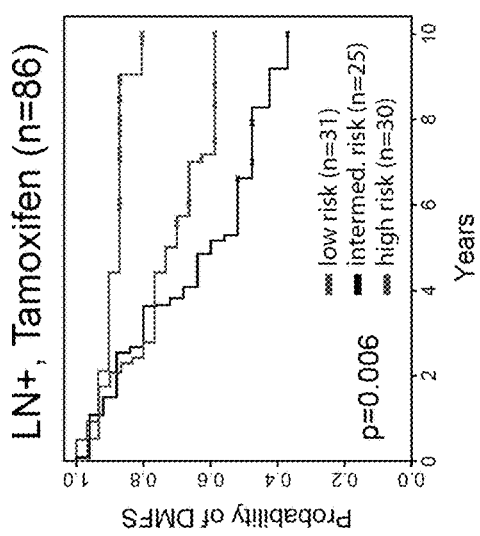

FIG. 24A-FIG. 24C. IRGS in homogeneously treated breast cancer patients. Patients in the test cohort were assigned to groups based on treatment: untreated or tamoxifen monotherapy. Patients treated with tamoxifen were further divided into lymph node negative (LN−) and lymph node positive (LN+) cohorts. Patients in each treatment group were divided into IRGS risk groups and DMFS was analyzed on Kaplan-Meier plots. FIG. 24A. Untreated (n=104); FIG. 24B. LN−, tamoxifen treated (N=99); FIG. 24C. LN+, tamoxifen treated (n=86).

Figure 25C:
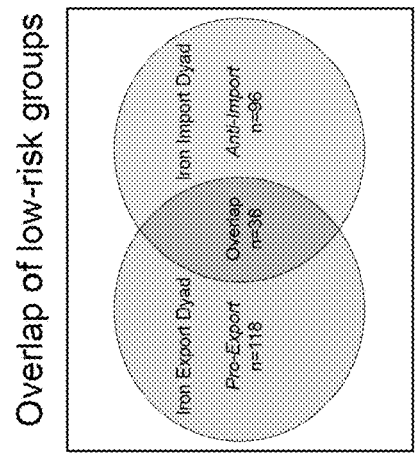
Figure 25B:
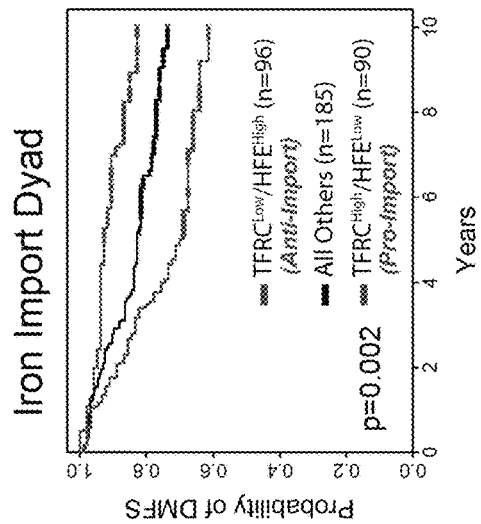
Figure 25A:
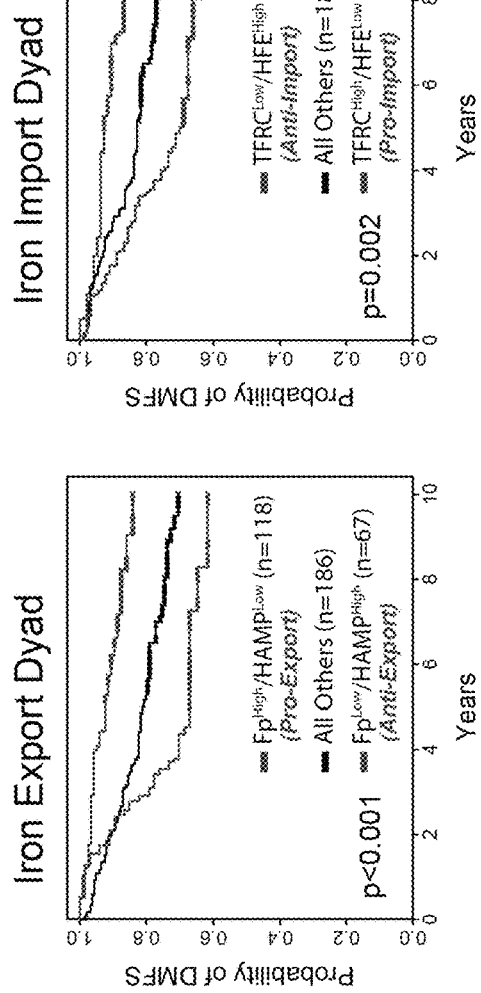

FIG. 25A-FIG. 25C. Gene dyads within the IRGS are associated with DMFS. FIG. 25A. Expression of Fp and HAMP in ER+ patients treated with tamoxifen monotherapy in the combined cohort. Expression was classified as high or low based on the population mean. Patients were divided into three groups: $FP^{High}/HAMP^{Low}$ ("pro-export"); $FP^{Low}/HAMP^{High}$ ("anti-export"); and all others. DMFS of each group was assessed using Kaplan-Meier plots. FIG. 25B. Expression of TFRC and HFE was analyzed similarly. FIG. 25C. Overlap among patients exhibiting a prognostically favorable iron export gene expression pattern ($FP^{High}/HAMP^{Low}$) and favorable iron import gene expression pattern ($TFRC^{Low}/HFE^{High}$) is plotted on a Venn diagram.

FIG. 26A-FIG. 26B. Ferroportin is down-regulated in primary and metastatic prostate cancer. Shown are box plots of log-transformed ferroportin mRNA expression levels in 2 prostate cancer gene profiling studies: FIG. 26A) Tomlins et al., (2007) Nat. Gen. 39:41-51; FIG. 26B) Varambally et al. (2005) Cancer Cell 8:393-406. T test p-values that reflect differential expression between sample groups are shown.

Figure 27:
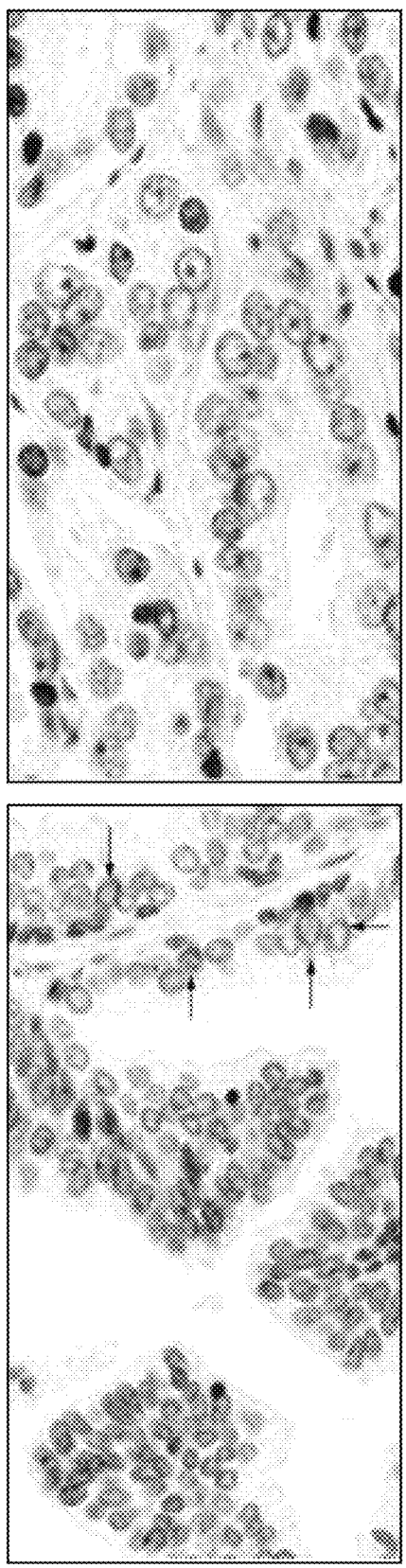

FIG. 27. Formalin fixed, paraffin-embedded (FFPE) tissue from a single prostate cancer patient (Gleason score 7) showing both normal (left) and malignant (right) regions stained with MTP-1 anti-FPN antibody.

DETAILED DESCRIPTION OF THE INVENTION

Many proteins have been identified which modulate iron homeostasis in the body. For example, ferroportin and hepcidin are critical proteins in the regulation of systemic iron homeostasis. Ferroportin is the only known exporter of intracellular non-heme iron; its stability is regulated by the hormone hepcidin. We demonstrate that both ferroportin and hepcidin are expressed in cultured human breast epithelial cells and that hepcidin regulates ferroportin in these cells. Further, ferroportin protein is substantially reduced in breast cancer cells compared to non-malignant breast epithelial cells; ferroportin protein expression correlates with metabolically available iron. Ferroportin protein is also present in normal human mammary tissue and strikingly decreased in breast cancer tissue, with the highest degree of anaplasia associated with lowest ferroportin expression. Transfection of breast cancer cells with ferroportin significantly reduces their growth following orthotopic implantation in the mouse mammary fat pad. Gene expression profiles from >800 women reveal that decreased ferroportin gene expression is associated with a significant reduction in metastasis-free and disease-specific survival that is independent of other breast cancer risk factors. High ferroportin/low hepcidin gene expression profiles identify an extremely favorable cohort of breast cancer patients that have a 10-year survival >90%.

In another aspect of the invention, we have recently discovered that ferroportin (FP), an iron efflux pump, is substantially downregulated in prostate cancer. Strikingly, ferroportin was further downregulated in prostate metastases (see FIG. 26). These investigations were prompted by our discovery that ferroportin is a central regulatory node in in cancer growth in human mammary cancer cells and murine models, and predicts the outcome of women 10 years after diagnosis. These laboratory and clinical observations linking ferroportin and cancer have a biological basis: cancer cells require iron for growth and metabolic functions associated with motility and metastasis, suggesting that reduction in ferroportin traps iron in cancer cells so that it can be used to promote growth.

The clinical implications of a prognostic marker in prostate cancer are substantial, given the absence in prostate cancer of useful predictors that might alter patient treatment. The data presented herein implicate a role for ferroportin and its regulator hepcidin as molecular classifiers for prostate cancer.

Clearly, ferroportin is a pivotal protein in breast biology and a strong and independent predictor of prognosis in cancer, particularly breast, ovarian and prostate cancer.

Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The phrase "iron homeostasis" refers to processes involved in the maintenance of an internal equilibrium of iron ions at the level of a cell.

The phrase "iron homeostasis associated (IHA) marker(s)" refers to a class of proteins involved in iron homeostasis, iron transport and iron metabolism. Such proteins include, without limitation, those listed in the Tables below. Markers also include the nucleic acids encoding the proteins listed.

The phrase "iron regulatory gene signature (IRGS) refers to a set of genes encoding proteins that participate in iron transport and/or iron homeostasis which exhibit altered expression levels in cancerous vs. normal cells. Alterations in the IRGS are useful for predicting likelihood of cancer recurrence in patients with certain kinds of cancers and therefore provide the clinician with guidance regarding appropriate treatment regimens. Such cancers include, without limitation, breast, ovarian and prostate cancer. An IRGS useful to predict cancer recurrence is provided in Table I. Table II provides a list of known genes encoding proteins involved in iron homeostasis and metabolism. Table III includes the markers from Table I and others that are also useful for predicting cancer recurrence.

TABLE 1 iron homeostasis associated (IHA) markers comprising.

| GENE NAME | SYMBOL | Genbank | Affymetrix Probe Set ID |
| --- | --- | --- | --- |
| Cytochrome b reductase 1 | CYBRD1 | AL136693; NM_024843 | 222453_at |
| Six transmembrane epithelial antigen of the prostate 1 | STEAP1 | NM_012449 | 205542_at |
| Six transmembrane epithelial antigen of the prostate 2 | STEAP2 | BF680588 | 225871_at |
| Scavenger receptor class A, member 5 (putative) | SCARA5 | AI799784; BE787752 | 229839_at |
| Lactotransferrin | LTF | NM_002343 | 202018_s_at |
| Transferrin receptor (p90, CD71); Transferrin receptor protein 1 | TFRC | BE676623; NM_003234 | 240686_x_at |
| Feroportin; Solute carrier family 40 (iron-regulated transporter), member 1 | SLC40A1 | AL136944; NM_014585 | 223044_at |
| Iron-sulfur cluster scaffold homolog (E. coli) | ISCU | AY009128 | 209075_s_at |
| Sideroflexin 5 | SFXN5 | AA725691 | 241999_at |
| Sideroflexin 1 | SFXN1 | NM_022754 | 218392_x_at |
| Endothelial PAS domain protein 1 | EPAS1 | AF052094 | 200878_at |
| Hemochromatosis | HFE | NM_000410 | 206087_x_at |
| ATP-binding cassette, sub-family G (WHITE), member 2 | ABCG2 | AF098951 | 209735_at |
| Hepcidin antimicrobial peptide | HAMP | NM_021175 | 220491_at |
| Transmembrane protease, serine 6 | TMPRSS6 | NM_153609 | 232941_at |
| Iron-responsive element binding protein 2 | IREB2 | NM_004136 | 225892_at |
| Ferritin, light polypeptide | FTL | NM_000146 | 212788_x_at |
| Ferritin, heavy polypeptide 1 | FTH1 | NM_002032 | 214211_at |

TABLE II iron homeostasis associated markers identified to date

| GENE NAME | SYMBOL | REPRESENTATIVE GENBANK ACCESSION | UNIGENE CLUSTER ID (build #230; August 2011) | CHROMOSOME LOCATION |
|---|---|---|---|---|
| ATP-binding cassette, sub-family B (MDR/TAP), member 6 | ABCB6 | NM_005689 | Hs.107911 | 2q36 |
| ATP-binding cassette, sub-family B (MDR/TAP), member 7 | ABCB7 | NM_004299 | Hs.370480 | Xq13.3 |
| ATP-binding cassette, sub-family G (WHITE), member 2 | ABCG2 | NM_004827 | Hs.480218 | 4q22 |
| Aconitase 1, soluble | ACO1 | AB209480 | Hs.567229 | 9p22-q32\|9p21.1 |
| Aminolevulinate dehydratase | ALAD | AK131490 | Hs.1227 | 9q33.1 |
| Aminolevulinate, delta-, synthase 1 | ALAS1 | NM_000688 | Hs.476308 | 3p21.1 |
| Aminolevulinate, delta-, synthase 2 | ALAS2 | NM_000032 | Hs.522666 | Xp11.21 |
| Amyloid beta (A4) precursor protein | APP | NM_000484 | Hs.434980 | 21q21.2\|21q21.3 |
| Bone morphogenetic protein 6 | BMP6 | NM_001718 | Hs.285671 | 6p24-p23 |
| Calreticulin | CALR | M84739 | Hs.515162 | 19p13.3-p13.2 |
| CDC14 cell division cycle 14 homolog A (S. cerevisiae) | CDC14A | BC071578 | Hs.127411 | 1p21 |
| Cytosolic iron-sulfur protein assembly 1 | CIAO1 | NM_004804 | Hs.12109 | 2q11.2 |
| Ceruloplasmin (ferroxidase) | CP | NM_000096 | Hs.558314 | 3q23-q25 |
| Cytochrome b reductase1 | CYBRD1 | NM_024843 | Hs.221941 | 2q31.1 |
| Egl nine homolog 1 (C. elegans) | EGLN1 | NM_022051 | Hs.444450 | 1q42.1 |
| Egl nine homolog 2 (C. elegans) | EGLN2 | AK098182 | Hs.515417 | 19q13.2 |
| Egl nine homolog 3 (C. elegans) | EGLN3 | AK025273 | Hs.135507 | 14q13.1 |
| Endothelial PAS domain protein1 | EPAS1 | NM_001430 | Hs.468410 | 2p21-p16 |
| F-box and leucine-rich repeat protein 5 | FBXL5 | NM_012161 | Hs.643433 | 4p15.32 |
| Ferrochelatase | FECH | NM_001012515 | Hs.365365 | 18q21.3 |
| Feline leukemia virus subgroup C cellular receptor 1 | FLVCR1 | NM_014053 | Hs.7055 | 1q32.3 |
| Ferritin, heavy polypeptide1 | FTH1 | BM905227 | Hs.524910 | 11q13 |
| Ferritin, light polypeptide | FTL | BF244604 | Hs.433670 | 19q13.33 |
| ferritin mitochondrial | FTMT | NM_177478 | Hs.105324 | 5q21.3 |
| Frataxin | FXN | NM_181425 | Hs.20685 | 9q21.11 |
| Glutaredoxin 5 | GLRX5 | CR936698 | Hs.728210 | 14q32.13 |
| Hepcidin antimicrobial peptide | HAMP | DR004094 | Hs.8821 | 19q13.1 |
| Hephaestin | HEPH | NM_138737 | Hs.31720 | Xq11-q12 |
| Hemochromatosis | HFE | NM_000410 | Hs.233325 | 6p21.3 |
| Hemochromatosis type 2 (juvenile) | HFE2 | NM_213653 | Hs.632436 | 1q21.1 |
| Hypoxia inducible factor 1, alpha subunit (basic helix-loop-helix transcription factor) | HIF1A | NM_001530 | Hs.597216 | 14q23.2 |
| Hypoxia inducible factor 1, alpha subunit inhibitor | HIF1AN | NM_017902 | Hs.500788 | 10q24 |
| Hydroxymethylbilane synthase | HMBS | BU168137 | Hs.82609 | 11q23.3 |
| Heme oxygenase (decycling) 1 | HMOX1 | BG165629 | Hs.517581 | 22q12\|22q13.1 |
| Heme oxygenase (decycling) 2 | HMOX2 | BG115862 | Hs.284279 | 16p13.3 |
| Haptoglobin | HP | NM_005143 | Hs.513711 | 16q22.1 |
| Haptoglobin-related protein | HPR | NM_020995 | Hs.655361 | 16q22.1 |
| Hemopexin | HPX | NM_000613 | Hs.426485 | 11p15.5-p15.4 |
| HscB iron-sulfur cluster co-chaperone homolog (E. coli) | HSCB | NM_172002 | Hs.632780 | 22q12.1 |
| Iron-responsive element binding protein2 | IREB2 | NM_004136 | Hs.436031 | 15q25.1 |
| Iron-sulfur cluster assembly 1 homolog (S. cerevisiae) | ISCA1 | NM_030940 | Hs.449291 | 9q21.33 |
| Iron-sulfur cluster assembly 2 homolog (S. cerevisiae) | ISCA2 | BQ224801 | Hs.291079 | 14q24.3 |
| Iron-sulfur cluster scaffold homolog (E.coli) | ISCU | AK057251 | Hs.615131 | 12q24.1 |
| Low density lipoprotein receptor-related protein 2 | LRP2 | NM_004525 | Hs.657729 | 2q24-q31 |
| Lactotransferrin | LTF | AK093852 | Hs.529517 | 3p21.31 |
| Antigen p97 (melanoma associated) identified by monoclonal antibodies 133.2 and 96.5 | MFI2 | NM_005929 | Hs.184727 | 3q28-q29 |
| MON1 homolog A (yeast) | MON1A | NM_032355 | Hs.655014 | 3p21.31 |
| Metal-regulatory transcription factor 1 | MTF1 | NM_005955 | Hs.471991 | 1p33 |
| Nuclear prelamin A recognition factor-like | NARFL | AK056467 | Hs.513247 | 16p13.3 |
| Neogenin 1 | NEO1 | NM_002499 | Hs.388613 | 15q22.3-q23 |
| NFS1 nitrogen fixation 1 homolog (S. cerevisiae) | NFS1 | AK056242 | Hs.194692 | 20q11.22 |
| NFU1 iron-sulfur cluster scaffold homolog (S. cerevisiae) | NFU1 | BX538347 | Hs.430439 | 2p15-p13 |
| Protoporphyrinogen oxidase | PPOX | AK094855 | Hs.517373 | 1q22 |
| Scavenger receptor class A, member 5(putative) | SCARA5 | NM_173833 | Hs.591833 | 8p21.1 |
| Succinate dehydrogenase complex assembly factor 1 | SDHAF1 | BM802990 | Hs.356460 | 19q13.12 |
| Succinate dehydrogenase complex, subunit B, iron sulfur (Ip) | SDHB | BQ073692 | Hs.465924 | 1p36.1-p35 |
| Sideroflexin 1 | SFXN1 | NM_022754 | Hs.369440 | 5q35.3 |
| Sideroflexin 2 | SFXN2 | BC022091 | Hs.44070 | 10q24.32 |
| Sideroflexin 3 | SFXN3 | AK091504 | Hs.283844 | 10q24.31 |
| Sideroflexin 4 | SFXN4 | BC050475 | Hs.655168 | 10q26.11 |
| Sideroflexin 5 | SFXN5 | BX640669 | Hs.368171 | 2p13 |
| Solute carrier family 11 (proton-coupled divalent metal ion transporters), member 1 | SLC11A1 | NM_000578 | Hs.591607 | 2q35 |
| Solute carrier family 11 (proton-coupled divalent metal ion transporters), member 2 | SLC11A2 | NM_001174129 | Hs.505545 | 12q13 |
| Solute carrier family 22, member 17 | SLC22A17 | BX161416 | Hs.373498 | 14q11.2 |
| Solute carrier family 25, member 28 | SLC25A28 | CR591608 | Hs.403790 | 10q24.2 |
| Solute carrier family 25, member 37 | SLC25A37 | AK127666 | Hs.726050 | 8p21.2 |
| Solute carrier family 39 (zinc transporter), member 14 | SLC39A14 | NM_001135153 | Hs.491232 | 8p21.3 |

TABLE II-continued iron homeostasis associated markers identified to date

| GENE NAME | SYMBOL | REPRESENTATIVE GENBANK ACCESSION | UNIGENE CLUSTER ID (build #230; August 2011) | CHROMOSOME LOCATION |
| --- | --- | --- | --- | --- |
| Solute carrier family 40 (iron-regulated transporter), member 1 (Feroportin) | SLC40A1 | BC037733 | Hs.643005 | 2g32 |
| solute carrier family 46 (folate transporter), member | SLC46A1 | NM_001242366 | Hs.446689 | 17q11.2 |
| Six transmembrane epithelial antigen of theprostate1 | STEAP1 | BF673939 | Hs.61635 | 7q21 |
| Six transmembrane epithelial antigen of theprostate2 | STEAP2 | NM_152999 | Hs.489051 | 7q21 |
| STEAP family member 3 | STEAP3 | AL833624 | Hs.647822 | 2q14.2 |
| STEAP family member 4 | STEAP4 | NM_024636 | Hs.521008 | 7q21.12 |
| Transferrin | TF | CR936810 | Hs.518267 | 3q22.1 |
| Transferrin receptor 2 | TFR2 | BC142630 | Hs.544932 | 7q22 |
| Transferrin receptor (p90, CD71) | TFRC | NM_003234 | Hs.529618 | 3q29 |
| Transmembrane protease, serine6 | TMPRSS6 | NM_153609 | Hs.370885 | 22q12.3 |
| Uroporphyrinogen decarboxylase | UROD | BX647308 | Hs.78601 | 1p34 |
| Uroporphyrinogen III synthase | UROS | AK092076 | Hs.501376 | 10q25.2-q26.3 |

In further studies we identified IHA genes univariately associated with distant metastasis-free survival. These are provided in Table III which includes most of the markers set forth in in Table I.

TABLE III

IHA genes univariately associated with distant metastasis-free survival.

| GENE NAME | SYMBOL | COX P-VALUE | HAZARD RATIO | 95% CI | REPRESENTATIVE AFFYMETRIX PROBE SET ID | IRGS GENES |
| --- | --- | --- | --- | --- | --- | --- |
| Cytochrome b reductase1 | CYBRD1 | 1.83E−07 | 0.60 | 0.49-0.72 | 222453_at | + |
| Six transmembrane epithelial antigen ofthe prostate 1 | STEAP1 | 4.21E−06 | 0.59 | 0.47-0.73 | 205542_at | + |
| Six transmembrane epithelial antigen ofthe prostate 2 | STEAP2 | 2.02E−05 | 0.60 | 0.47-0.76 | 225871_at | + |
| Hemochromatosis | HFE | 3.05E−04 | 0.34 | 0.19-0.61 | 206087_x_at | + |
| Scavenger receptor class A, member 5(putative) | SCARA5 | 4.02E−04 | 0.44 | 0.27-0.69 | 229839_at | + |
| Lactotransferrin | LTF | 4.16E−04 | 0.84 | 0.76-0.92 | 202018_s_at | + |
| Transferrin receptor (p90, CD71) | TFRC | 6.16E−04 | 3.54 | 1.71-7.29 | 240686_x_at | + |
| Solute carrier family 40 (iron-regulated transporter), member 1 (Feroportin) | SLC40A1 | 7.00E−04 | 0.76 | 0.64-0.88 | 223044_at | + |
| Iron-sulfur cluster scaffold homolog (E.coli) | ISCU | 7.74E−04 | 0.41 | 0.23-0.68 | 209075_s_at | + |
| Sideroflexin 1 | SFXN1 | 8.33E−04 | 2.02 | 1.33-3.06 | 218392_x_at | + |
| Endothelial PAS domain protein1 | EPAS1 | 1.07E−03 | 0.57 | 0.40-0.79 | 200878_at | + |
| Solute carrier family 25, member 37 | SLC25A37 | 2.13E−03 | 0.55 | 0.37-0.80 | 226179_at | + |
| Amyloid beta (A4) precursor protein | APP | 2.83E−03 | 0.59 | 0.42-0.83 | 214953_s_at | |
| ATP-binding cassette, sub-family G (WHITE), member 2 | ABCG2 | 3.82E−03 | 0.45 | 0.26-0.77 | 209735_at | + |
| Sideroflexin 5 | SFXN5 | 5.41E−03 | 4.00 | 1.50-10.6 | 241999_at | + |
| Hypoxia inducible factor 1, alpha subunit inhibitor | HIF1AN | 6.53E−03 | 0.51 | 0.31-0.83 | 226648_at | + |
| Aminolevulinate dehydratase | ALAD | 8.68E−03 | 0.49 | 0.29-0.83 | 218487_at | + |
| Low density lipoprotein receptor-related protein 2 | LRP2 | 1.56E−02 | 0.85 | 0.74-0.96 | 230863_at | |
| Solute carrier family 22, member 17 | SLC22A17 | 1.57E−02 | 0.62 | 0.42-0.91 | 218675_at | |
| Ferrochelatase | FECH | 1.66E−02 | 0.33 | 0.13-0.81 | 229696_at | |
| Uroporphyrinogen decarboxylase | UROD | 1.68E−02 | 0.46 | 0.24-0.87 | 208970_s_at | |
| Feline leukemia virus subgroup C cellular receptor 1 | FLVCR1 | 1.75E−02 | 1.52 | 1.07-2.13 | 222906_at | |
| Glutaredoxin 5 | GLRX5 | 2.40E−02 | 1.92 | 1.08-3.39 | 221932_s_at | |
| Metal-regulatory transcription factor 1 | MTF1 | 2.60E−02 | 0.54 | 0.31-0.92 | 227150_at | |
| Heme oxygenase (decycling) 2 | HMOX2 | 2.83E−02 | 2.63 | 1.10-6.24 | 218121_at | |
| Iron-sulfur cluster assembly 1 homolog (S. cerevisiae) | ISCA1 | 3.25E−02 | 0.59 | 0.36-0.95 | 209274_s_at | |
| STEAP family member 4 | STEAP4 | 3.61E−02 | 0.85 | 0.72-0.98 | 225987_at | |
| Transmembrane protease, serine6 | TMPRSS6 | 3.61E−02 | 3.52 | 1.08-11.4 | 232941_s_at | |
| F-box and leucine-rich repeat protein 5 | FBXL5 | 3.81E−02 | 0.62 | 0.39-0.97 | 209004_s_at | |
| Transferrin receptor 2 | TFR2 | 3.92E−02 | 2.85 | 1.05-7.70 | 215863_at | |
| Cytosolic iron-sulfur protein assembly 1 | CIAO1 | 4.05E−02 | 1.85 | 1.02-3.31 | 203536_s_at | |
| Hepcidin antimicrobial peptide | HAMP | 4.55E−02 | 1.65 | 1.01-2.68 | 220491_at | |
| Transcribed locus | BMP6 | 4.68E−02 | 2.94 | 1.01-8.53 | 215042_at | |
| Solute carrier family 11 (proton-coupled divalent metal ion transporters), member 1 | SLC11A1 | 5.18E−02 | 1.90 | 0.99-3.63 | 210423_s_at | |
| Transferrin | TF | 5.25E−02 | 11.01 | 0.97-124. | 220109_at | |

TABLE III-continued

IHA genes univariately associated with distant metastasis-free survival.

| GENE NAME | SYMBOL | COX P-VALUE | HAZARD RATIO | 95% CI | REPRESENTATIVE AFFYMETRIX PROBE SET ID | IRGS GENES |
|---|---|---|---|---|---|---|
| Hypoxia inducible factor 1, alpha subunit (basic helix-loop-helix transcription factor) | HIF1A | 5.27E−02 | 1.40 | 0.99-1.97 | 200989_at | |
| solute carrier family 46 (folate transporter), member | SLC46A1 | 5.30E−02 | 3.51 | 0.98-12.5 | 233531_at | |

Underlined are 15 of the 18 genes shown in Table I and previously identified as IHA markers in PCT/US10/52072.

Upon further analysis eight exemplary prognostic models of recurrent disease risk were developed. See Table IV. Determining the expression levels of the IHA markers listed in each model provides the clinician with guidance as those patients which have an elevated risk for recurrent disease. The expression levels of the genes listed in each model provide strong prognostic information. Accordingly, the invention entails determination of the expression levels of at least two, or more (e.g., 4, 5, 6, 15, 18 or 79) of the IHA markers of the invention and comparing those expression levels with those previously determined to be associated with aggressive malignant disease.

phages, and is an essential component of systemic iron homeostasis. Sequence information for ferroportin has been deposited in GenBank, Accession No. NM_014585.

Hepcidin (also referred to as HAMP) is a peptide hormone produced by the liver, and appears to be the master regulator of iron homeostasis in humans and other mammals. Hepcidin directly inhibits ferroportin, a protein that transports iron out of the cells that store it. Ferroportin is present on enterocytes and macrophages. By inhibiting ferroportin, hepcidin prevents enterocytes of the intestines from secreting iron into the hepatic portal system, thereby functionally reducing iron absorption. Iron release from macrophages is also prevented by ferroportin inhibition.

TABLE IV

Eight prognostic models and the IHA genes that comprise them.

| GENE NAME | SYMBOL | 16 IRGS GENES | 6-GENE (Set A) | 6-GENE (Set B) | 6-GENE CORE SET | 4-GENE CORE SET | 2-GENE CORE SET | IRON EXPORT DYAD | IRON IMPORT DYAD |
|---|---|---|---|---|---|---|---|---|---|
| Transferrin receptor (p90, CD71) | TFRC | + | + | + | | | | | + |
| Hemochromatosis | HFE | + | | | | | | | + |
| Sideroflexin 1 | SFXN1 | + | | | + | + | | | |
| Six transmembrane epithelial antigen of the prostate 1 | STEAP1 | + | | + | + | + | | | |
| Six transmembrane epithelial antigen of the prostate 2 | STEAP2 | + | | + | + | + | | | |
| Iron-sulfur cluster scaffold homolog (E. coli) | ISCU | + | | + | + | + | | | |
| Cytochrome b reductase 1 | CYBRD1 | + | | + | + | | + | | |
| Scavenger receptor class A, member 5 (putative) | SCARA5 | + | | | + | | + | | |
| Hepcidin antimicrobial peptide | HAMP | | | | | | | + | |
| Solute carrier family 40 (iron-regulated transporter), member 1 (Feroportin) | SLC40A1 | + | | + | | | | + | |
| Lactotransferrin | LTF | + | | | | | | | |
| Endothelial PAS domain protein 1 | EPAS1 | + | | | | | | | |
| Solute carrier family 25, member 37 | SLC25A37 | + | | | | | | | |
| ATP-binding cassette, sub-family G (WHITE), member 2 | ABCG2 | + | | | | | | | |
| Sideroflexin 5 | SFXN5 | + | | | | | | | |
| Hypoxia inducible factor 1, alpha subunit inhibitor | HIF1AN | + | | | | | | | |
| Aminolevulinate dehydratase | ALAD | + | | | | | | | |
| Transmembrane protease, serine 6 | TMPRSS6 | | + | | | | | | |
| Transferrin | TF | | + | | | | | | |
| Ferritin, heavy polypeptide 1 | FTH1 | | + | | | | | | |
| Ferritin, light polypeptide | FTL | | + | | | | | | |
| Iron-responsive element binding protein 2 | IREB2 | | + | | | | | | |

Results obtained using the particular combinations and subcombinations, including the 16 member IRGS combination are described further herein below in the Examples.

Ferroportin (ferroportin 1, also termed Ireg1, MTP1, SLC40A1) is a recently described cell surface transmembrane protein and is the only known export protein for non-heme iron. Ferroportin is expressed at high levels on duodenal enterocytes, placenta, hepatocytes, and macro- Thus, hepcidin maintains iron homeostasis. Hepcidin activity is also partially responsible for iron sequestration seen in anemia of chronic disease. Sequence information for hepcidin has been deposited in GenBank, Accession No. NM_021175.

The phrase "predetermined expression levels" as used herein refers to mean expression levels measured across a patient cohort, tertile or quartile ranges observed in the cohort, or other statistical descriptors that are effective to assign the patients to a particular outcome group.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form. By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to a cancer marker gene or nucleic acid, but does not hybridize to other nucleotides. Also polynucleotide which "specifically hybridizes" may hybridize only to a ferroportin encoding nucleic acid, a hepcidin nucleic acid, or both. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5° C. + 16.6 \text{ Log } [Na+] + 0.41(\% \ G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the iron homeostasis associated marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')$_2$, F(v), scFv, scFv$_2$, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668).

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, Pseudomonas exotoxin, and others listed above); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). In a particular embodiment, the chemotherapeutic agent is selected from the group consisting of: placitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

"Cancer" refers to any of a number of diseases that are characterized by uncontrolled, abnormal proliferation of cells, as well as any of a number of characteristic structural and/or molecular features. A "cancerous cell" is understood as a cell having specific structural properties, lacking differentiation and in many instances, being capable of invasion and metastasis, see DeVita, V. et al. (eds.), 2001, Cancer Principles and Practice of Oncology, 6th. Ed., Lippincott Williams & Wilkins, Philadelphia, Pa.). The term cancer includes, for example, cancers of the female reproductive organs including, for example, ovarian cancer, cervical cancer and uterine cancer; lung cancer; breast cancer; renal cell carcinoma; Hodgkin's lymphoma; Non-Hodgkin's lymphoma; cancers of the genitourinary system including, for example, kidney cancer, prostate cancer, bladder cancer, and urethral cancer; cancers of the head and neck; liver cancer; cancers of the gastrointestinal system including, for example, stomach cancer, esophageal cancer, small bowel cancer or colon cancer; cancers of the biliary tree; pancreatic cancer; cancers of the male reproductive system including, for example, testicular cancer; Gestational trophoblastic disease; cancers of the endocrine system including, for example, thyroid cancer, parathyroid cancer, adrenal gland cancer, carcinoid tumors, insulinomas and PNET tumors; sarcomas, including, for example, Ewing's sarcoma, osteosarcoma, liposarcoma, leiomyosarcoma, and rhabdomyosarcoma; mesotheliomas; cancers of the skin; melanomas; cancers of the central nervous system; pediatric cancers; and cancers of the hematopoietic system including, for example, all forms of leukemia, myelodysplastic syndromes, myeloproliferative disorders and multiple myeloma. Cancers referred to in the present methods include those which exhibit the IHA marker expression profiles described in the Tables provided herein. Exemplary cancers include, for example breast cancer, ovarian cancer and prostate cancer.

"Sample" or "patient sample" or "biological sample" generally refers to a sample which may be tested for expression levels of a particular molecule, preferably a ferroportin molecule, hepcidin molecule or both. Samples may include but are not limited to: cells, including breast cancer cells, ovarian cancer cells, prostate cancer cells and blood cells, biopsy tissue, frozen samples, formalin fixed paraffin embedded tissue or cell samples, body fluids, including blood, serum, plasma, nipple aspirates, seminal fluids and the like.

Methods of Determining Levels of Iron Homeostasis Associated (IHA) Proteins and Nucleic Acids in Cancer Diagnostic Assays The IHA proteins listed in the Tables provided herein, may be used to advantage as biomarkers for predicting clinical outcomes in cancer patients. For example, complementary nucleic acids or fragments thereof which hybridize to the molecules listed in Table 1 may be used as probes to detect the presence of and/or expression of nucleic acids encoding these proteins. Methods in which such nucleic acids may be utilized as probes for such assays include, but are not limited to: (1) in situ hybridization; (2) Southern hybridization (3) northern hybridization; (4) hybridization based assays such as those available from Panomics and High throughput Genomics; (5) assorted amplification reactions such as polymerase chain reactions (PCR), RT-PCR and real time PCR and (6) signal detection based assays such as those available from Luminex. Additionally, new detection technologies are available which enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

In another aspect, the patient sample may have been previously genetically analyzed and thus the genetic expression profile in the sample may be available to the clinician. Accordingly, the method may entail storing reference IHA marker sequence information in a database, i.e., those expression levels statistically associated with a more favorable or less favorable prognosis as described in the tables herein, and performance of comparative genetic analysis on the computer, thereby identifying those patients having increased risk for recurrent disease.

Antibodies to the IHA proteins listed in the Tables are commercially available. For example, anti-ferroportin or anti-hepcidin antibodies or immunologically specific fragments thereof can be used in conventional assays (such as ELISA) to measure ferroportin and hepcidin levels in tissues and bodily fluids of interest.

Thus any of the aforementioned techniques may be used to detect or quantify IHA marker expression and accordingly, diagnose cancer, particularly, breast cancer.

Kits and Articles of Manufacture

Any of the aforementioned products can be incorporated into a kit which may contain polynucleotides which specifically hybridize to one or more nucleic acids encoding the iron homeostasis associated proteins. Optionally, such nucleic acids may be immobilized on a Gene Chip. Such kits may also comprise an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Kits useful for detecting IHA protein levels include, without limitation, antibodies immunologically specific for any, at least 2, 3, 4, 5, 6, 7, 8, 9, 10 or all of the proteins listed in the Tables. For example, the kit may contain antibodies which bind ferroportin and hepcidin or fragments thereof, means for detecting any immune complex formed between the antibody and ferroportion or hepcidin as well as means for quantitating the same. Such antibodies are optionally detectably labeled. Alternatively, a secondary antibody may be employed which contains a detectable label. The kit may also comprise a solid support such as a dish or filter and positive controls. Finally, reagents suitable for performance of an ELISA assay may also be included.

Kits for detection of IHA protein-encoding nucleic acids include complementary nucleic acids which specifically hybridize to IHA protein encoding nucleic acids present in the biological sample being tested, the nucleic acids comprising a detectable label to facilitate quantitation of the IHA protein encoding nucleic acids present in the sample. These kits may also comprise reagents suitable for performance of RT PCR, real time PCR and the appropriate positive and negative controls.

In those cases where the IHA marker expression levels have been previously determined, the kit may contain a computer disk comprising sequence information for the performance of comparative genetic analysis of the test sample sequence information with IHA marker expression profile sequence information stored in a computer database, thereby identifying those samples exhibiting IHA marker expression profiles associated with more favorable or less favorable risk of recurrent, aggressive disease.

Methods of Using Iron Homeostasis Associated Proteins as Targets for Development of Therapeutic Agents Since the proteins described herein have been associated with cancer progression, methods for identifying agents that modulate the activity of the genes and their encoded products should result in the generation of efficacious therapeutic agents for the treatment of a variety of malignant diseases.

The iron homeostasis associated proteins provided in the Tables herein, particularly ferroportin and hepcidin, contain regions which provide suitable targets for the rational design of therapeutic agents which modulate their activity. Small molecules, including peptides, antibodies or functional fragments thereof corresponding to these regions may be used to advantage in the design of therapeutic agents which effectively modulate the activity of the encoded proteins.

Molecular modeling should facilitate the identification of specific organic molecules with capacity to bind to the active site of these proteins based on conformation or key amino acid residues required for function. A combinatorial chemistry approach will be used to identify molecules with greatest activity and then iterations of these molecules will be developed for further cycles of screening. In certain embodiments, candidate agents can be screening from large libraries of synthetic or natural compounds. Such compound libraries are commercially available from a number of companies including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), Chem Div (San Diego, Calif.). The skilled person is aware of other sources and can readily purchase the same. Once therapeutically efficacious compounds are identified in the screening assays described herein, they can be formulated in to pharmaceutical compositions and utilized for the treatment of cancer, alone or in combination with agents typically used to treat cancer.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested. In another approach allosteric modulators of the proteins may be identified.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered iron homeostasis associated gene. These host cell lines or cells are defective at the polypeptide level. The host cell lines or cells are grown in the presence of drug compound. The rate of cellular proliferation and transformation of the host cells is measured to determine if the compound is capable of regulating the proliferation and transformation of the defective cells.

Another approach entails the use of phage display libraries engineered to express fragment of the polypeptides encoded by iron homeostasis associated genes on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of iron homeostasis associated protein encoding nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

Pharmaceuticals and Peptide Therapies

The elucidation of the role played by the iron homeostasis associated proteins described herein in cellular transformation facilitates the development of pharmaceutical compositions useful for treatment and diagnosis of cancer. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal and intratumor routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. Such agents can be administered alone or in combination with agents typically used to treat cancer.

The following materials and methods are provided to facilitate the practice of the present invention.

Cell Culture:

Human mammary epithelial (HME) cells were obtained from Lonza (Rockland, Me.). HME cells transduced with h-TERT, SV40 T antigen and high levels of H-ras are termed R5 cells in this report and were a generous gift from the laboratory of Dr. Robert Weinberg, Boston, Mass. (14). All cells were maintained at 37° C. in a humidified atmosphere containing 5% $CO_2$. Cells were maintained in Dulbecco's Minimal Essential (DMEM-F12) medium (Gibco/BRL [Grand Island, N.Y.]) supplemented with L-glutamine, 10 µg/ml insulin, 10 ng/ml human epidermal growth factor, and 0.5 µg/ml hydrocortisone for 24 hrs prior to harvest. MCF7 and MCF10A cell lines were obtained from the Wake Forest University Comprehensive Cancer Center Tissue Culture Core facility. SUM149 and SUM102 cell lines were a generous gift of Dr. I. Berquin, Wake Forest University School of Medicine. HepG2 and HeLa cells were obtained from the ATCC and grown in DMEM media. K562 (from ATCC) was cultured in RPMI-1640 medium. Hepcidin was obtained from Peptides International, dissolved in water, and added to cells at a final concentration of 300 or 700 nM. Cells were harvested after 6 hours of treatment.

Figure 8A:
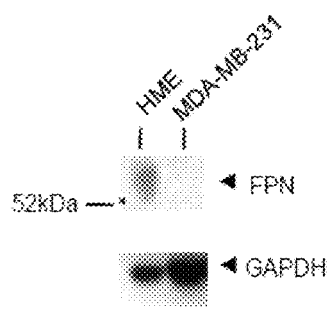
Figure 8B:
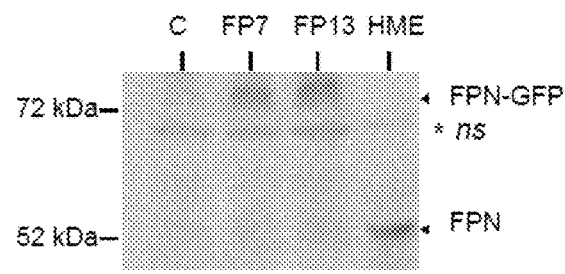
Figure 8C:
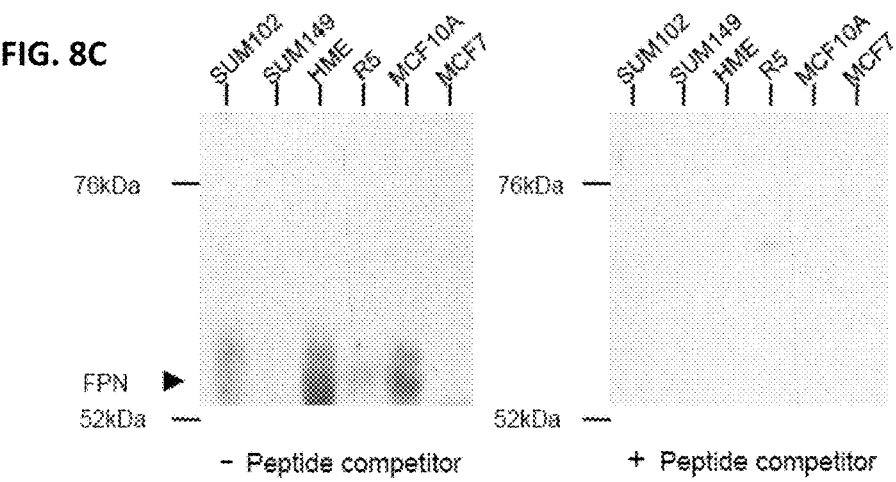
Figure 8D:
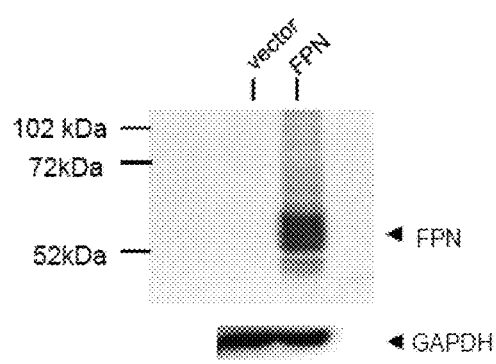

Western Blotting:

Cells were washed once in phosphate-buffered saline (PBS) and scraped. Whole cellular protein was extracted with NP-40 lysis buffer (25 mM Tris pH 7.4, 1% Triton X100, 1% SDS, 1% sodium deoxycholate, 150 mM NaCl, 2 µg/ml aprotinin, 1 mM PMSF) containing Complete protease inhibitor cocktail (Roche Diagnostics). Total protein concentrations were determined using BCA reagent (Pierce). Protein samples (10-50 µg) were separated on 12% gels (SDS-PAGE) and transferred on PVDF membrane (Millipore). Equal loading and transfer were confirmed by staining the membrane with Ponceau S, as well as incubation with anti-GAPDH antibody (Fitzgerald, Cat # RDI-TRK5G4-6C5, Concord, Mass.) followed by goat anti-mouse antibody (Bio-Rad, Cat #170-6516, Hercules, Calif.). Ferritin H was detected as previously described (49). Ferroportin was detected using anti-ferroportin-1 antibody (MTP-1, Alpha Diagnostics) followed by horseradish peroxidase conjugated goat anti-rabbit secondary antibody (Bio-Rad). Samples for ferroportin Western blotting were not heated or reduced. Specificity of the ferroportin band detected by the MTP-1 antibody was demonstrated by co-incubation with 5 µg/ml blocking peptide (MTP11-P, Alpha Diagnostics), which prevented binding (FIG. 8C), as well as by Western blotting following transient transfection of HeLa cells with a vector encoding wildtype (non-fusion) FPN (FIG. 8D). In one experiment (FIG. 8B), SLC40A1 antibody (ab58695-100, Abcam) was used in combination with MTP-1 antibody. Prohepcidin was detected using a rabbit polyclonal antibody (Hepcidin-25 antibody, ab75883, Abcam) followed by horseradish peroxidase conjugated goat anti-rabbit secondary antibody (Bio-Rad). Supersignal West Pico Chemiluminescent substrate was used for detection (Pierce).

Measurement of Ferroportin mRNA and Splice Variants—

Real time RT-PCR was performed to measure ferroportin mRNA level in different breast cell lines. PCR reaction was carried out on the ABI Prism 7000 sequence detection system (Applied Biosystems, Foster City, Calif.). The standard curve method was chosen for quantification. Total RNA was isolated using TRIzol reagent (Invitrogen), according to the manufacturer's instructions. 30 µg of RNA was treated with 40 units of DNase I (Promega) for 30 min at 37° C. RNA was then purified using a RNeasy Mini kit(Qiagen) following the manufacturer's protocol. Oligo(dT) primer was used in cDNA synthesis. Briefly, 800 ng of RNA was reverse transcribed in a total volume of 50 µl with a reverse transcription reagents kit (Applied Biosystems). To make a standard curve, serial dilutions of RNA from one sample were added to the RT reaction. Aliquots (3.5 µl) of cDNA were added to a 31.5-µl reaction mixture containing 17.5 µl of 2×SYBR® Green PCR Master Mix (Fermentas) and 400 nm primers. Absence of DNA contamination was confirmed by performing PCR from cDNA without reverse transcriptase. The primers for PCR were designed with IDT PrimerQuest software (Integrated DNA Technologies, Inc.); for ferroportin, forward, 5'-ACCTCGCTGGTGGTACA-GAATGTT-3' (SEQ ID NO: 1), and reverse, 5'AGCAG-GAAGTGAGAACCCATCCAT-3' (SEQ ID NO: 2); for GAPDH, forward, 5'-GAAGGTGAAGGTCGGAGTC-3' (SEQ ID NO: 3), and reverse, 5'-GAAGATGGT-GATGGGATTTC-3' (SEQ ID NO: 4). To determine whether multiple alternative transcripts of ferroportin are expressed in breast cells, PCR was performed using primers specific to each potential transcript variant. The cDNA used in PCR was same as above. PCR products after 38 amplification cycles were run on an agarose gel. The primers used in detecting the different splice variants of ferroportin are listed as below. For variant I: forward, 5'-AGGCTTTGCCTTTC-CAACTTCAGC-3' (SEQ ID NO: 5), and reverse, 5'-AACAGGAGTGCAAGGAACTGGAGA-3' (SEQ ID NO: 6). The predicted size of variant I PCR product is 171 bp. For variant IIA and variant IIB: forward, 5'-GTGTG-GCATCTGGTTGGAGTTTCA-3' (SEQ ID NO: 7), and reverse, 5'-AACAGGAGTGCAAGGAACTGGAGA-3' (SEQ ID NO: 8). The predicted size of variant IIA and variant IIB PCR product is 293 bp and 99 bp. For variant III: forward, 5'-CTTTGTCCTGGTGAGCACATCTGA-3' (SEQ ID NO: 9), and reverse, 5'-ATCCTCTCTGGCGGT-TGTGATCT-3' (SEQ ID NO: 10). The predicted size of variant III PCR product is 194 bp. To determine whether hepcidin mRNA is expressed in breast cancer cells, RT-PCR was performed and PCR products after 38 amplification cycles were run on an agrose gel. The primers used in PCR to detect hepcidin are: forward, 5'-CTGCAACCCCAG-GACAGAG-3' (SEQ ID NO: 11), and reverse, 5'-GGAATAAATAAGGAAGGGAGGGG-3' (SEQ ID NO: 12).

Tissue Array Staining:

Studies on human tissue specimens were conducted with approval from the Wake Forest University Health Sciences institutional review board. Construction of the breast tissue microarray (TMA) has been described previously (50). Briefly, hemotoxylin-eosin (H&E) sections of paraffin-embedded blocks were used to define tumor areas for core sampling. Two 1-mm cores from each patient were cut at multiple levels and placed into eight 60×10-mm TMAs by TriPath Imaging, Inc. (Burlington, N.C.). Slides were placed in a 100° C. oven for 20 min, cooled, de-paraffinized, and rehydrated through xylene and graded ethanol solutions to water. Antigen retrieval was performed using 0.05% citraconic anhydride (Aldrich) pH 6.1 for 1 hour at 98° C. Slides were treated with 100 µL of Dual Endogenous Enzyme Block (Dako) for 5 minutes and then rinsed with distilled water. The sections were then treated with 100 µL of a 1:50 dilution (20 µg/mL diluted in Dako antibody diluent) of MTP-1 (Ferroportin-1) antibody (Alpha Diagnostics, Intl.) for 30 minutes. Following a rinse with distilled water, 100 µL of EnVision™+ (Dual Link reagent) secondary antibody (Dako) was applied for 30 minutes and then rinsed. The antigen was visualized with 100 µL of diaminobenzidine chromogenic substrate (1 drop diluted in 1 mL of distilled water, Dako) for 10 minutes, rinsed, and counterstained with hematoxylin for 2 minutes. The negative control slides were treated in an identical manner except that the primary antibody was omitted. Semi-quantitative analysis of staining intensity was performed as previously described (50) by two independent blinded observers, with 0 representing low or undetectable staining; 1 representing intermediate staining; and 2 representing intense staining.

Labile Iron Pool Assay:

The cellular labile iron pool (LIP) was measured with the fluorescent metallosensor calcein, essentially as described (20). Calcein acetoxymethyl ester (CA-AM) was obtained from Molecular Probes (Eugene, Oreg.). The iron chelator, isonicotinoyl salicylaldehyde hydrazone (SIH) (a gift from Dr. P. Ponka, Lady Davis Institute for Medical Research, Montreal, Canada) was prepared as a 50 mM stock solution in dimethyl sulfoxide (DMSO). Briefly, 25,000-50,000 cells were cultured in 96-well plates in F12 medium supplemented with 10 ng/ml EGF, 10 µg/ml insulin, and 0.5 µg/ml hydrocortisone overnight. Cells were washed with phenol red-free DMEM, loaded with 1 to 2 µM CA-AM for 15 to 30 minutes at 37° C., then washed with PBS. 100 µM starch-conjugated desferrioxamine (DFO; a generous gift of Biomedical Frontiers, Inc., Minneapolis, Minn.) was added to cells to remove extracellular iron. Fluorescence was measured at 485 nm excitation and 535 nm emission with a fluorescence plate reader (fmax Fluorescence Microplate Reader, Molecular Devices). After the fluorescence signal was stabilized, SIH was added to remove iron from calcein, causing dequenching. The change in fluorescence following the addition of SIH ($\Delta F$) was used as a measure of the labile iron pool.

Transfection and Isolation of Ferroportin Expressing Breast Cancer Cells.

An expression vector encoding a functional ferroportin-GFP fusion protein was obtained as a generous gift from Dr. Jerry Kaplan (University of Utah) (8). The ferroportin-GFP cassette was amplified by PCR and subcloned into a lentiviral vector carrying a puromycin resistance marker (gift of Guangchao Sui, Wake Forest University Health Sciences). Plasmids were subsequently purified and sequenced. Lentivirus particles were produced by transient co-transfection of the FPN expression vector and packaging vectors (VSVG, pMDLG, and RSV-REV) into 293T cells (51, 52). Viral particles containing control empty vector were prepared similarly. Lentivirus was harvested after 48 hours and used to infect the MDA-MB-231-luc-D3H2LN human breast cancer cell line (Caliper Life Sciences, Hopkinton, Mass.). Cells were cultured in Eagle's Minimum Essential Medium supplemented with 10% fetal bovine serum, and 1% penicillin-streptomycin (all from Gibco/Invitrogen, Carlsbad, Calif.) at 37° C. in a humidified atmosphere containing 5% carbon dioxide. 8 hours after infection, 0.8 µg/ml puromycin was added to the medium and single clones selected. Stable clones were maintained in medium containing 0.4 µg/ml puromycin. Ferroportin expression in transfected cells was localized to the plasma membrane, as expected (not shown). For transient transfections, the ferroportin cDNA cassette without the GFP tag was amplified and cloned into the same lentiviral vector. Transfections were performed using Fugene 6 (Roche applied biosciences) and cells were harvested 24 hours after transfection.

Monitoring of Tumor Growth In Vivo.

Female athymic nude mice were purchased through the National Cancer Institute Animal Production Program (Frederick, Md.). Animals were housed in a pathogen-free facility with 12-h light/dark cycles and received a standard laboratory chow diet. All animal procedures were approved by the Wake Forest University School of Medicine Animal Care and Use Committee. Mice (approximately 10 weeks of age) were anesthetized by isoflurane inhalation (2% induction, 1-2% maintenance) and injected with 60 µl of 2×106 MDAMB-231-luc-D3H2LN-FPN cells or MDA-MB-231-luc-D3H2LN-vector cells suspended in 50% Matrigel/50% DPBS (Dulbecco's Phosphate Buffered Saline [(Invitrogen, Carlsbad, Calif., USA]) into the 4th inguinal mammary fat pad. The rate of tumor "take" (successfully implanted tumors) ranged from approximately 70 to 90%. Tumor growth was monitored weekly by bioluminescent imaging in a subset of animals. Bioluminescent imaging was performed with a cooled CCD camera mounted in a light-tight specimen box (IVIS™; Caliper Life Sciences). Before imaging, animals were given the substrate D-luciferin by intraperitoneal injection at 300 mg/kg in DPBS, and anesthetized (1-3% isoflurane) in a plastic induction chamber. Mice were then placed onto the warmed stage inside the light-tight camera box with continuous exposure to 1-2% isoflurane. Images were acquired between 10-20 minutes post-luciferin administration, and were imaged at 1 min, 8 bin, and 20 cm field of view, for a series of 8 images at 2 minute intervals. Generally, four to five mice were imaged at a time. Light emitted from the bioluminescent tumors was detected by the IVIS™ camera system, integrated, digitized, and displayed. Imaging and quantification of signals were controlled by the acquisition and analysis software Living Image® (Caliper Life Sciences). Regions of interest from displayed images were identified around the tumor sites and were quantified as total flux or photons/second using Living Image® software (Caliper Life Sciences). Background bioluminescence was in the region $1-2\times10^5$ photons/second. Tumors were excised and weighed at the termination of the study.

Ferrroportin-1 Immunohistochemistry.

Tissue was obtained as surgical biopsy specimen from a 78 year old female diagnosed with invasive ductal carcinoma. Antigen retrieval was performed on paraffin-embedded tissue using 0.05% citraconic anhydride (Aldrich, Milwaukee, Wis.) pH 6.1 for 1 hour at 98° C. Slides were treated with 100 μL of Dual Endogenous Enzyme Block (Dako, Carpinteria, Calif.) for 5 minutes, rinsed with distilled water, and then incubated with 100 μL of 20 ug/mL of anti-MTP-1 (Ferroportin-1) antibody (Alpha Diagnostics, Intl., San Antonio, Tex.) for 30 minutes. Following a rinse with distilled water, 100 μL of EnVision™+ (Dual Link reagent) secondary antibody (Dako) was applied for 30 minutes and then rinsed. The antigen was visualized following incubation with diaminobenzidine chromogenic substrate (Dako) diluted according to the manufacturer's instructions for 10 minutes. Slides were counterstained with hematoxylin. The negative control slides were treated in an identical manner except that the primary antibody was omitted.

Microarray Datasets.

Correlations between ferroportin expression in primary breast tumors and metastatic recurrence in patients were assessed using gene expression profiles from publicly accessible microarray datasets: (1) the Norway/Stanford study (23) (genomewww.stanford.edu/breast_cancer/mopo_clinical/data.shtml); (2) the Netherlands Cancer Institute (NKI) study (24) (www.rii.com/publications/2002/nejm.html); (3) the Uppsala study (25) (Gene Expression Omnibus (GEO) accession GSE3494); and (4) the Stockholm study (21) (GEO accession GSE1456). For analyzing ferroportin and hepcidin interactions, two large combined multi-institutional cohorts were utilized. The first consists of 3 population-based cohorts totaling 504 breast cancer cases annotated for clinical follow-up: Uppsala (GSE3494)(25), Stockholm (21) (GSE1456), and Singapore (53, 54)(GSE4922). In this instance, each cohort represents an unselected population of patients exhibiting a diverse range of breast cancer phenotypes, and each was profiled on both the Affymetrix U133A and U133B microarray platforms. The ferroportin microarray probeset (233123_at) is found only on the U133B Genechip, while the hepcidin probeset (220491_at) is found exclusively on the U133A Genechip. This cohort allowed us to investigate the prognostic interaction between ferroportin and hepcidin in unselected patient populations. The second large combined cohort, unlike the first, consists exclusively of ER+ breast cancer cases (n=518) derived from both unselected and selected patient populations: Uppsala (GSE3494)(25), Stockholm (21) (GSE1456), Singapore (53, 54) (GSE4922), and Oxford (55) (GSE6532). The Oxford collection is a selected cohort comprised of only ER+ breast cancer cases treated by adjuvant tamoxifen monotherapy (55). The purpose of this combined cohort was to allow a subset analysis of ER+ breast cancer cases uniformly treated with adjuvant hormonal therapy without chemotherapy (n=276; FIG. 13B).

Statistical Analyses.

Statistical analyses were performed in the core biostatistical facility of the Comprehensive Cancer Center of WFU by a statistician (RD). The significance of LIP values in cancer and non-cancer cells was assessed using t-tests. The significance of ferroportin in breast cancer versus normal breast epithelial tissue was calculated using Fisher's exact test.

The significance of ferroportin in tumor growth was calculated using a 2-way repeated measures analysis of variance where group, time and the group by time interaction were included in the model.

The significance of ferroportin and/or hepcidin expression in 10-year distant metastasis-free survival was calculated by the Kaplan-Meier method. Cases of primary synchronous bilateral breast cancer were censored for event at date of last follow-up with disease-free diagnosis. For each breast cancer cohort, cases were stratified into two groups based on an indicator variable for above/below the mean ferroportin level. The log-rank test was then used to determine whether ferroportin (above/below the mean) was a significant predictor of time to event. To test the validity of the mean as a cutoff for ferroportin and hepcidin, we examined a range of expression level thresholds. Although in some studies we were able to identify cutoffs that provided slightly greater statistical associations with metastasis-free survival than the mean (such as the median or quartile partitioning), the associations were generally robust and comparable to that of the mean.

Cox proportional hazards regression models were used to examine the significance of ferroportin plus hepcidin expression in the presence of established prognostic factors used in current clinical practice: age, grade, tumor size, lymph-node status, and ER-status (HER2 levels by immunohistochemistry or fluorescent in situ hybridization were not reported in any of the published studies used in our analysis). The significance of ferroportin in breast cancer molecular subtypes was determined using a one-way analysis of variance (ANOVA) model to compare the five groups (Basal, ERBB2, LumA, LumB, and Normal), and found to be highly significant (p<0.0001). Pairwise comparisons were then made among groups using t-tests within the ANOVA framework.

The following examples are provided to illustrate certain embodiments of the invention. They are not intended to limit the invention in any way.

Example 1

Ferroportin and Hepcidin in Cancer Prognosis and Therapy

In accordance with the present invention, ferroportin has been identified as both a pivotal protein in breast biology and a strong and independent predictor of prognosis in breast cancer patients. This finding provides the clinician with guidance as to which treatment protocol to pursue.

Ferroportin is Decreased in Breast Cancer Epithelial Cells Compared to Breast Cells with Limited or No Malignant Potential.

To explore whether ferroportin is present in normal human breast epithelial cells and whether its levels are altered in breast cancer, we compared ferroportin protein levels in three breast cell types with no or low malignant potential to their more malignant counterparts: (1) primary normal human mammary epithelial cells (HME) and tumor-forming variants of these cells derived by sequential transformation of HME cells with the catalytic subunit of telomerase, SV40 T antigen, and high levels of oncogenic H-ras (14) (termed R5 cells in this manuscript); (2) MCF10A cells, spontaneously immortalized diploid cells obtained from reduction mammoplasty (15) and MCF7(16), a breast cancer cell line established from a pleural effusion in a patient with metastatic breast cancer; (3) SUM102 cells, breast epithelial cells with a normal karyotype isolated from early stage breast cancer (17) and SUM149, a cell line developed from an aggressive inflammatory breast cancer (18). As seen in FIG. 1A, ferroportin protein levels were reduced in all aggressive breast cancer cell lines when compared to their counterparts with no or low malignant potential.

Ferroportin Reduction in Breast Cancer Cells is Associated with an Increase in Labile Iron.

Figure 1B:
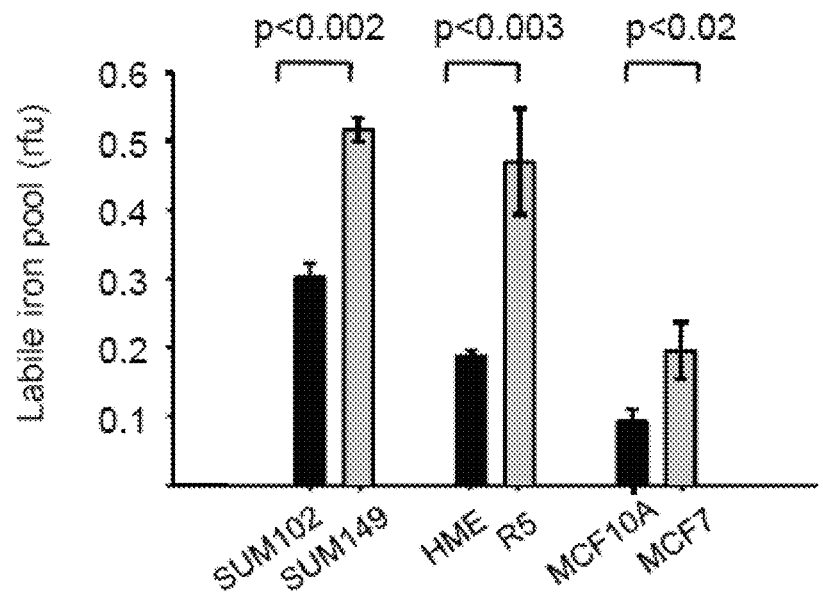
Figure 2:
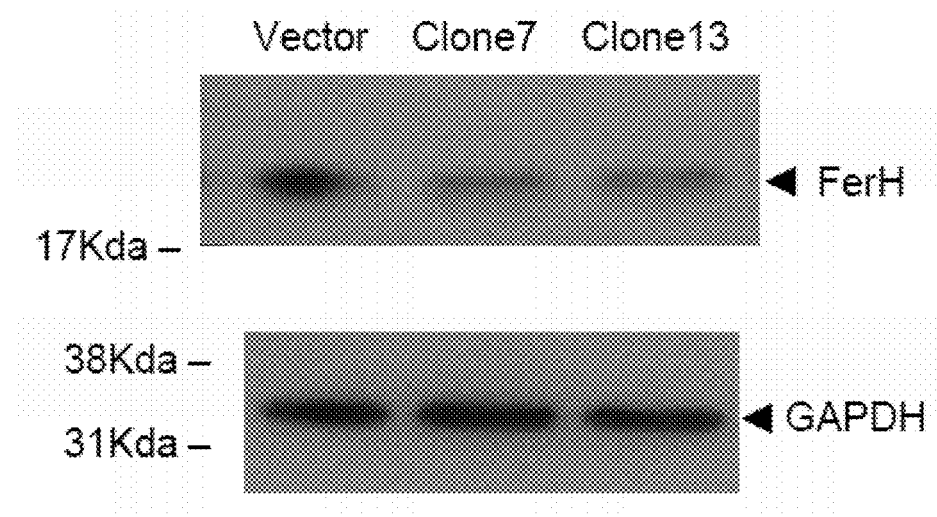
FIG. 2. Increased ferroportin expression decreases ferritin in breast cancer cells. MDA-MB-231 breast cancer cells were transfected with a vector encoding a functional ferroportin-GFP fusion protein (8). Two separate clones were analyzed by Western blotting using antibodies to ferritin H as described in Materials and Methods.

Cell growth is tightly linked to metabolically available iron, also termed the labile iron pool (LIP) (19). Multiple factors influence the LIP, including iron import and iron export (19). In particular, ferroportin-mediated iron efflux reduces levels of cellular iron, as measured by levels of ferritin (8). This pathway is preserved in breast cancer cells, since transfection of MDA-MB-231 breast cancer cells with a ferroportin expression vector similarly decreases ferritin (FIG. 2). Thus a decrease in ferroportin such as that observed in breast cancer cells might be expected to increase metabolically available iron. To test whether the decrease in ferroportin that we observed in breast cancer cells was associated with an increase in labile iron, we directly measured the LIP in normal breast epithelial cells and fully transformed breast cancer cells. As shown in FIG. 1B, the low levels of ferroportin protein expressed in breast cancer cells were indeed associated with higher levels of the LIP, suggesting that variations in ferroportin expression have functional consequences in cellular iron homeostasis.

Hepcidin is Expressed and Regulates Ferroportin in Breast Cells.

Figure 3A:
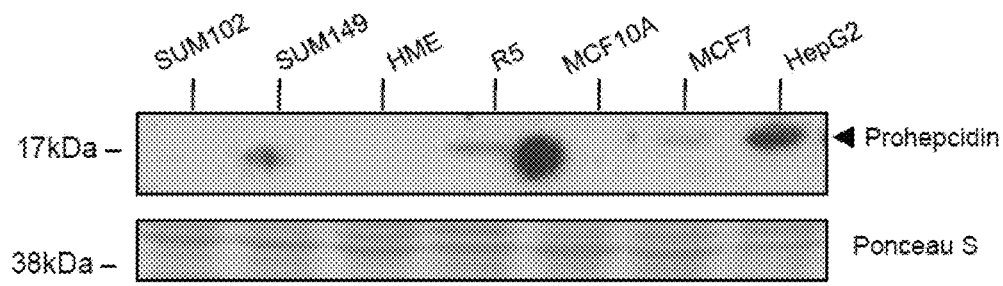
FIG. 3A-FIG. 3D. Hepcidin is expressed and regulates ferroportin in breast cells.
Figure 3B:
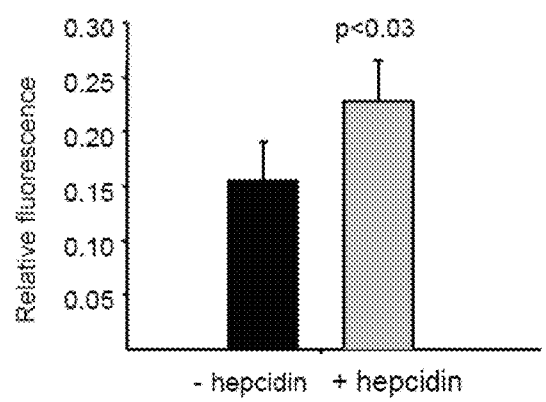
Figure 3C:
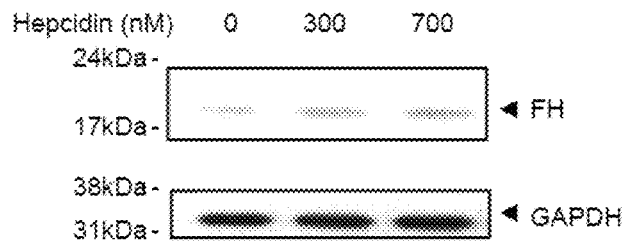
Figure 3D:
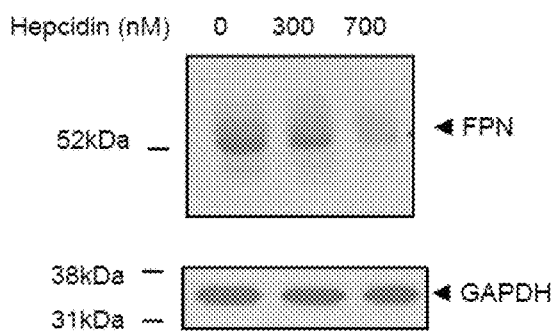
Figure 4A:
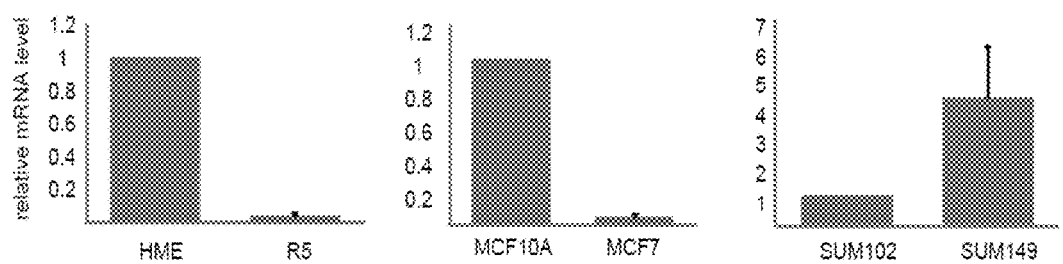
FIG. 4A-FIG. 4B. Ferroportin mRNA and splice variants in breast epithelial cells.
Figure 4B:
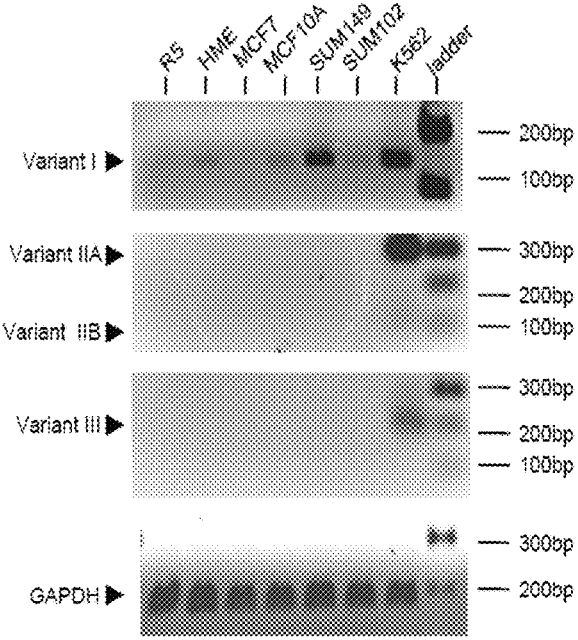
Figure 6:
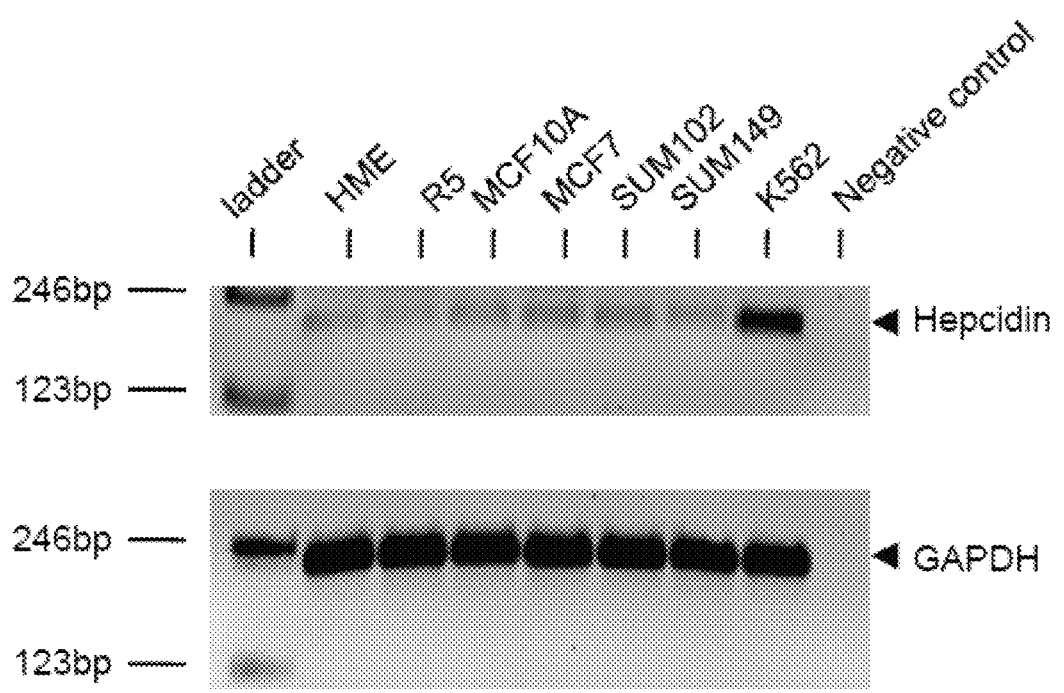
FIG. 6. Assessment of hepcidin mRNA in breast cells by RT-PCR.

To assess mechanisms underlying the reduction in ferroportin in breast cancer cells, we performed RT-PCR analysis of ferroportin mRNA. Consistent with Western blot analysis, ferroportin levels were lower in malignant R5 and MCF7 cells when compared to non-malignant HME and MCF10A cells (FIG. 4A). However, ferroportin mRNA levels were lower in non-malignant SUM102 cells when compared to SUM149 breast cancer cells (FIG. 4A). No ferroportin splice variants were detected (FIG. 4B). These results suggested that non-transcriptional mechanisms might also contribute to observed ferroportin protein levels. In addition to transcriptional regulation, ferroportin is post-translationally regulated by hepcidin-mediated degradation of the ferroportin protein. This regulatory axis has been elucidated in cell types responsible for control of systemic iron, such as the enterocyte, macrophage and hepatocyte (13). To test whether hepcidin was produced by breast epithelial cells and whether this mechanism of post-transcriptional control might contribute to regulation of ferroportin protein levels in breast cells, we used RT-PCR and Western blotting to measure levels of prohepcidin mRNA and protein in breast cells. As shown in FIG. 3A and FIG. 6, prohepcidin mRNA and protein were detectable in normal breast epithelial cells and in all cancer cell lines tested. Notably, levels of prohepcidin protein were higher in all breast cancer cells when compared to non-malignant breast cells (FIG. 3A). As has previously been observed in other cell types (8), hepcidin-mediated degradation of ferroportin was associated with increased labile iron and an increase in ferritin in breast cells (FIG. 3B,C). Since ferroportin expressed in breast epithelial cells can be degraded in response to treatment with exogenous hepcidin (FIG. 3D), these results suggest that both transcriptional and post-transcriptional mechanisms contribute to the decrease in ferroportin levels in breast cancer cells when compared to their non-malignant counterparts.

Increased Levels of Ferroportin Reduce Breast Tumor Growth in Mice.

Figure 5A:
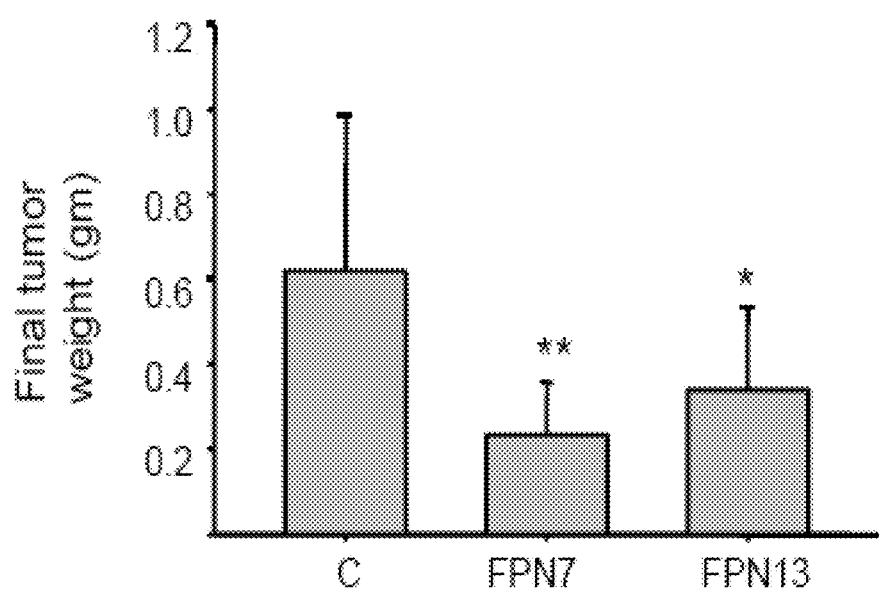
FIG. 5A-FIG. 5C. Increased levels of ferroportin decrease growth of breast cancer xenografts.
Figure 5B:
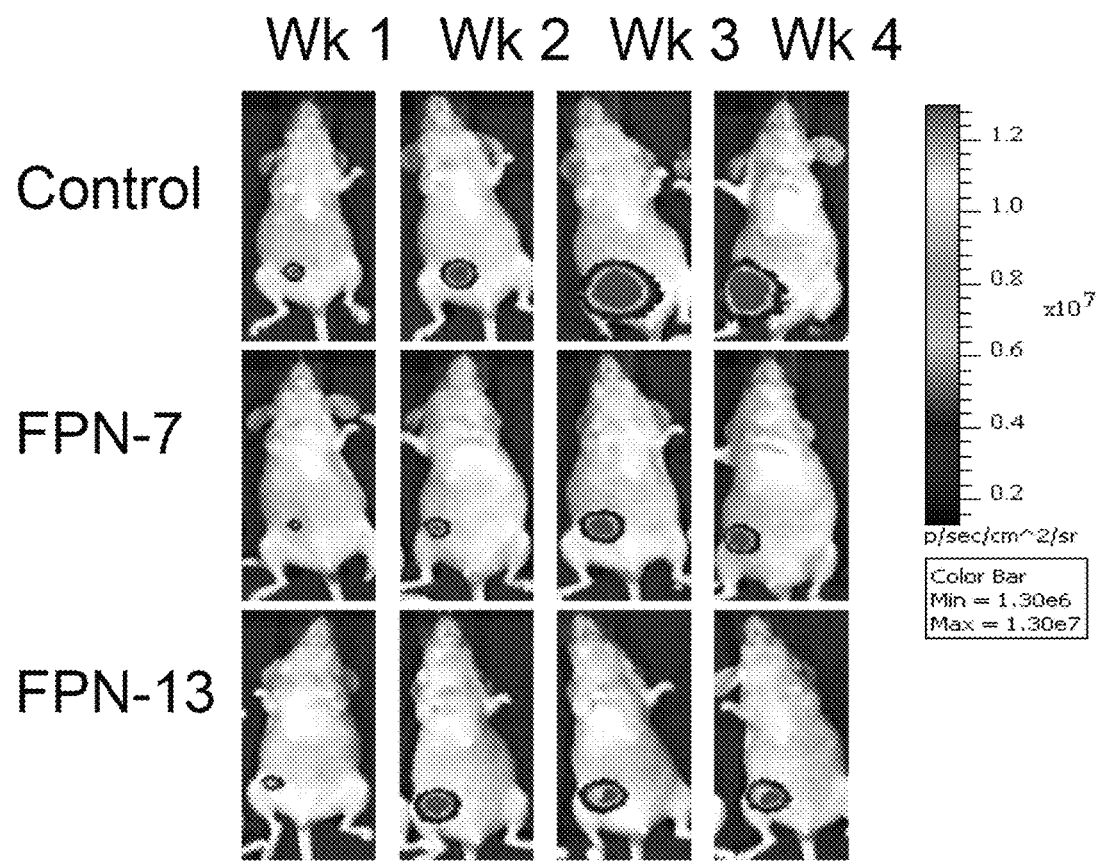
Figure 5C:
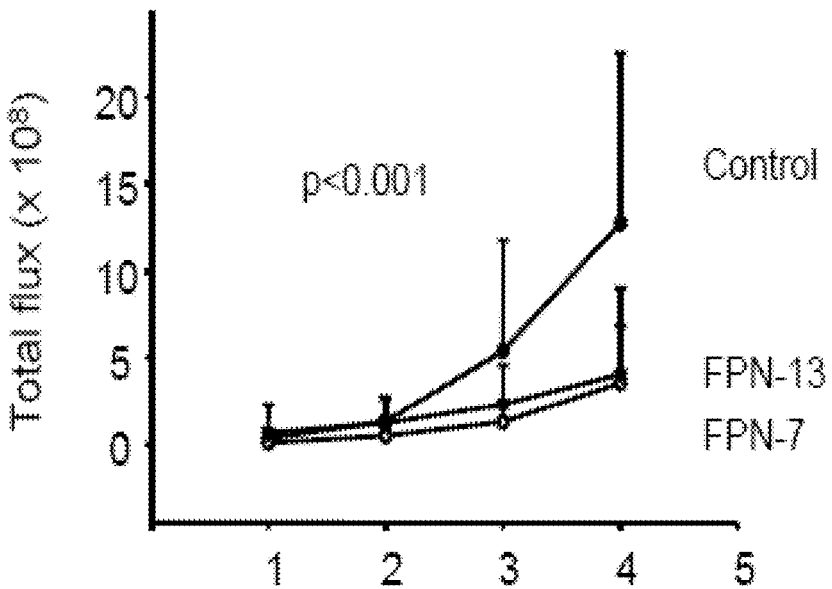

To explore the mechanism by which ferroportin affects the behavior of breast cancer cells in vivo, and to address whether alterations in ferroportin drive or simply correlate with a more aggressive breast cancer phenotype, we transfected human MDA-MB-231-luc cells, which express low levels of ferroportin (FIG. 8A), with an expression vector for ferroportin or with a control empty vector. Stable clonal transfectants were isolated. Transfection restored ferroportin protein levels to levels somewhat greater than those seen in non-malignant human mammary epithelial cells (FIG. 8B). Female nude mice were injected orthotopically in the mammary fat pad with control or transfected cells, and tumor growth was monitored. As shown in FIG. 5A, expression of ferroportin decreased final tumor weights as well as the rate of tumor growth (FIGS. 5B and 5C). Thus, ferroportin overexpression reduces growth of breast cancer in vivo.

Ferroportin is Decreased in Breast Cancer Tissue.

Figure 7A:
Figure 7B:
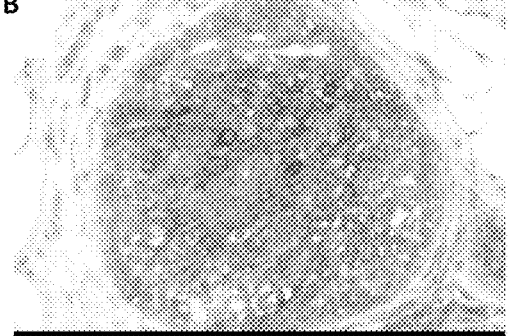
Figure 7C:
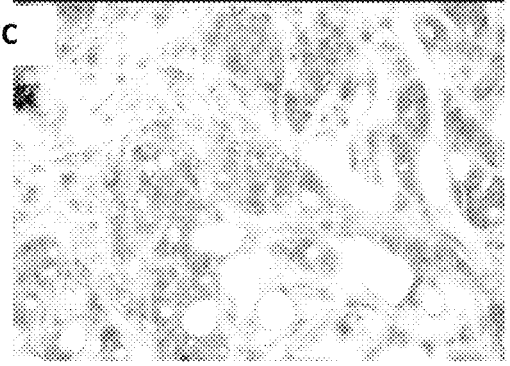

To test whether ferroportin levels were also modulated in the tissue of breast cancer patients, we performed immunohistochemical staining. FIGS. 7A-7C show a representative image of tissue derived from a single patient that contains areas of normal epithelium (A), ductal carcinoma in situ (B), and invasive breast cancer (C) within the same section. The intensity of staining decreases with increasing malignant potential, with highest expression in normal ductal structures and lowest expression in invasive tissue. Immunohistochemical staining of tissue from an additional 4 patients revealed a similar trend (FIG. 10).

Figure 7D:
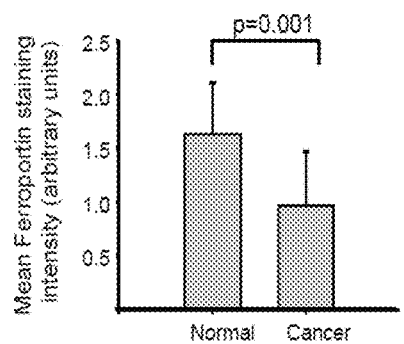
Figure 7E:
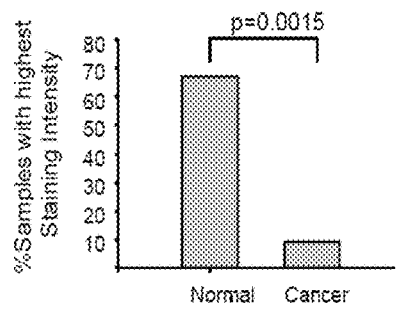

To confirm the generality of the decrease in ferroportin expression in human breast cancer, tissue microarrays containing 154 samples of breast tissue from breast cancer patients and 6 samples from normal breast were stained with anti-ferroportin antibody and scored semi-quantitatively by two independent blinded observers on a scale of 0-2, with 0 representing low or undetectable staining and 2 representing intense staining. As shown in FIG. 7D, the overall intensity of staining in the normal samples was higher than that of the cancer samples (1.63±0.5 as compared to 0.96±0.5 in the cancer samples (mean±S.D., p=0.001). Even more strikingly, 70% of normal samples received the highest staining intensity score, whereas only 9% of the cancer samples received this score (p=0.0015, Fisher's exact test) (FIG. 7E).

Figure 7F:
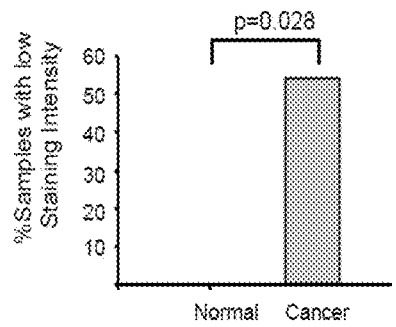

Conversely, staining in 52% of the cancer samples scored less than 1.0; this low level of staining intensity was seen in none of the normal samples (p=0.028, Fisher's Exact Test) (FIG. 7F). Thus, ferroportin protein levels are reduced in human breast cancer tissue as well as in breast cancer cell lines.

Breast Cancer Molecular Subtypes Differ in Ferroportin Expression.

Figure 9A:
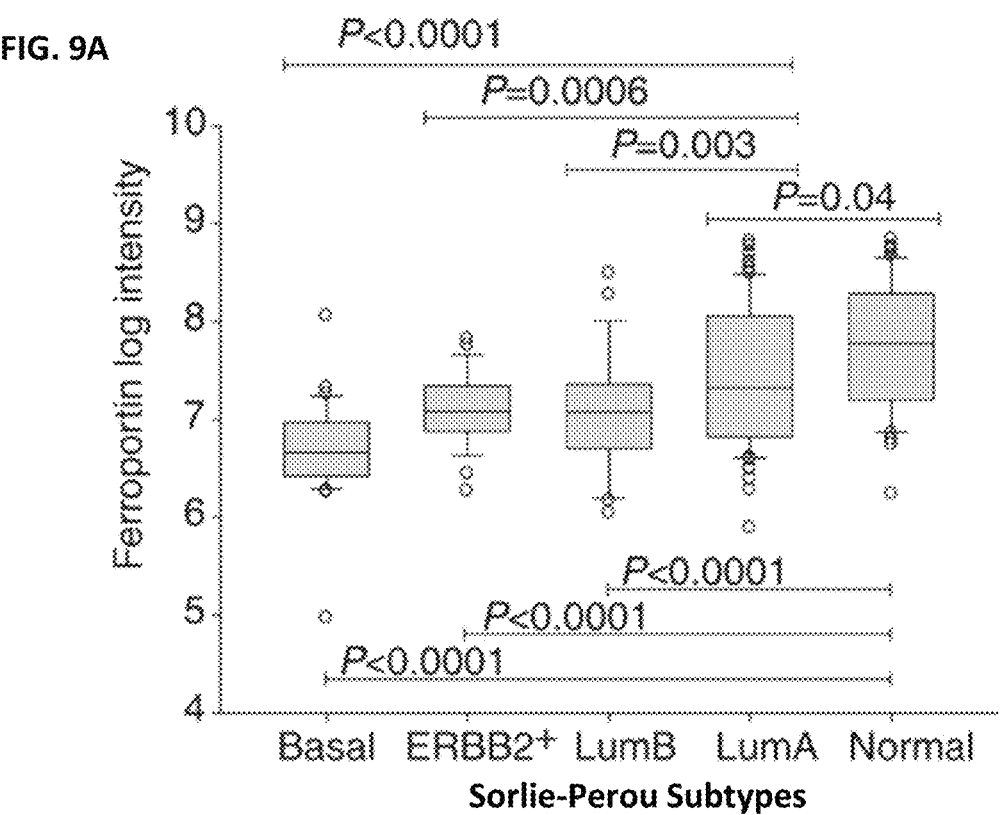
Figure 9B:
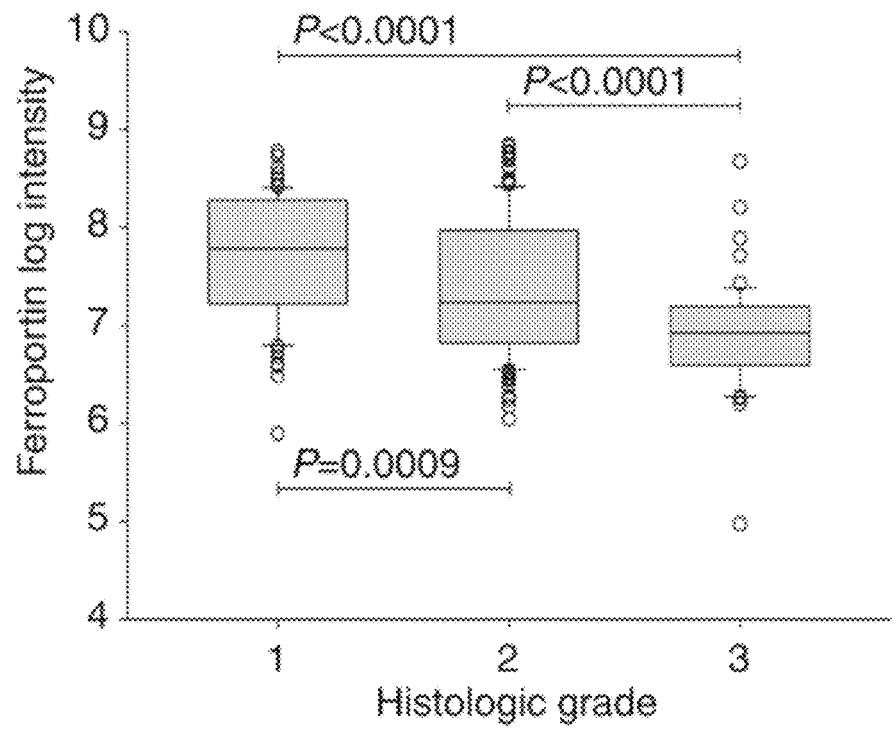
Figure 9C:
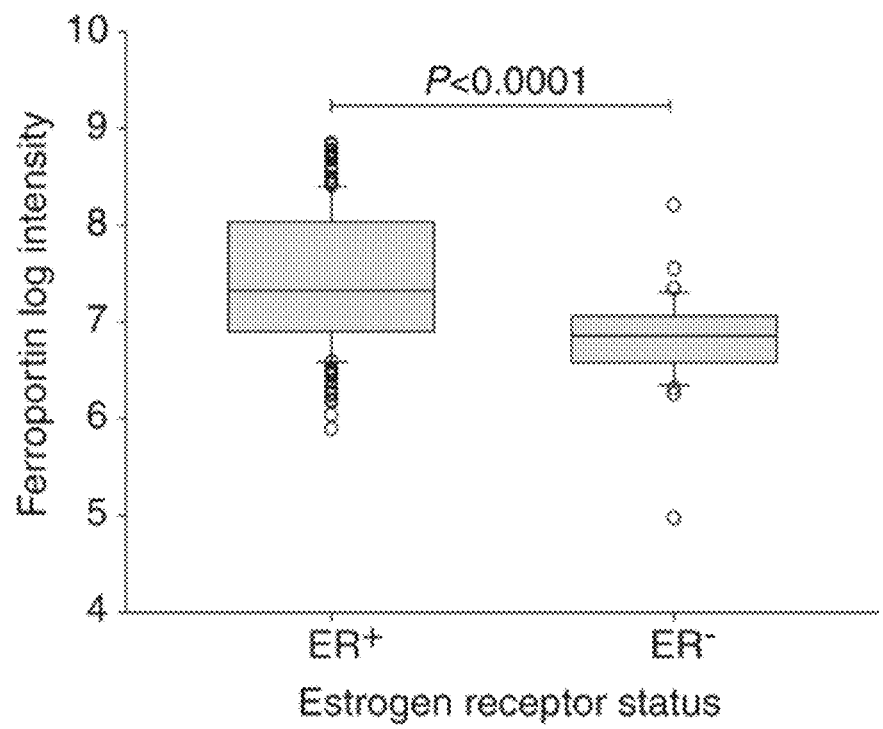
Figure 9D:
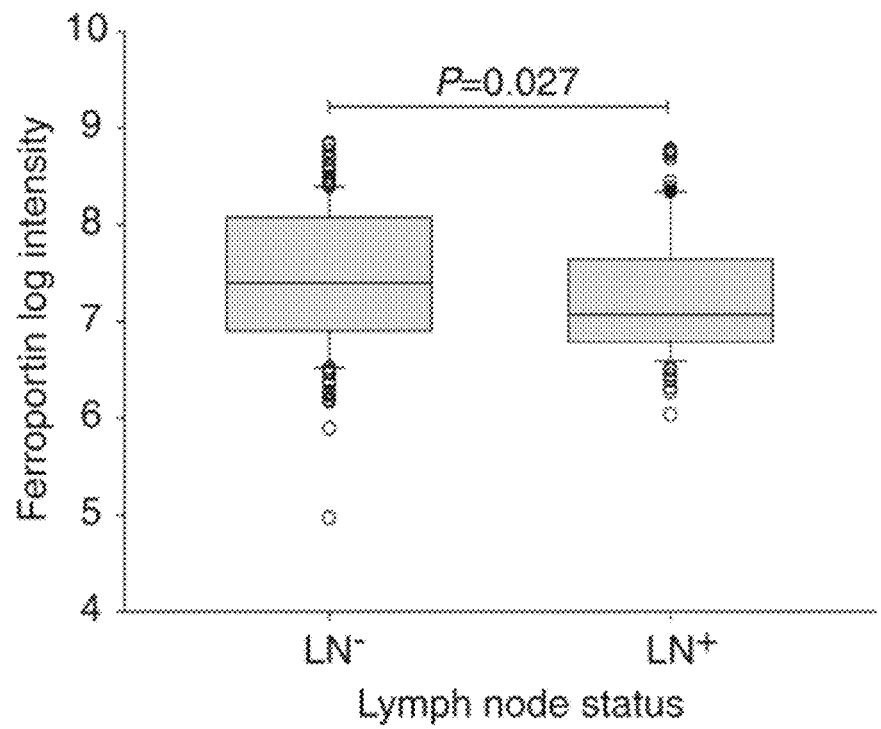

Using hierarchical clustering of microarray expression data, Sorlie et al. (20) classified breast cancers into molecular subtypes with significant outcome differences: normal, luminal A, ERBB2+, luminal B, and basal. We tested whether these breast cancer subtypes differed in ferroportin gene expression. Tumors in a cohort of 251 consecutive breast cancer patients from Uppsala, Sweden (21) were assigned molecular subtypes (22) according to computed correlations with subtype centroids. As shown in FIG. 9A, lower ferroportin expression was observed in the basal, LumB and ERBB2+ subtypes (poorer prognosis), and higher expression was seen in the normal and LumA subtypes (better prognosis). Differences between expression of ferroportin in subtypes with good prognosis (normal and LumA) and subtypes with poorer prognosis (ERBB2+, LumB, basal) were all statistically significant (FIG. 9A). Low ferroportin was also significantly associated with classical prognostic indicators of poor outcome, including high histologic grade (p<0.0009), absence of estrogen receptor (p<0.0001), and spread of disease to lymph nodes (p<0.027) (FIG. 9B-D). Thus, lower ferroportin gene expression is associated with poor prognosis molecular and clinical subtypes.

Ferroportin Expression Predicts Clinical Outcome in Breast Cancer.

The remarkably consistent decrease in ferroportin protein levels in malignant breast tissue and the association of decreased ferroportin gene expression with molecular subtypes of breast cancer with poor prognosis led us to ask whether ferroportin levels were related to breast cancer outcome. To perform this analysis, we leveraged four large patient cohorts with accompanying gene expression profiling data from studies of breast cancer patients with extensive clinical follow-up. These represent four of the largest datasets in the public domain for which microarray profiles as well as long-term patient outcomes are available: (1) 103 patients from the Norway/Stanford study of response to chemotherapy of locally advanced cancer (23); (2) 295 consecutive breast cancer patients from the Netherlands Cancer Institute (NKI)(24); (3) 251 consecutive breast cancer patients from Uppsala, Sweden (25); and (4) 159 surgically resected breast cancer patients from the Karolinska Institute in Stockholm Sweden (21). Patient outcomes measured in these studies were either disease-specific survival (death due to breast cancer) or distant metastasis-free survival (recurrence of cancer at a distant organ site). In each study, we calculated a mean level of ferroportin gene expression. Patient samples with levels of ferroportin expression at or above this cutoff were classified as high expressors, and those below were classified as low expressors. Distant metastasis-free survival (DMFS) or disease-specific survival (DSS) of high versus low ferroportin expressors was analyzed using Kaplan-Meier survival analysis.

As seen in FIG. 11A-D, in all four studies, low ferroportin gene expression was associated with a statistically significant and clinically substantial reduction in metastasis-free survival (p value from log rank test=0.003 (Norway/Stanford); 0.0006 (NKI); 0.036 (Uppsala); 0.007 (Stockholm). The most dramatic effect was seen for the Norway/Stanford study, where the 4-year disease-free survival rates were separated by over 30% (77% for those with high ferroportin compared to 43% for those with low ferroportin). The other three studies showed comparable metastasis-free survival benefits for high ferroportin (89% vs 65% for NKI; 90% vs 76% for Uppsala; and 91% vs 79% for Stockholm).

Hepcidin Expression Provides Incremental Predictive Value to Measures of Ferroportin in Breast Cancer Patients.

Hepcidin-mediated post-translational modulation of ferroportin activity is not directly assessable through gene expression analysis. However, because protein-level inhibition of ferroportin is linked to high mRNA expression of hepcidin (26), and hepcidin is expressed in breast cells (FIGS. 3 and 6), we examined the relationship between hepcidin gene expression, ferroportin gene expression, and disease outcome in breast cancer patients. We selected for this analysis a combined population-based (unselected) cohort in which all patients (n=504) had been studied using a microarray platform containing probesets for both ferroportin and hepcidin (Affymetrix U133A/B). This included the Uppsala and Stockholm cohorts analyzed in FIG. 11 and an additional cohort from Singapore (see Materials and Methods). This dataset was used because not all the datasets we previously analyzed for ferroportin included information on hepcidin expression. As seen in FIG. 12, signal intensity for hepcidin was substantially above the negative control and roughly comparable to that of other genes with roles in breast cancer, such as HER2/neu, ER alpha, VEGF, BRCA1 and Ki-67, confirming the expression of hepcidin in breast tumor tissue.

As shown in FIG. 13 (panels 1 and 2), ferroportin remains highly significant in this combined cohort (P=0.0004). Breast tumor hepcidin mRNA is of borderline significance as a prognostic marker by itself (P=0.06). However, in the presence of high ferroportin (FIG. 13A, panel 3), hepcidin expression confers highly statistically significant prognostic resolution (P=0.001), with the combination of low hepcidin and high ferroportin having 95% 5-year and 91% 10-year distant metastasis-free survival. Conversely, high ferroportin together with high hepcidin gene expression identifies a patient population with poor prognosis comparable to that of low ferroportin. As predicted from the iron biology, in the presence of low ferroportin (FIG. 13A, panel 4), differential hepcidin expression adds no additional prognostic value (P=0.73), (i.e., if little to no ferroportin is made, its post-translational regulation should have little prognostic consequence).

To further assess the prognostic value of ferroportin plus hepcidin gene expression, we used step-wise Cox proportional hazards regression to determine whether ferroportin plus hepcidin expression is an independent predictor of metastasis-free survival after allowing for other conventional prognostic variables (lymph node status, tumor size, grade, age, ER status) to be considered as covariates. As shown in Table V, high ferroportin, low hepcidin remained a significant and independent predictor of metastasis-free survival even in the presence of other traditional risk factors (p=0.003). These results indicate that assessment of ferroportin and hepcidin expression provides additional prognostic power beyond that which can be obtained with conventional clinical prognostic factors.

TABLE V

Ferroportin predicts outcome in multivariate analysis

| Variable | p-value |
| --- | --- |
| Hi FP/Low HAMP | 0.003 |
| Age | 0.312 |
| Size | 0.043 |
| Grade | 0.018 |

TABLE V-continued

Ferroportin predicts outcome in multivariate analysis

| Variable | p-value |
|---|---|
| ER status | 0.660 |
| LN status | 0.001 |

Given the ability of combined ferroportin plus hepcidin mRNA expression to identify a population of breast cancer patients with a 10-year metastasis-free survival rate of >90%, we sought to further define a clinical context in which this interaction might be useful in therapeutic decision making. ER+ breast cancer is one such context, because identifying patients who benefit from tamoxifen alone versus those who will require more aggressive combined tamoxifen+chemotherapy remains a considerable prognostic challenge. Thus, we assembled a curated collection of ER+ breast tumor expression profiles for which treatment/outcome data and microarray expression measurements inclusive of ferroportin and hepcidin were publicly available. From this collection of 518 patients (see Methods) we selected a subgroup of 276 who had all received similar therapy (adjuvant tamoxifen monotherapy). Forty-one percent of the patients in this group were lymph node positive. As shown in FIG. 13B, the high ferroportin-low hepcidin expressors (n=76) demonstrated a significantly better metastasis-free survival rate (93% at 5 years, 89% at 10 years; P=0.0005) as compared to the remaining population (76% at 5 years, 65% at 10 years).

As described above, we have demonstrated the importance of two iron regulatory proteins, ferroportin and hepcidin, in breast cancer. We showed that FP expression is reduced in breast cancer cells. We also showed that FP and its regulator HAMP are strongly correlated with breast cancer survival. Tumors with high levels of FP and low levels of HAMP have significantly improved distant metastasis free survival (DMFS).

Our studies have revealed additional IHA proteins whose expression levels can be correlated with breast cancer outcomes. These include, dCytB, TFR, and LTF. The discovery that FP and HAMP are highly correlated with breast cancer survival prompted us to investigate the impact of other genes involved in iron metabolism on breast cancer outcomes. We assembled a group of 46 genes based on the iron network devised by Hower et al. Tumors were randomly divided into training and testing groups limiting our analysis to those tumors with at least 5 years of survival data. Using BRB array tools, Cox-regression analysis was performed and genes correlated with survival were identified. The genes most significantly correlated with survival were duodenal cytochrome B reductase (dCytB), lactotransferrin (LTF) and transferrin receptor (TFR). Consistent with the results presented above, FP was also highly correlated with survival, and HAMP was only significant in the context of FP expression.

High Expression of dCytB, High Expression of LTF, and Low Expression of TFR1 are Each Correlated with Increased Survival Since we identified these iron genes using different microarray data than previously used in Torti et al., we first confirmed the previously defined associated between FP and HAMP in breast cancer. Using expression levels divided on the mean, tumors were separated based on FP and HAMP expression, and the association with survival examined. As seen in FIG. 13, tumors with high FP expression and low HAMP expression had a significantly higher 10-year DMFS when compared to tumors with alternate FP/HAMP expression profiles. This supports our previous study and increases evidence that high FP and low HAMP expression is associated with improved survival in breast cancer.

We then focused on the genes newly identified by Cox-regression analysis as significantly correlated with survival. dCytB is a newly identified gene associated with iron metabolism. It is a ferric reductase primarily expressed in duodenal enterocytes and plays a role in reducing iron to facilitate iron uptake into the enterocyte. Transferrin receptor is a well known transmembrane receptor that binds transferrin and facilitates the import of iron into cells. Transferrin receptor levels are regulated by intracellular iron levels—decreased intracellular iron leads to an increase in TFR expression. Lactotransferrin is a secreted iron binding protein which stores extracellular iron and thereby prevents iron usage by microorganisms and other pathogens. Increased levels of lactotransferrin lead to a decrease in the amount of free or usable iron. Expression levels of these genes were robust and comparable to other genes important in breast cells, such as ER alpha, and Ki67.

We examined each of these genes individually to determine in what way expression influenced survival. Tumors were divided into high or low expression based on mean expression level (high expression was defined as equal to or above the mean, low expression was defined as below the mean). FIG. 14A shows Kaplan-Myer survival curves of patients with tumors in the high and low dCytB expression groups. High expression of dCytB was significantly associated with increased 10-year DMFS (84% DMFS in the high expression group, 66% DMFS in the low expression group, p<0.001). This indicates that the expression of dCytB conveys a survival advantage, while low levels are correlated with poor survival. We then examined the effect of lactotransferrin expression on survival using a similar strategy. As shown in FIG. 14B, high expression of LTF was associated with a significant increase in 10-year DMFS (80%) as compared with the low LTF expression group (68%), p<0.001. This demonstrates that high levels of LTF are also linked to good breast cancer outcomes. Finally we tested the association between transferrin receptor and survival. In opposition to dCytB and LTF, low levels of TFR are associated with good survival while high levels of TFR are associated with poorer survival. The low TFR expression group had a 10-year DMFS of 79% while the high TFR expression group had a 10-year DMFS of 70%, p=0.012.
Combined Analysis of dCytB, LTR, and TFR Provides Incremental Information in Defining Favorable Vs Poor Survival Groups Since each of these genes was independently associated with survival, we tested whether the combined analysis of all three genes would convey additional prognostic information. Since dCytB and LTF expression are positively correlated with survival and TFR is negatively correlated with survival, we divided the tumors into groups that demonstrated high dCYtB expression+high LTF expression+low TFR expression levels (based on mean expression levels of the individual genes) and low dCytB expression+low LTF expression+high TFR expression levels.

FIG. 14C demonstrates the result of this analysis. The combination of dCytB, LTF and TFR expression significantly differentiated good vs poor outcome breast cancer patients (p<0.001). 10-year DMFS in patients exhibiting the combination of high dCytB, high LFT and low TFR expression was 89%. This 10-year DMFS is greater than that seen in either the dCytB or LTF or TFR individual good outcome groups. Conversely, the combination of low dCytB, low LFT and high TFR expression produced a poor outcome group with a 10-year DMFS of 62%, which was worse than that seen in either the dCytB or LTF or TFR individual poor outcome groups. The combined analysis of all three genes provided a statistically significant advantage in differentiating good vs poor outcome patients when compared to analysis of each gene individually.

The FP/HAMP Gene Signature and dCytB, LTF and TFR Gene Signature Define Different Populations of Tumors These results identified two different iron gene expression profiles associated with good breast cancer survival: (1) high FP with low HAMP expression; and (2) high dCytB, high LTF and low TFR expression. We next asked whether these classifiers identified the same or different patients. For this analysis we compared the identity of all patients with "good" outcomes by either expression profile (i.e. those tumors contained either in the high FP with low HAMP expression group or in the high dCytB, high LTF, low TFR expression group, total n=317). As seen in FIG. 14D, only one third of the patients (n=69) exhibited both signatures. The remaining tumors were unique to either the high FP, low HAMP group (n=152) or the high dCytB, high LTF, low TFR group (n=96). Thus while there is some overlap in the tumors identified by the two different iron gene expression profiles, the majority are uniquely identified by each expression profile, suggesting that the expression profiles identify different groups of patients.

dCytB, LTF, TFR Expression is Able to Further Separate Tumors Initially Characterized by FP, HAMP Expression Because the two iron gene expression profiles were largely non-redundant, we asked whether they could be combined to provide additional prognostic information. Specifically, we queried whether we could use the dCytB/LTF/TFR signature to identify patients with good prognosis among those who had been classified as poor prognosis using the FP/HAMP gene signature. We selected all patients in the "poor" FP/HAMP group (defined as those that did not have high FP with low HAMP expression) and divided them according to their expression of dCytB, LTF and TFR. FIG. 14E shows the Kaplan-Myer survival curve of this "poor" FP/HAMP group divided into a "good" dCytB, LFT, TFR group (high dCytB, high LFT, low TFR expression) and a "poor" dCytB, LTF, TFR group (low dCytB, low LTF, high TFR expression). The good dCytB, LTF, TFR group demonstrated an excellent 10-year DMFS of 90% and the poor dCytB, LTF, TFR group demonstrated a 10-year DMFS of 61%. When this is compared to the survival of the group as a whole (10-year DMFS 70%), it is clear that applying the dCytB, LTF, TFR gene expression profile was able to identify a subpopulation of patients with excellent survival among those predicted to have poor survival based on FP/HAMP. Thus concomitant analysis of the dCytB/LTF/TFR gene expression profile significantly improves the ability of FP/HAMP gene expression profile to predict DMFS of breast cancer patients.

Characteristics of Tumors that Fall into Good and Poor Outcome Groups

Having identified two different iron gene expression profiles that predict DMFS of breast cancer patients, we next assessed the characteristics of patients that fall into these groups. We divided all patients into the following outcome groups: (1) patients with good FP/HAMP expression profile (high FP low HAMP expression); (2) patients with good dCytB/LTF/TFR expression profile (high dCytB, high LTF, low TFR expression); (3) patients that fall into both good expression profiles; (4) all remaining patients (poor outcome). The lymph node, ER status, grade, and therapy of these patient groups was then assessed. The lymph node status, estrogen receptor status, tumor grade and treatment type across all good outcome groups were very similar. All three groups with a favorable prognostic signature had a similar proportion of LN+ patients, ER+ patients, grade distribution and treatment. When compared to the entire population, the good outcome groups had a slightly higher proportion of LN+ and ER+ patients and a significantly larger proportion of grade 1 tumors. The poor outcome group had a slightly lower proportion of LN+ and ER+ patients and a significantly higher proportion of grade 3 tumors. The difference in tumor grade suggests that good iron gene expression profiles identify a group of tumors that are less aggressive while poor iron gene profiles identify a more aggressive group of tumors. Further, traditional markers associated with outcome such as LN status and ER status are only marginally different.

Genetic Signature Predictive of Low, Intermediate and High Risk of Metastasis.

To further characterize iron-related genes (ie, genes with functional roles in iron biology) that are prognostic of breast cancer patient outcomes, we studied the expression of approximately 50 iron-related genes in a large "super" microarray cohort of 759 primary breast tumors derived from 6 independent cohorts. The breast cancer cohorts comprising the super cohort and corresponding database accession numbers and references are shown in Table VI below.

TABLE VI

| Breast Cancer Dataset | GEO Database Acc# | PubMed Reference(s) | Cohort Size (# patients) | Cohort Characteristics |
|---|---|---|---|---|
| UPP(258) | GEO: GSE3494, GSE4922, GSE6532 | PMID: 16141321; PMID: 17079448; PMID: 17401012 | 258 | Population based |
| STO(159) | GEO: GSE1456 | PMID: 16280042 | 159 | Population based |
| OXFT(109) | GEO: GSE6532 | PMID: 17401012 | 109 | ER+, Tamoxifen monotherapy |
| OXF(69) | GEO: GSE6532 | PMID: 17401012 | 69 | LN−, untreated |
| GUYT(87) | GEO: GSE6532 | PMID: 17401012 | 87 | ER+, Tamoxifen monotherapy |
| GUYT2(77) | GEO: GSE9195 | PMID: 18498629 | 77 | ER+, Tamoxifen monotherapy |

All tumor samples were profiled on the Affymetrix U133A, U133B or U133 PLUS 2.0 series microarray Genechip platforms. Of 759 cases, 741 had corresponding survival data with distant metastasis-free survival (DMFS; ie, time to distant-metastasis or last follow-up without recurrence) as the clinical endpoint. Briefly, all microarray data were processed using the MAS5.0 algorithm (Affymetrix), scaled to a mean target signal intensity of 500, and $\log_2$ transformed. The expression data were then corrected for batch-related effects using Partek Genomic Suite batch correction software. The BRB ArrayTools gene expression analysis software was employed to identify genes with statistically significant associations with DMFS. Fourteen genes shown in the Table 1 were selected (based on their significant associations with DMFS, underlined in the Tables) for the purpose of developing a prognostic gene expression signature, eg, the "iron signature", for predicting DMFS of breast cancer patients. The "survival risk prediction algorithms" were used to generate a predictive model using these selected genes in a "training set" comprised of half of the tumor population (ie, 337 cases). The model was constructed in this training set (ie, thresholds for each gene and their predictive weights were defined), and the model was then applied to a "test" set (ie, also 337 cases) that was not previously involved in the training process. Three risk groups (low-risk, intermediate-risk, and high-risk) were defined in the training process, and these were based on the upper, middle and lower tertiles of the population defined by the algorithm's predicted probability for risk assignment. When applied to the test set, 3 distinct low, intermediate and high risk survival curves can be seen by Kaplan-Meier analysis. See FIG. 15. FIGS. 16-18 show Kaplan-Meier plots for low risk and high risk patients, for tamoxifen-treated, lymph node positive patients and tamoxifen-treated, lymph node negative patients respectively.

In both the training and test sets, the differences in risk group survival were statistically significant at p<0.001 (low-risk=green curve, intermediate-risk=blue curve, and high-risk=red curve). Thus the iron gene signature has a robust and reproducible prognostic performance, and can distinguish breast cancer patients with low, intermediate and high risk of future distant metastasis.

In the microarray studies used to discover the prognostic utility of these genes, RNA was purified from frozen samples of primary breast tumors and profiled on a DNA microarray. The skilled person is well aware of other methods for analyzing and quantitating gene transcript levels in a sample. RNA can be derived from a variety of sources, including, without limitation, fresh frozen issue, or formalin-fixed, paraffin-embedded (FFPE) tissue.

Six Gene Diagnostic Test

6-Gene Model: Fp+DcytB+STEAP1+STEAP2+ISCU+TFRC

| High Expression = Good Outcome | High Expression = Poor Outcome |
|---|---|
| SLC40A1; 223044_at<br>CYBRD1; 222453_at<br>STEAP1; 205542_at<br>STEAP2; 225871_at<br>ISCU; 209075_s_at<br>Above-mean expression coded as "1", below-mean coded as "0" (mean based on 759 tumors) | TFRC; 240686_x_at<br>Below-mean expression coded as "1" above-mean coded as "0" (mean based on 759 tumors) |

Adding the 0s and 1s, each tumor was classified by the sum of the 6 genes, creating 7 classes: 6, 5, 4, 3, 2, 1, or 0.

Here, a different classification strategy was explored, and a prognostic model of DMFS was discovered among the iron regulatory genes that involved 6 genes only: Fp, DcytB (also known as CYBRD1), STEAP1, STEAP2, ISCU, and TFRC. This model is of particular interest as it is based on a jury voting method whereby each of the six genes casts an "outcome vote" based on a binary prediction of whether a tumor case should be assigned to the low risk (good outcome) or high risk (poor outcome) group. The vote of each gene is determined by: 1) whether the gene was expressed above or below the mean of the population (n=759 total cases), and 2) whether the gene expression level was associated with good outcome (ie, a "1") or poor outcome (ie, a "0"). Then, the scores assigned by all 6 genes are summed yielding 7 possible outcome classes: 0, 1, 2, 3, 4, 5 or 6. We found that the outcome classes exhibit a significant linear association with patient outcome that allow us to define 3 prognostic patient classes with potential clinical utility: low risk (excellent outcome, defined by sum=5 or 6), intermediate risk (intermediate outcome; defined by sum=4 or 3), and high risk (poor outcome, defined by sum=0, 1, or 2). See FIGS. 19 and 20.

IHA Marker Expression Levels can Also Predict Clinical Outcome in Ovarian Cancer Patients These Kaplan-Meier survival plots show that the expression levels of Feroportin (Fp; SLC40A1) are also positively correlated with survival of ovarian cancer patients. These data derive from a published microarray analysis from the Peter MacCallum Cancer Center (PMCC) in Melbourne, Australia. 274 primary ovarian tumors were profiled on the Affymetrix GeneChip microarray. Following the same procedure previously described for the breast cancer analysis, we divided ovarian cancer patients/tumors into 2 groups—above-mean Fp and below-mean Fp—and assessed their survival differences by KM analysis (See FIG. 21, left panel). The survival endpoint was disease-specific survival (DSS), where the endpoint was death due to ovarian cancer (coded as an event) or no death due to ovarian cancer at the time of last follow-up (coded as censored). Left panel of FIG. 21 shows that patients with tumors with below-mean expression of Fp (ie, "low" SLC40A1) have significantly worse DSS (p=0.001) than those with above-mean ("high") Fp. Shown in the right panel of FIG. 21 are the survival curves where patients/tumors were dichotomized to two groups based on the optimal Fp expression level. This level provides maximal separation of the survival curves (compared to the arbitrarily assigned "mean" threshold level, used in the left panel). These data indicate that, just as in breast cancer, the relative expression levels of Fp in ovarian cancer are prognostic of patient outcome.

Discussion

Iron is essential for normal cell function. Many cancers exhibit increased iron requirements, presumably due to the need for iron as a cofactor in proteins essential to sustain growth and proliferation (27-29). Misregulation of iron regulatory proteins affects growth of tumor xenografts (30), and agents that deplete iron are currently under investigation as anti-cancer therapies (31-34).

Iron availability can be regulated by increased uptake, a shift of iron from storage to active pools, or a reduction in cellular iron export. Several of these processes are known to be altered in cancer. For example, an increase in transferrin receptor 1, a cell surface receptor responsible for transferrin-mediated iron uptake, occurs in many cancers, including breast cancer (35-37). Ferritin, an iron storage protein, is decreased by the c-myc (38) and E1a (39) oncogenes; reduced ferritin is thought to shift iron from storage to labile, metabolically available compartments. Similarly, antisense-mediated repression of ferritin increases the labile iron pool (19) and stimulates H-ras-dependent proliferation (40). In principle, a decrease in iron export could also elevate labile iron and affect breast cancer phenotype and outcome. Indeed, ferroportin has been shown to be expressed in rat mammary epithelium (41). However, relatively little is known of iron export in cancer, primarily because the discovery of iron export proteins is quite recent.

We observed a striking reduction of ferroportin, the only known exporter of non-heme iron, in breast cancer compared to normal breast epithelium. This reduction of ferroportin protein occurs both in malignant breast cancer cell lines (FIG. 1A) and in breast cancer tissue, particularly in the more aggressive and invasive areas of the cancer (FIG. 7). The modulation in ferroportin was sufficient to alter the labile iron pool, a key arbiter of iron availability in cells (FIG. 1B) and to affect growth of tumor xenografts (FIG. 5). Classically, increases in iron trigger feedback loops that upregulate iron sequestration to maintain labile iron in a steady state (42). We hypothesize that in breast cancer cells, repression of ferroportin or up-regulation of hepcidin may occur as proximal events that drive changes in the labile iron pool and enable these cells to evade classic iron regulatory loops, although this hypothesis will require further study. Our results are in keeping with emerging evidence of the importance of ferroportin in iron homeostasis, both at an organismal level in transmitting the signals from hepcidin to the systemic iron regulatory network (43), and in regulating iron homeostasis in cells (8). These data also suggest that altered iron homeostasis may, at least in part, explain aggressive breast cancer behavior, although additional investigations will be needed to fully clarify the role of ferroportin and hepcidin in breast cancer biology.

Our data also indicate that ferroportin plays an important role in the clinical behavior of breast cancer (FIGS. 9, 11 and 13). Our results reveal that (1) ferroportin gene expression is a previously unrecognized determinant of outcome that in logistic regression analysis is independent of other prognostic factors; (2) ferroportin not only equals the best clinical predictors of outcome in breast cancer patients, but also tracks with recently identified molecular subtypes of breast cancer (20) that can add significant prognostic and predictive information to standard outcome parameters of breast cancer (44) (FIG. 9A); (3) the striking decrease in tumor growth in vivo of ferroportin-overexpressing breast cancer cells (FIG. 5) provides evidence that ferroportin expression is not simply a marker of poor prognosis in primary breast cancer, but contributes to a clinically aggressive phenotype; (4) the additive value of ferroportin and hepcidin gene expression provides further support for a critical role of iron homeostasis in breast cancer behavior.

Ferroportin+hepcidin gene expression identifies a clinical subset of breast cancer patients who should be evaluated in future studies to determine if they could be spared potentially toxic treatments. The excellent survival of patients with high ferroportin-low hepcidin gene expression seen in FIG. 13B is comparable to that of the ER+, node negative patients classified into the good outcome group by the Oncotype Dx 21-gene panel (45). The 2008 National Comprehensive Cancer Network practice guidelines recommend that these patients receive tamoxifen monotherapy. Analysis of ferroportin+hepcidin expression may provide additional power to discriminate good and poor outcome patients: using ferroportin+hepcidin gene expression, we were able to identify not only node negative ER+ but node positive ER+ breast cancer patients who exhibit this good outcome (41% of the high ferroportin-low hepcidin expressors in our study were node positive at diagnosis). Thus if confirmed in additional patient cohorts, ferroportin activity, as approximated by a 2-gene model of ferroportin and hepcidin transcript levels, may provide clinical utility as a treatment indicator for both node-negative and node-positive, ER+ cancer patients.

Ferroportin may also be important in other tumor types. Ferroportin was among the genes decreased in breast cancer samples in an in silico analysis of the Unigene database (46). Ferroportin was also 6-fold decreased in an analysis of global gene expression changes in human hepatocellular carcinoma (47). Our inspection of the Oncomine (48) database revealed that decreases in ferroportin are observed in prostate cancer and leukemia, although they are not observed in brain cancer, esophageal cancer or seminoma. The decrease in ferroportin is thus related to tumor type, perhaps reflecting differences in organ site-specific mechanisms of tumor development.

In additional studies we have identified IHA gene signature having robust and reproducible prognostic value which can be used to advantage to distinguish breast cancer patients with low, intermediate and high risk of future distant metastasis.

REFERENCES FOR EXAMPLE 1

1. S. Abboud, D. J. Haile, A novel mammalian iron-regulated protein involved in intracellular iron metabolism. *J Biol Chem* 275, 19906-19912 (2000).
2. A. T. McKie, P. Marciani, A. Rolfs, K. Brennan, K. Wehr, D. Barrow, S. Miret, A. Bomford, T. J. Peters, F. Farzaneh, M. A. Hediger, M. W. Hentze, R. J. Simpson, A novel duodenal iron-regulated transporter, IREG1, implicated in the basolateral transfer of iron to the circulation. *Mol Cell* 5, 299-309 (2000).
3. A. Donovan, A. Brownlie, Y. Zhou, J. Shepard, S. J. Pratt, J. Moynihan, B. H. Paw, A. Drejer, B. Barut, A. Zapata, T. C. Law, C. Brugnara, S. E. Lux, G. S. Pinkus, J. L. Pinkus, P. D. Kingsley, J. Palis, M. D. Fleming, N. C. Andrews, L. I. Zon, Positional cloning of zebrafish ferroportin1 identifies a conserved vertebrate iron exporter. *Nature* 403, 776-781 (2000).
4. A. Donovan, C. A. Lima, J. L. Pinkus, G. S. Pinkus, L. I. Zon, S. Robine, N. C. Andrews, The iron exporter ferroportin/Slc40a1 is essential for iron homeostasis. *Cell Metab* 1, 191-200 (2005).
5. S. Marro, D. Chiabrando, E. Messana, J. Stolte, E. Turco, E. Tolosano, M. U. Muckenthaler, Heme controls ferroportin1 (FPN1) transcription involving Bach1, Nrf2 and a MARE/ARE sequence motif at position-7007 of the FPN1 promoter. *Haematologica*.
6. D. L. Zhang, R. M. Hughes, H. Ollivierre-Wilson, M. C. Ghosh, T. A. Rouault, A ferroportin transcript that lacks an iron-responsive element enables duodenal and erythroid precursor cells to evade translational repression. *Cell Metab* 9, 461-473 (2009).
7. A. Lymboussaki, E. Pignatti, G. Montosi, C. Garuti, D. J. Haile, A. Pietrangelo, The role of the iron responsive element in the control of ferroportin1/IREG1/MTP1 gene expression. *J Hepatol* 39, 710-715 (2003).
8. E. Nemeth, M. S. Tuttle, J. Powelson, M. B. Vaughn, A. Donovan, D. M. Ward, T. Ganz, J. Kaplan, Hepcidin regulates cellular iron efflux by binding to ferroportin and inducing its internalization. *Science* 306, 2090-2093 2004).
9. I. De Domenico, E. Nemeth, J. M. Nelson, J. D. Phillips, R. S. Ajioka, M. S. Kay, J. P. Kushner, T. Ganz, D. M.

Ward, J. Kaplan, The hepcidin-binding site on ferroportin is evolutionarily conserved. *Cell Metab* 8, 146-156 (2008).
10. I. De Domenico, D. M. Ward, C. Langelier, M. B. Vaughn, E. Nemeth, W. I. Sundquist, T. Ganz, G. Musci, J. Kaplan, The molecular mechanism of hepcidinmediated ferroportin down-regulation. *Mol Biol Cell* 18, 2569-2578 (2007).
11. P. Holmstrom, M. Gafvels, L. C. Eriksson, V. Dzikaite, R. Hultcrantz, G. Eggertsen, P. Stal, Expression of iron regulatory genes in a rat model of hepatocellular carcinoma. *Liver Int* 26, 976-985 (2006).
12. J. Boult, K. Roberts, M. J. Brookes, S. Hughes, J. P. Bury, S. S. Cross, G. J. Anderson, R. Spychal, T. Iqbal, C. Tselepis, Overexpression of cellular iron import proteins is associated with malignant progression of esophageal adenocarcinoma. *Clin Cancer Res* 14, 379-387 (2008).
13. A. T. McKie, D. J. Barlow, The SLC40 basolateral iron transporter family (IREG1/ferroportin/MTP1). *Pflugers Arch* 447, 801-806 (2004).
14. B. Elenbaas, L. Spirio, F. Koerner, M. D. Fleming, D. B. Zimonjic, J. L. Donaher, N. C. Popescu, W. C. Hahn, R. A. Weinberg, Human breast cancer cells generated by oncogenic transformation of primary mammary epithelial cells. *Genes Dev* 15, 50-65 (2001).
15. H. D. Soule, T. M. Maloney, S. R. Wolman, W. D. Peterson, Jr., R. Brenz, C. M. McGrath, J. Russo, R. J. Pauley, R. F. Jones, S. C. Brooks, Isolation and characterization of a spontaneously immortalized human breast epithelial cell line, MCF-10. *Cancer Res* 50, 6075-6086 (1990).
16. S. C. Brooks, E. R. Locke, H. D. Soule, Estrogen receptor in a human cell line (MCF-7) from breast carcinoma. *J Biol Chem* 248, 6251-6253 (1973).
17. C. I. Sartor, M. L. Dziubinski, C. L. Yu, R. Jove, S. P. Ethier, Role of epidermal growth factor receptor and STAT-3 activation in autonomous proliferation of SUM-102PT human breast cancer cells. *Cancer Res* 57, 978-987 (1997).
18. K. M. Ignatoski, S. P. Ethier, Constitutive activation of pp125 fak in newly isolated human breast cancer cell lines. *Breast Cancer Res Treat* 54, 173-182 (1999).
19. O. Kakhlon, Z. I. Cabantchik, The labile iron pool: characterization, measurement, and participation in cellular processes(1). *Free Radic Biol Med* 33, 1037-1046 (2002).
20. T. Sorlie, C. M. Perou, R. Tibshirani, T. Aas, S. Geisler, H. Johnsen, T. Hastie, M. B. Eisen, M. van de Rijn, S. S. Jeffrey, T. Thorsen, H. Quist, J. C. Matese, P. O. Brown, D. Botstein, P. Eystein Lonning, A. L. Borresen-Dale, Gene expression patterns of breast carcinomas distinguish tumor subclasses with clinical implications. *Proc Natl Acad Sci USA* 98, 10869-10874 (2001).
21. P. Hall, A. Ploner, J. Bjohle, F. Huang, C. Y. Lin, E. T. Liu, L. D. Miller, H. Nordgren, Y. Pawitan, P. Shaw, L. Skoog, J. Smeds, S. Wedren, J. Ohd, J. Bergh, Hormone-replacement therapy influences gene expression profiles and is associated with breast-cancer prognosis: a cohort study. *BMC Med* 4, 16 (2006).
22. S. Calza, P. Hall, G. Auer, J. Bjohle, S. Klaar, U. Kronenwett, E. T. Liu, L. Miller, A. Ploner, J. Smeds, J. Bergh, Y. Pawitan, Intrinsic molecular signature of breast cancer in a population-based cohort of 412 patients. *Breast Cancer Res* 8, R34 (2006).
23. T. Sorlie, R. Tibshirani, J. Parker, T. Hastie, J. S. Marron, A. Nobel, S. Deng, H. Johnsen, R. Pesich, S. Geisler, J. Demeter, C. M. Perou, P. E. Lonning, P. O. Brown, A. L. Borresen-Dale, D. Botstein, Repeated observation of breast tumor subtypes in independent gene expression data sets. *Proc Natl Acad Sci USA* 100, 8418-8423 (2003).
24. M. J. van de Vijver, Y. D. He, L. J. van't Veer, H. Dai, A. A. Hart, D. W. Voskuil, G. J. Schreiber, J. L. Peterse, C. Roberts, M. J. Marton, M. Parrish, D. Atsma, A. Witteveen, A. Glas, L. Delahaye, T. van der Velde, H. Bartelink, S. Rodenhuis, E. T. Rutgers, S. H. Friend, R. Bernards, A gene-expression signature as a predictor of survival in breast cancer. *N Engl J Med* 347, 1999-2009 (2002).
25. L. D. Miller, J. Smeds, J. George, V. B. Vega, L. Vergara, A. Ploner, Y. Pawitan, P. Hall, S. Klaar, E. T. Liu, J. Bergh, An expression signature for p53 status in human breast cancer predicts mutation status, transcriptional effects, and patient survival. *Proc Natl Acad Sci USA* 102, 13550-13555 (2005).
26. P. L. Lee, E. Beutler, Regulation of hepcidin and iron-overload disease. *Annu Rev Pathol* 4, 489-515 (2009).
27. L. Thelander, A. Graslund, M. Thelander, Continual presence of oxygen and Iron required for mammalian ribonucleotide reduction: possible regulation mechanism. *Biochem Biophys Res Commun* 110, 859-865 (1983).
28. J. L. Buss, F. M. Torti, S. V. Torti, The role of iron chelation in cancer therapy. *Curr Med Chem* 10, 1021-1034 (2003).
29. G. Cairo, F. Bernuzzi, S. Recalcati, A precious metal: Iron, an essential nutrient for all cells. *Genes Nutr* 1, 25-39 (2006).
30. G. Chen, C. Fillebeen, J. Wang, K. Pantopoulos, Overexpression of iron regulatory protein 1 suppresses growth of tumor xenografts. *Carcinogenesis* 28, 785-791 (2007).
31. M. Whitnall, J. Howard, P. Ponka, D. R. Richardson, A class of iron chelators with a wide spectrum of potent antitumor activity that overcomes resistance to chemotherapeutics. *Proc Natl Acad Sci USA* 103, 14901-14906 (2006).
32. D. A. Green, W. E. Antholine, S. J. Wong, D. R. Richardson, C. R. Chitambar, Inhibition of malignant cell growth by 311, a novel iron chelator of the pyridoxal isonicotinoyl hydrazone class: effect on the R2 subunit of ribonucleotide reductase. *Clin Cancer Res* 7, 3574-3579 (2001).
33. J. E. Karp, F. J. Giles, I. Gojo, L. Morris, J. Greer, B. Johnson, M. Thein, M. Sznol, J. Low, A phase I study of the novel ribonucleotide reductase inhibitor 3-aminopyridine-2-carboxaldehyde thiosemicarbazone (3-AP, Triapine) in combination with the nucleoside analog fludarabine for patients with refractory acute leukemias and aggressive myeloproliferative disorders. *Leuk Res* 32, 71-77 (2008).
34. V. Rao, Klein, S., Agama, K., Toyoda, E., Adachi, N., Pommier, Y., Shacter, E., The iron chelator Dp44mT causes DNA damage and selective inhibition of topoisomerase-II alpha in breast cancer cells. *Cancer Research* 69(3):948-57 (2009).
35. W. P. Faulk, B. L. Hsi, P. J. Stevens, Transferrin and transferrin receptors in carcinoma of the breast. *Lancet* 2, 390-392 (1980).
36. T. R. Daniels, T. Delgado, G. Helguera, M. L. Penichet, The transferrin receptor part II: targeted delivery of therapeutic agents into cancer cells. *Clin Immunol* 121, 159-176 (2006).
37. T. R. Daniels, T. Delgado, J. A. Rodriguez, G. Helguera, M. L. Penichet, The transferrin receptor part I: Biology and targeting with cytotoxic antibodies for the treatment of cancer. *Clin Immunol* 121, 144-158 (2006).
38. K. J. Wu, A. Polack, R. Dalla-Favera, Coordinated regulation of iron-controlling genes, H-ferritin and IRP2, by c-MYC. *Science* 283, 676-679 (1999).
39. Y. Tsuji, E. Kwak, T. Saika, S. V. Torti, F. M. Torti, Preferential repression of the H subunit of ferritin by adenovirus E1A in NIH-3T3 mouse fibroblasts. *J Biol Chem* 268, 7270-7275 (1993).
40. O. Kakhlon, Y. Gruenbaum, Z. I. Cabantchik, Ferritin expression modulates cell cycle dynamics and cell responsiveness to H-ras-induced growth via expansion of the labile iron pool. *Biochem J* 363, 431-436 (2002).
41. W. I. Leong, B. Lonnerdal, Iron transporters in rat mammary gland: effects of different stages of lactation and maternal iron status. *Am J Clin Nutr* 81, 445-453 (2005).
42. F. M. Torti, S. V. Torti, Regulation of ferritin genes and protein. *Blood* 99, 3505-3516 (2002).
43. E. Nemeth, T. Ganz, Regulation of iron metabolism by hepcidin. *Annu Rev Nutr* 26, 323-342 (2006).
44. J. S. Parker, M. Mullins, M. C. Cheang, S. Leung, D. Voduc, T. Vickery, S. Davies, C. Fauron, X. He, Z. Hu, J. F. Quackenbush, I. J. Stijleman, J. Palazzo, J. S. Marron, A. B. Nobel, E. Mardis, T. O. Nielsen, M. J. Ellis, C. M. Perou, P. S. Bernard, Supervised risk predictor of breast cancer based on intrinsic subtypes. *J Clin Oncol* 27, 1160-1167 (2009).
45. S. Paik, S. Shak, G. Tang, C. Kim, J. Baker, M. Cronin, F. L. Baehner, M. G. Walker, D. Watson, T. Park, W. Hiller, E. R. Fisher, D. L. Wickerham, J. Bryant, N. Wolmark, A multigene assay to predict recurrence of tamoxifen-treated, nodenegative breast cancer. *N Engl J Med* 351, 2817-2826 (2004).
46. S. Chen, B. Zhu, L. Yu, In silico comparison of gene expression levels in ten human tumor types reveals candidate genes associated with carcinogenesis. *Cytogenet Genome Res* 112, 53-59 (2006).
47. D. T. Home, Scherf, U., Vockley, J. (U.S. Pat. No. 6,974,667 B2 Gene Logic, Inc., USA, 2005).
48. D. R. Rhodes, S. Kalyana-Sundaram, V. Mahavisno, R. Varambally, J. Yu, B. B. Briggs, T. R. Barrette, M. J. Anstet, C. Kincead-Beal, P. Kulkarni, S. Varambally, D. Ghosh, A. M. Chinnaiyan, Oncomine 3.0: genes, pathways, and networks in a collection of 18,000 cancer gene expression profiles. *Neoplasia* 9, 166-180 (2007).
49. E. C. Pietsch, J. Y. Chan, F. M. Torti, S. V. Torti, Nrf2 mediates the induction of ferritin H in response to xenobiotics and cancer chemopreventive dithiolethiones. *J Biol Chem* 278, 2361-2369 (2003).
50. J. L. Winter, B. L. Stackhouse, G. B. Russell, T. E. Kute, Measurement of PTEN expression using tissue microarrays to determine a race-specific prognostic marker in breast cancer. *Arch Pathol Lab Med* 131, 767-772 (2007).
51. Z. Deng, M. Wan, G. Sui, PIASy-mediated sumoylation of Yin Yang 1 depends on their interaction but not the RING finger. *Mol Cell Biol* 27, 3780-3792 (2007).
52. D. A. Rubinson, C. P. Dillon, A. V. Kwiatkowski, C. Sievers, L. Yang, J. Kopinja, D. L. Rooney, M. Zhang, M. M. Ihrig, M. T. McManus, F. B. Gertler, M. L. Scott, L. Van Parijs, A lentivirus-based system to functionally silence genes in primary mammalian cells, stem cells and transgenic mice by RNA interference. *Nat Genet* 33, 401-406 (2003).
53. A. V. Ivshina, J. George, O. Senko, B. Mow, T. C. Putti, J. Smeds, T. Lindahl, Y. Pawitan, P. Hall, H. Nordgren, J. E. Wong, E. T. Liu, J. Bergh, V. A. Kuznetsov, L. D. Miller, Genetic reclassification of histologic grade delineates new clinical subtypes of breast cancer. *Cancer Res* 66, 10292-10301 (2006).
54. J. Zhang, X. Liu, A. Datta, K. Govindarajan, W. L. Tam, J. Han, J. George, C. Wong, K. Ramnarayanan, T. Y. Phua, W. Y. Leong, Y. S. Chan, N. Palanisamy, E. T. Liu, K. M. Karuturi, B. Lim, L. D. Miller, RCP is a human breast cancerpromoting gene with Ras-activating function. *J Clin Invest* 119, 2171-2183(2009).
55. S. Loi, B. Haibe-Kains, C. Desmedt, F. Lallemand, A. M. Tutt, C. Gillet, P. Ellis, A. Harris, J. Bergh, J. A. Foekens, J. G. Klijn, D. Larsimont, M. Buyse, G. Bontempi, M. Delorenzi, M. J. Piccart, C. Sotiriou, Definition of clinically distinct molecular subtypes in estrogen receptor-positive breast carcinomas through genomic grade. *J Clin Oncol* 25, 1239-1246 (2007).

Example 2

Determination of and Clinical Relevance of IHA Markers in Iron Import/Export Dyads As described in detail in Example 1, ferroportin (ferroportin 1, also termed Ireg1, MTP1, SLC40A1) is a cell surface transmembrane protein and is the only known export protein for non-heme iron. Hepcidin (also referred to as HAMP) is a peptide hormone produced by the liver, and appears to be the master regulator of iron homeostasis in humans and other mammals. Hepcidin directly inhibits ferroportin, a protein that transports iron out of the cells that store it. Ferroportin is present on enterocytes and macrophages. By inhibiting ferroportin, hepcidin prevents enterocytes of the intestines from secreting iron into the hepatic portal system, thereby functionally reducing iron absorption. Iron release from macrophages is also prevented by ferroportin inhibition. Thus, hepcidin maintains iron homeostasis. Hepcidin activity is also partially responsible for iron sequestration seen in anemia of chronic disease. Ferroportin and Hepcidin comprise members of an iron export dyad. Our data show patients exhibiting high ferroportin expression levels in the presence of low hepcidin levels appear to be at a lowered risk of recurrent disesase.

The transferrin receptor, (also known as TFRC, p90, CD71) is a carrier protein for transferrin and is needed for the import of iron into the cell and is regulated in response to intracellular iron concentration. It imports iron by internalizing the transferrin-iron complex through receptor mediated endocytosis. Sequence information for the TfR is available in GenBank, Accession No. NM_003234.

The Hemochromatosis (HFE) gene is located on the short arm of chromosome 6. The protein encoded by this gene is a membrane protein that is similar toMHC class I-type proteins and associates with beta-2 microglobulin (beta2M). It is thought that this protein functions to regulate iron absorption by regulating the interaction of the transferrin receptor with transferrin. The iron storage disorder, hereditary hemochromatosis, (HHC) is an autosomal recessive genetic disorder that usually results from defects in this gene. Sequence information is available on GenBank Accession No. NM_000410.

TRC and HFE comprise members of an iron import dyad. Our data show that patient samples exhibiting high HFE levels in the presence of low TFRC levels are indicative of a lowered risk of recurrent disease. Thus, assessing the expression levels of the IHA markers which participate in the iron import andiron export dyads provide a powerful tool in predicting a patients risk for recurring breast cancer. See Example 4 herein below and FIG. 25 in particular.

In another two gene assessment, we found that a statistical model generated using the supervised principal component method of Bair and Tibshirani (PLoS (2004) 2(4):E108) revealed that CYBRD1 (also known as DcytB; GenBank Accession No. NM_024843) in combination with SCARA5 (GenBank Accession No. NM_173833) expression levels (a 2-gene model) provides a significant prognostic indicator for recurrent disease. Generally, the expression levels of both genes appears to be reduced in patients with increased risk for recurrence. This assessment, however, is based on a particular classification algorithm that constructs a statistical model (based on the expression levels of the genes and assigned weights), but could be reproduced with most any typical classification algorithm, including, without limitation a mathematical classification algorithm, diagonal linear discriminant analysis (DLDA), prediction analysis for microarrays (PAM), support vector machines (SVM), nearest shrunken centroids, K-nearest neighbors, and Bayesian compound covariate prediction. Any of these can be used to define a statistical model, based on the genes' expression characteristics, and thus used to predict a patient's risk of recurrent disease.

Example 3

Four and Six IHA Combination Models for Predicting Risk of Recurrent Disease

The prognostic power of the two gene model, however, is comparable to the results obtained when a similarly-derived statistical model based on expression levels of 4 IHA marker genes STEAP1+STEAP2+SFXN1+ISCU is employed. Thus, assessment of STEAP1+STEAP 2+ISCU+CYBRD1 expression levels in patient samples also provides a highly significant prognostic indicator for increased risk of recurrent cancer. In another approach, the expression levels of at least six genes are determined and these include CYBRD1, STEAP1, STEAP2, SCARA5, SFXN1 and ISCU. In one embodiment of the invention, expression levels of at least CYBRD1, and SCARA5, are determined as described above, however a further embodiment can include determination of STEAP1, STEAP2, SFXN1 and ISCU. In another approach, expression levels of at least TFRC+STEAP1+STEAP2+ISCU+CYBRD1+SLC40A1 can be utilized in a prognostic model to analyze recurrence risk. Alternatively, or in conjunction with the above determinations, expression levels of the combination of the genes TFRC+TMPRSS6+TF+FTH1+FTL+IREB2 can utilized in a prognostic model to predict recurrence risk of cancer to the patient.

Example 4

An IRGS for Predicting an Increased Risk for Recurrent Malignant Disease

As described in Example 1, we recently uncovered a role for a pathway that mediates iron efflux in breast cancer growth and metastasis (10). This pathway is mediated by ferroportin and hepcidin. Ferroportin is an iron efflux pump and hepcidin is a peptide hormone that binds to ferroportin and triggers its degradation (11). We observed that ferroportin expression is reduced in breast cancer cells relative to normal mammary epithelial cells. Low ferroportin expression correlated with high levels of metabolically available iron and increased growth of tumor xenografts. Strikingly, the expression of ferroportin in concert with the expression of hepcidin independently predicted for metastasis-free survival of women after definitive primary treatment of their breast cancer in multiple independent breast cancer cohorts (10).

Using formal bioinformatic analysis to assess the predictive value of all genes with readily identifiable roles in iron metabolism, we have identified an iron regulatory-gene signature (IRGS) that predicts outcome in breast cancer patients. Simple combinations of genes within this signature reveal different pathways of iron regulation that converge on a similar breast cancer phenotype.

Cases were divided into test and training cohorts and the supervised principal component method was used to stratify cases into risk groups. Optimal risk stratification was achieved with a model comprising the iron regulatory gene signature (IRGS). Multivariable analysis revealed that the IRGS contributes information not captured by conventional prognostic indicators (hazard ratio 1.61; 95% CI 1.16-2.24; p=0.004). The IRGS successfully stratified homogeneously treated patients, including ER+ patients treated with tamoxifen monotherapy, both with (p=0.006) and without (p=0.03) lymph node metastases.

To test whether multiple pathways were embedded within the IRGS, we evaluated the performance of two gene dyads with known roles in iron biology in ER+ patients treated with tamoxifen monotherapy (n=371). For both dyads, gene combinations that minimized intracellular iron content (anti-import: $TFRC^{Low}/HFE^{High}$; or pro-export: $FP^{High}/HAMP^{Low}$) were associated with favorable prognosis (p<0.005). The IRGS of the invention provides the clinician the ability to both identify high risk patients within traditionally low risk groups and low risk patients within high risk groups thereby guiding therapeutic decision-making.

Results

Genes that Regulate Iron Biology Exhibit Prognostic Associations in Breast Cancer To construct and confirm prognostic models based on iron associated genes, we randomized cases to two groups: a training and a test cohort, each comprising 337 cases. Next, we assembled a comprehensive list of genes with known functions in regulating iron biology. This list was derived from Gene Ontology (GO) categories related to iron metabolism (12, 13) and review of the literature; it comprised 63 genes and overlapped largely with the iron network disclosed by described in Hower et al. (14). Sixty-one of these genes (a subset of those provided in Table II) could be mapped to one or more corresponding microarray probe sets found on the Affymetrix U133A or U133B Genechips. Using the training cohort, we examined statistical associations between expression patterns of the iron regulatory genes and patient DMFS. Strikingly, we found that 49% of the genes were significantly associated with DMFS by Cox regression (p<0.05; likelihood ratio test) as measured by one or more probe sets (See Table VII). To determine the likelihood that such an observation would occur by chance alone, we analyzed the training cohort as well as the entire combined cohort by Fisher's exact test and permutation testing (Table VIII). Using two p-value thresholds for assigning significance to DMFS-associated genes (p<0.05 or p<0.01), we observed by Fisher's exact test a statistically significant enrichment for DMFS-associated genes among the 61 iron regulatory genes (as compared to the remaining population of genes represented on the microarray). This statistical significance was observed at both p-value thresholds and in both cohorts. Next, we performed permutation testing whereby in each cohort, we randomly selected a 61-gene set 100,000 times, and at each iteration, counted the number of DMFS-associated genes at each p-value threshold. In both cohorts, and at both thresholds, we again observed a statistically significant enrichment for DMFS-associated genes among the iron regulatory genes (p<0.02 in all cases). These data indicate that iron regulatory genes, as a group, are statistically unique in their tendency to be associated with DMFS, perhaps reflecting a pathologic role for iron regulation in the clinical behavior and progression of breast cancer.

TABLE VII

| Probe Set IDs | Symbol | Name | p-value^ | hazard ratio | 95% CI# |
|---|---|---|---|---|---|
| *222453_at; *217883_s_at | CYBRD1 | Cytochrome b reductase 1 | 3.53E−07 | 0.60 | 0.5-0.73 |
| *205642_at | STEAP1 | Six transmembrane epithelial antigen of the prostate 1 | 4.21E−05 | 0.59 | 0.47-0.74 |
| *225871_at | STEAP2 | Six transmembrane epithelial antigen of the prostate 2 | 2.02E−05 | 0.60 | 0.48-0.75 |
| *206087_x_at; 211888_x_at; 211330_s_at; 211327_x_at; 214547_s_at; 211329_x_at; 213864_x_at; 206296_x_at; 211253_x_at; 211325_x_at; 211328_x_at; 211331_x_at; 211332_x_at; 225764_at | HFE | Hemochromatosis | 3.05E−04 | 0.34 | 0.19-0.61 |
| *229839_at; *235949_at | SCARA5 | Scavenger receptor class A, member 5 (putative) | 4.02E−04 | 0.44 | 0.28-0.69 |
| *202018_s_at | LTF | Lactotransferrin | 4.18E−04 | 0.54 | 0.78-0.95 |
| *249628_x_at; 209621_at 237215_s_at; 207752_s_at | TFRC | Transferrin receptor (p90, CD71) | 6.16E−04 | 3.54 | 1.72-7.3 |
| *223044_at; *235123_at; | SLC40A1 | Solute carrier family 40 (iron-regulated transporter), member 1 (Feroportin) | 7.00E−04 | 0.76 | 0.64-0.89 |
| *209075_s_at | ISCU | Iron-sulfur cluster scaffold homolog | 7.74E−04 | 0.41 | 0.24-0.39 |
| *206392_x_at; 230658_at; 232565_at | SFXN1 | Sideroflexin 1 | 8.23E−04 | 2.02 | 1.34-3.96 |
| *209873_at; 200579_s_at; 241065_at | EPAS1 | Endothelial PAS domain protein 1 | 1.07E−03 | 0.57 | 0.41-8.8 |
| *225179_at; 222529_at; 251920_s_at; 222628_s_at; 242735_at; 225928_x_at; 228527_s_at; 218136_s_at; 281979_s_at | SLC25A37 | Solute carrier family 25, member 37 | 2.13E−03 | 0.55 | 0.37-0.80 |
| *209735_at | ABCG2 | ATP-binding cassette, sub family G (WHITE), member 2 | 3.52E−03 | 0.45 | 0.26-0.77 |
| *241999_at; 232591_at; 226379_at | SFXN5 | Sideroflexin 5 | 6.41E−03 | 4.00 | 1.51-10.5 |
| *225649_at; 213525_s_at; 59999_at | HIF1AN | Hypoxia inducible factor 1, alpha subunit inhibitor | 6.53E−03 | 0.51 | 0.32-0.83 |
| *218437_at; 218489_s_at | ALAD | Aminolevulinic dehydratase | 5.65E−03 | 0.49 | 0.29-0.34 |
| 230883_at; 205710_at | LRP2 | Low density lipoprotein-related protein 2 | 1.56E−02 | 0.85 | 0.74-0.97 |
| 213675_at; 221108_at | SLC22A17 | Solute carrier family 22, member 17 | 1.57E−02 | 0.83 | 0.43-0.91 |
| 228695_at; 203115_at; 203118_s_at | FECH | Ferrochelatase (protoporphyria) | 1.56E−02 | 0.33 | 0.14-0.92 |
| 208970_x_at; 208971_at; 222074_at | UROD | Uroporphyrinogen decarboxylase | 1.86E−02 | 0.46 | 0.25-0.87 |
| 222928_at | FLVCR1 | Feline leukemia virus subgroup C cellular receptor 1 | 1.75E−02 | 1.62 | 1.08-2.14 |
| 227158_at; 205323_s_at; 205322_s_at | MTF1 | Metal-regulatory transcription factor 1 | 2.50E−02 | 0.54 | 0.31-0.93 |
| 218121_at; 218120_s_at | HMOX2 | Heme oxygenase (decycling) 2 | 2.53E−02 | 2.63 | 1.11-5.25 |
| 209274_s_at; 221426_s_at; 209273_s_at | ISCA1 | Iron-sulfur cluster assembly 1 homolog | 3.25E−02 | 0.59 | 0.37-0.98 |
| 225987_at; 220197_at | STEAP4 | STEAP family member 4 | 3.63E−02 | 0.85 | 0.73-0.99 |
| 232941_at; 214965_at; 234367_x_at | TMPRSS6 | Transmembrane protease serine 6 | 3.63E−02 | 3.52 | 1.08-11.4 |
| 209054_s_at; 209005_at | FBXL5 | F-box and leucine-rich repeat protein 5 | 3.81E−02 | 0.52 | 0.4-0.97 |
| 215863_at; 267883_s_at; 210215_at | TFR2 | Transferrin receptor 2 | 3.92E−02 | 2.85 | 1.05-7.71 |
| 203536_s_at; 217501_at | CIAO1 | Cytosolic iron-sulfur protein assembly 1 homolog | 4.05E−02 | 1.85 | 1.03-3.32 |
| 220491_at | HAMP | Hepcidin antimicrobial peptide | 4.55E−03 | 1.85 | 1.01-2.68 |
| 200559_at | HIF1A | Hypoxia inducible factor 1, alpha subunit | 5.27E−02 | 1.40 | 1-1.97 |
| 223192_at; 221432_s_at | SLC25A28 | Solute carrier family 25, member 28 | 7.36E−02 | 0.50 | 0.23-1.07 |

Iron Regulatory-Gene Signatures are Predictive of Breast Cancer Recurrence

Using the supervised principal component method of Bair and Tibshirani (15), we investigated the prognostic potential of iron regulatory genes in statistical models predictive of breast cancer recurrence. The training cohort was used to generate, in total, 9 prognostic models representing different combinations of iron regulatory genes and model parameters. Specifically, we considered 3 threshold significance levels (α, alpha) for feature selection (α=0.01, α=0.001, or α=0.0001) and 1, 2 or 3 principal components, per significance level. The threshold significance levels refer to the statistical significance with which gene expression patterns (ie, Affymetrix probe set measurements) associate with DMFS of breast cancer patients. Thus, the threshold significance levels define univariate p-value cutoffs for selecting probe sets for model inclusion. At α=0.01, α=0.001, and α=0.0001, the number of genes selected for model inclusion after cross-validation were 16 genes (19 probe sets), 7 genes (8 probe sets) and 4 genes (5 probe sets), respectively. (Note that some genes are represented by more than one microarray probe set). Principal components refer to linear combinations of the iron regulatory genes that explain the variance-covariance structure underlying the gene expression patterns. The principle components determine the gene weight assignments in the classification model. All models were generated using doubly nested 10-fold cross-validation. Each model computes a prognostic index for each tumor sample, and this index reflects the relative likelihood of metastasis-free survival. During model construction, we specified 3 risk groups: low-risk, intermediate-risk and high-risk based on prognostic index cut points set at the 33$^{rd}$- and 66$^{th}$-percentiles of the training cohort. Upon generating a model, we then applied the model directly to the test cohort for independent verification of model performance.

In all training and testing scenarios, the prognostic models stratified cases into predicted risk groups with significantly different survival rates (p<0.005; log rank test; Table IX) indicating that the various different combinations of iron regulatory genes have robust prognostic potential regardless of model parameters. Maximal risk stratification in the training cohort, as determined by the hazard ratio of the predicted low and high risk groups, was achieved with the model comprising 16 genes (Model #2; α=0.01, 2 principle components). Confirming the results presented in Example 1, FIG. 22, Kaplan-Meier survival plots demonstrated a robust association between this collection of iron regulatory genes and distant metastasis-free survival.

TABLE VIII

Analysis for enrichment of DMFS-associated genes.

|  | Training Cohort (n = 337) | | Combined Cohort (n = 674) | |
| --- | --- | --- | --- | --- |
|  | P < 0.05 | P < 0.01 | P < 0.05 | P < 0.01 |
| # iron genes (of n = 61) significant: | 30 | 16 | 34 | 26 |
| # all genes (of n = 18,428) significant: | 5.718 | 3.012 | 7.778 | 4.963 |
| Fisher's Exact p-value*: | 0.003 | 0.03 | 0.02 | 0.006 |
| Permutation p-value^: | 0.0009 | 0.02 | 0.01 | 0.003 |

*two-tailed;
^100,000 iterations

TABLE IX

Cox proportional hazards analysis of the risk of distant metastasis in tamoxifen-treated patients*

| MODEL PARAMETERS | | | TRAINING SET RESULTS | | | TEST SET RESULTS | | |
| --- | --- | --- | --- | --- | --- | --- | --- | --- |
| Model # | α threshold* | PC$ | LRT^ p-value | Hazard Ratio | 95% CI& | LRT^ p-value | Hazard Ratio | 95% CI& |
| 1 | 0.01 | 1 | <0.0001 | 1.82 | 1.37-2.41 | 0.002 | 1.54 | 1.17-2.04 |
| 2 | 0.01 | 2 | <0.0001 | 2.18 | 1.62-2.94 | <0.0001 | 1.77 | 1.35-2.23 |
| 3 | 0.01 | 3 | <0.0001 | 2.22 | 1.65-3.00 | <0.0001 | 1.76 | 1.34-2.31 |
| 4 | 0.001 | 1 | 0.0004 | 1.65 | 1.24-2.18 | 0.001 | 1.58 | 1.19-2.08 |
| 5 | 0.001 | 2 | <0.0001 | 1.92 | 1.43-2.57 | <0.0001 | 1.76 | 1.34-2.30 |
| 6 | 0.001 | 3 | <0.0001 | 1.87 | 1.40-2.49 | 0.0002 | 1.67 | 1.27-2.19 |
| 7 | 0.0001 | 1 | <0.0001 | 2.17 | 1.61-2.92 | <0.0001 | 1.84 | 1.39-2.44 |
| 8 | 0.0001 | 2 | <0.0001 | 2.14 | 1.59-2.88 | <0.0001 | 1.81 | 1.37-2.39 |
| 9 | 0.0001 | 3 | 0.0003 | 1.71 | 1.27-2.32 | <0.0001 | 2.04 | 1.53-2.72 |

*significance threshold;
$number of principle components;
^likelihood ratio test;
&confidence interval To evaluate the potential clinical impact of this iron regulatory gene signature, hereafter referred to as the IRGS, we compared its prognostic attributes to those of conventional markers of breast cancer recurrence in a multivariable analysis involving the test cohort only (Table X). In the presence of nodal status, tumor size, patient age, histologic grade and ER status, the IRGS remained statistically significant (p=0.004) indicating that the IRGS contributes additive prognostic information not captured by these conventional markers.

TABLE X

Cox proportional hazards analysis of the risk of distant metastasis in the test cohort*

| | Univariate Analysis | | | Multivariable Analysis | | |
| --- | --- | --- | --- | --- | --- | --- |
| Covariates | Cox p-value# | Hazard Ratio | 95% CI | Cox p-value# | Hazard Ratio | 95% CI |
| IRGM (low-, mid-, high-risk) | <0.001 | 1.85 | 1.37-2.51 | 0.004 | 1.61 | 1.16-2.24 |
| ER status (0, 1) | 0.944 | 0.98 | 0.49-1.96 | 0.565 | 1.23 | 0.59-2.63 |
| LN status (0, 1) | 0.005 | 1.93 | 1.22-3.05 | 0.136 | 1.45 | 0.89-2.38 |
| Tumor size (cm; <2, 2-3, >3) | <0.001 | 1.91 | 1.37-2.66 | 0.018 | 1.57 | 1.08-2.28 |
| Patient Age (<35, 35-50, >50) | 0.906 | 1.03 | 0.61-1.73 | 0.918 | 0.97 | 0.57-1.67 |
| Histologic grade (1, 2, 3) | <0.001 | 1.75 | 1.26-2.43 | 0.244 | 1.26 | 0.85-1.86 |

*292 cases had complete clinical annotation for LN status, tumor size, patient age and histologic grade
^ CI denotes confidence interval;
Likelihood Ratio Test p-value The Iron Regulatory-Gene Signature (IRGS) is Prognostic of DMFS in Breast Tumor Subtypes and Treatment Groups To further understand the role of the IRGS in breast cancer, we evaluated its prognostic significance in specific molecular subtypes of breast cancer and patient treatment groups. Of note, we limited this analysis to subsets of the independent test cohort, in order to avoid overly optimistic interpretations that may result from inclusion of the training data.

First, we separately examined IRGS performance in the 295 cases positive for estrogen receptor (ER+) and the 40 cases lacking estrogen receptor (ER−). In the ER+ cases (FIG. 23A), the 3 risk groups significantly stratified patients by DMFS (p<0.001; log rank test). The significance of this stratification was largely driven by the particularly good outcome of the predicted low risk cases as compared to the intermediate and high risk groups, which showed similar, and comparably poorer, survival rates. In the smaller ER− population (FIG. 23B), the IRGS showed a consistent trend towards the correct classification of low, intermediate and high risk groups, but did not achieve statistical significance. Notably, however, we observed that the prognostic index assigned by the IRGS to the ER− cases, as a continuous variable, was in fact statistically significantly associated with DMFS by Cox regression analysis (p=0.035; likelihood ratio test) indicating that alternate IRGS cut points may be necessary for assigning risk to ER− cases.

We next examined the prognostic relevance of the IRGS in the intrinsic breast cancer subtypes [16, 17]. First we examined the basal subtype, which tends to comprise ER− tumors with poor outcomes (16-18). Consistent with this poor outcome association, the majority of cases (67%) were assigned by the IRGS to the predicted high risk group (FIG. 23C). Similar to that observed of the ER− population, the IRGS showed a substantial but non-significant risk stratification of the basal cases. The continuous prognostic index, however, did not reach significance by Cox regression (p=0.1).

Next, we considered the subtypes that largely comprise ER+ breast cancer, namely, the luminal A (LumA), luminal B (LumB) and Normal-like (NL) subtypes. Consistent with previous observations that LumA and NL subtypes exhibit more favorable survival outcomes (18), the IRGS classified the majority of LumA (54%; FIG. 23D) and NL subtypes (55%, FIG. 23E) into the low risk group. However, within the LumA subtype, the IRGS predicted intermediate and high risk cases that showed significantly poorer survival (p=0.03; log rank test), indicating that the IRGS can further risk stratify LumA disease. In a similar fashion, the IRGS further risk-stratified the NL subtype (p=0.01; log rank test) predicting a small fraction of high risk cases (4%) that showed an increased rate of distant metastasis. The LumB subtype has been historically associated with poor survival outcomes, and concordantly in our patient population the majority of LumB cases were classified by the IRGS as high risk (69%; FIG. 23F). An additional subtype, the HER2+-like subtype, has also been described; however, too few cases were present (n=24) to assess performance of the IRGS. However, we did note that all but one of the HER2+-like cases were classified by the IRGS as high or intermediate risk, consistent with previous observations that this subtype is associated with poor outcome (data not shown). Taken together, these observations suggest that the IRGS, while recapitulating some of the prognostic features of the molecular subtypes, may provide valuable additive prognostic information to the LumA and NL subtypes, and potentially ER− negative breast cancer.

As the potential variable effects of different treatments were not accounted for in the previous analyses, we examined the prognostic attributes of the IRGS in uniformly treated patients. First, we considered the subset of 104 patients (in the test cohort) who, following surgery, received no adjuvant systemic therapy (FIG. 24A). The IRGS risk groups stratified these patients with statistical significance (p=0.05; log rank test), indicating that the IRGS has, to some extent, a purely prognostic component uncoupled from adjuvant therapy prediction. The largest, most uniformly treated patient subgroup in the test cohort comprised ER+ patients (negative or positive for lymph node (LN) involvement) treated in the adjuvant setting with tamoxifen monotherapy (n=185). Determining treatment for these patients is a particular clinical challenge as the desire to treat these patients aggressively with combination tamoxifen and adjuvant chemotherapy is counterbalanced by the small gain in therapeutic benefit imparted by added chemotherapy and the severity of the adverse side effects caused by chemotherapy. We evaluated the IRGS in two subsets of this treatment group: the ER+, LN− subset (n=99) and the ER+, LN+ subset (n=86). As shown in FIGS. 24B and 24C, the IRGS predicted for a low risk group that exhibits significantly better DMFS than the predicted intermediate and high risk groups, and this observation is consistent in both the LN− and LN+ populations. As the intermediate and high risk groups showed no differences in actual DMFS rates, we considered the relevance of the IRGS as a binary classifier (ie, 0=low risk and 1=high risk/intermediate risk) in a multivariable analysis of the tamoxifen-treated population. While all 5 covariates (IRGS, LN status, tumor size, patient age and histologic grade) were significantly associated with DMFS by univariate analysis, only the IRGS and tumor size remained significant in the multivariable model (p=0.007 and p=0.035, respectively) (Table XI). Together, these observations demonstrate that the IRGS contributes important clinical value in predicting subsets of ER+ patients (even those with LN+ disease) that will show excellent long-term distant metastasis-free survival if they are treated with tamoxifen and spared adjuvant chemotherapy.

TABLE XI

Cox proportional hazards analysis of the risk of distant metastasis in tamoxifen-treated patients*

| Covariates | Univariate Analysis | | | Multivariable Analysis | | |
|---|---|---|---|---|---|---|
| | Cox p-value# | Hazard Ratio | 95% CI | Cox p-value# | Hazard Radio | 95% CI |
| IRGM (low-, high-risk) | <0.001 | 5.69 | 2.029-15.99 | 0.007 | 4.32 | 1.49-12.51 |
| LN status (0, 1) | 0.043 | 1.91 | 1.01-3.63 | 0.183 | 1.58 | 0.81-3.08 |
| Tumor size (cm; <2, 2-3, >3) | <0.001 | 2.29 | 1.46-3.58 | 0.035 | 1.69 | 1.04-2.76 |

TABLE XI-continued

Cox proportional hazards analysis of the risk of distant metastasis in tamoxifen-treated patients*

| Covariates | Univariate Analysis | | | Multivariable Analysis | | |
|---|---|---|---|---|---|---|
| | Cox p-value[#] | Hazard Ratio | 95% CI | Cox p-value[#] | Hazard Radio | 95% CI |
| Patient Age (<35, 35-50, >50) | 0.049 | 4.63 | 0.64-33.67 | 0.343 | 2.64 | 0.36-19.68 |
| Histologic grade (1, 2, 3) | 0.007 | 1.87 | 1.18-2.98 | 0.288 | 1.33 | 0.79-2.24 |

*157 cases had complete clinical annotation for LN status, tumor size, patient age and histologic grade
^ CI denotes confidence interval;
[#]Likelihood Ratio Test p-value Iron Export and Iron Import Gene Dyads are Complementing Prognostic Factors in Breast Cancer To better understand the transcriptional dynamics of the prognostic IRGS genes, we investigated their correlation structure in the combined breast cancer cohort by hierarchical clustering. Surprisingly, we found that the transcriptional patterns of the IRGS genes are largely diverse, displaying an average Pearson correlation of −0.1. This suggests that the IRGS genes may represent multiple regulatory pathways, each of which affects iron homeostasis in an independent way.

To test this hypothesis, we examined the effect of transferrin receptor 1 (TFRC) and hereditary hemochromatosis (HFE) on prognosis. The rationale for this approach was derived from our previous observation that expression of ferroportin and hepcidin, two genes whose products work together to regulate iron export, affect prognosis in breast cancer (10). Specifically, we had previously found that high levels of the iron efflux pump ferroportin (Fp), which leads to low levels of intracellular iron, were associated with favorable prognosis. In patients who expressed high levels of Fp, concomitant expression of low levels of hepcidin (HAMP), a protein that degrades ferroportin, further improved prognosis. Since these results suggest that decreased intracellular iron is associated with a favorable prognosis, we reasoned that other genes that decrease intracellular iron might similarly affect prognosis. We therefore tested whether TFRC and HFE, two gene products that work together to regulate iron import, might represent a complementary regulatory pathway embedded in the IRGS gene set. Cellular uptake of iron is predominantly driven by endocytosis of iron-loaded transferrin bound to TFRC. The HFE protein negatively regulates TFRC-mediated iron uptake (19-21). Thus, whereas TFRC acts to promote iron import, HFE acts to block it, through mechanisms that are still under investigation (22).

To study the prognostic interplay between TFRC and HFE, as well as their associations with Fp and HAMP, we studied the expression-survival associations of these genes in the full combined cohort with a focus on the ER+ patients uniformly treated with tamoxifen monotherapy (n=371). All tumors were assigned the binary annotation of "low" or "high" expression for a given gene based on whether the signal intensity fell below or above the population mean. A Pro-Export phenotype was assigned to tumors having high Fp and low HAMP concomitantly, while an Anti-Export phenotype was assigned to those having both low Fp and high HAMP. In a similar vein, a Pro-Import phenotype was assigned to tumors showing both high TFRC levels and low HFE levels, while an Anti Import phenotype was assigned to those having concomitant low TFRC and high HFE. Shown in FIG. 25 are distant metastasis-free survival estimates of breast cancer cases categorized according to iron export (FIG. 25A) and iron import (FIG. 25B) phenotypes. Consistent with the hypothesis that cellular iron content is a determinant of breast cancer behavior, both Pro-Export and Anti-Import phenotypes predicted for reduced metastasis rates, while Anti-Export and Pro-Import phenotypes predicted for significantly increased metastasis rates. Next, to investigate the prognostic relationship between the iron export and import phenotypes, each dyad was compared in a multivariable model for its prognostic contributions (Table XII). Both dyads remained highly significant in the multivariable model (p<0.005) indicating that they each contribute additively (in a non-colinear fashion) to the prediction of metastatic recurrence. Indeed, while both Pro-Export and Anti-Import phenotypes predicted for low metastatic risk, they largely comprised different patients (FIG. 25C), suggesting these phenotypes represent independent pathways to a final common endpoint. Together, these data present the possibility that different regulatory modulators of cellular iron content may directly, and through distinct mechanisms, impact the clinical progression of breast cancer.

TABLE VII

Multivariable model with iron gene dyads in tamoxifen-treated patients*

| Covariates | Cox p-value[#] | Hazard Ratio | 95% CI |
|---|---|---|---|
| Fp/HAMP Dyad (0, 1, 2) | 0.001 | 1.63 | 1.21-2.20 |
| TFRC/HFE Dyad (0, 1, 2) | 0.004 | 1.56 | 1.16-2.11 |

*371 cases,
^CI denotes confidence interval
[#]Likelihood Ratio Test p-value

Discussion

Datasets of tumor expression profiles represent a rich resource for hypothesis testing and may provide insights into novel biological properties of human tumors. Previous work has successfully used such datasets to identify groups of functionally unrelated genes that collectively associate with breast cancer risk (16, 17). In this work we used a different strategy, capitalizing on publicly available microarray datasets derived from breast cancer patient cohorts to test the hypothesis that perturbations of iron metabolism affect breast cancer risk. Specifically, we tested (1) whether expression of genes related to iron metabolism are collectively linked to breast cancer prognosis; (2) whether an optimal iron regulatory gene signature (IRGS) could be identified; (3) whether specific pathways involving different aspects of iron management could be identified within this signature; (4) whether this signature exhibited potential clinical utility.

We observed a statistically significant association between almost 50% of 61 genes involved in iron metabolism and breast cancer prognosis, indicating a remarkably robust association between expression of genes related to iron metabolism and breast cancer prognosis (Table VII). Maximal stratification into low, intermediate and high risk groups was achieved with an iron regulatory gene signature (IRGS) comprising 16 of these genes, which therefore represents one optimal signature. The IRGS (underlined markers in the Tables) does not appear to simply recapitulate information provided in other molecular classifiers of breast cancer, and provides additional useful information to discriminate among patients. For example, we found that the IRGS could further stratify LumA and normal-like tumors (FIG. 23D,E) into high, intermediate, and low risk groups. Similarly, multivariable analysis revealed that the IRGS contributed information in addition to that provided by the conventional markers of nodal status, tumor size, patient age, histologic grade or ER status.

The IRGS also contains embedded information about molecular pathways of iron metabolism that can be used to probe pathways that are perturbed in cancer. Our previous results identified ferroportin and hepcidin as two genes important in one such pathway (10). The products of these genes can be considered an iron efflux dyad: ferroportin is an iron efflux pump whose stability is controlled by hepcidin. We observed that a "low intracellular iron" phenotype conferred by high ferroportin and low hepcidin was associated with good prognosis, whereas a "high intracellular iron" phenotype conferred by low ferroportin and high hepcidin was associated with poorer prognosis (10).

We assessed whether pathways that mediate iron import might represent a second pathway that similarly modifies prognosis. We selected TFRC, the major iron importer in most mammalian cells, and HFE, a protein that negatively regulates TFRC-mediated iron uptake, to represent an iron import dyad. In agreement with results obtained with the iron export dyad of ferroportin and hepcidin, a "low intracellular iron" phenotype was associated with good prognosis, and a "high intracellular iron" phenotype was associated with poorer prognosis (FIG. 25). Thus high levels of TFRC in conjunction with low levels of its negative modulator HFE were associated with poorer DMFS than low levels of TFRC and high levels of HFE. These results are consistent with the literature: an increase in levels of the TFRC protein in breast and other cancers has been known since the 80's (23), as well as the dependency of cancer cell proliferation on TFRC-mediated iron uptake (24-26). In fact, the transferrin receptor is frequently used as a targeting ligand in the design of anti-cancer drugs (27). Overall, our results are concordant with and begin to provide molecular specificity to the historical view of iron as an element that favors both malignant transformation and tumor growth (28).

The data presented herein are useful for future hypothesis generation and testing. Not all gene associations that we observed conform to a simple picture in which increased iron content is associated with poorer prognosis: we found that expression of some genes whose products have been ascribed functions related to iron import (e.g CYBRD1) were associated with improved rather than decreased survival. Interestingly, the association of CYBRD1 with good prognosis is supported by a recent study that sought to identify genes that distinguish primary breast tumors and their matched nodal metastases but did not look at outcome. Such findings may suggest that products of these "iron" genes exhibit multiple functions, or that they play alternative roles in breast tissue when compared to tissues involved in systemic iron management (e.g. the duodenum, liver, etc), where the roles of many of these genes have been elucidated.

Some gene associations we observed confirm expectations based on the literature. For example, we found that HIF1 alpha, which is frequently a negative prognostic indicator (30), was associated with reduced DMFS (Table VII). Conversely, increased expression of the HIF1 alpha inhibitor (HIF1AN), was associated with improved DMFS.

Assessing the expression of the 16 genes comprising the IRGS in breast cancer patients may have clinical utility. We observed that the IRGS could be successfully used to predict the outcome of ER+ patients (FIG. 23A) and patients exhibiting favorable molecular subtypes (LumA and normal-like (FIG. 23D,E). While the IRGS showed only a near-significant trend towards risk stratification in ER– patients by Kaplan Meier analysis (FIG. 23B), Cox regression showed a significant association with DMFS when the IRGS prognostic index was used as a continuous variable. This suggests that future study of the IRGS in risk stratification of ER– patients will require a rescaling of the survival group assignments as they pertain to the IRGS prognostic index. When we divided patients into groups that had received homogeneous treatment, the IRGS was able to stratify all patients, including those who had received no treatment and those treated with tamoxifen monotherapy, independent of lymph node status (FIG. 24). These results suggest that the IRGS may be useful in two different clinical settings. First, it may allow identification of potentially high risk patients within the traditional low risk LumA and NL subtypes, which comprise a sizable fraction of luminal breast cancer cases. Second, it may spare patients unneeded chemotherapy by allowing the identification of subsets of ER+ patients (even those with LN+ disease) who will show excellent distant metastasis-free survival when treated with tamoxifen monotherapy. That the IRGS significantly risk-stratified LumA cases, suggests that an integrated prognostic model combining aspects of the IRGS and luminal subtypes (or the subtype-derived Risk of Relapse (ROR) score) (31), (32) could provide additive prognostic power to outcome prediction.

Overall, this study demonstrates a strong link between genes that govern iron metabolism and breast cancer, and suggests new tools to guide breast cancer prognosis. Over the longer term, it may also help uncover metabolic differences that distinguish normal and malignant breast cancer cells that can be used to therapeutic advantage.

DATAFILE 3

The prognostic index for the IRGS can be computed by the formula $\Sigma_i w_i x_i + 7.952256$ where $w_i$ and $x_i$ are the weight (w) and logged ($\log_2$) RMA-normalized signal intensity (x) for the i-th gene. A new sample is then predicted as high risk if its prognostic index is larger than 0.265029, medium risk if the index is within $-0.361502$ and $0.265029$, and low risk if the index is smaller than or equal to $-0.361502$.

GENE WEIGHTS

| Probe Set ID | Loading 1 | Loading2 | Correlation 1 | Correlation2 | Weights ($w_i$) |
|---|---|---|---|---|---|
| 222453_at | 0.005156 | 0.015134 | 0.616886 | 0.586163 | −0.154325 |
| 205542_at | 0.003811 | 0.006251 | 0.493097 | 0.261814 | −0.081303 |
| 217889_s_at | 0.005424 | 0.016119 | 0.564745 | 0.543249 | −0.163662 |
| 225871_at | 0.004202 | 0.009891 | 0.561049 | 0.427456 | −0.109552 |
| 229839_at | 0.00141 | 0.001745 | 0.279576 | 0.112051 | −0.026307 |
| 202018_s_at | 0.017398 | −0.018644 | 0.943308 | −0.327212 | −0.057846 |
| 240686_x_at | −0.00044 | −0.000852 | −0.195116 | −0.122441 | 0.010251 |
| 223044_at | 0.003973 | 0.015385 | 0.415288 | 0.52055 | −0.143637 |
| 200878_at | 0.001707 | 0.003192 | 0.341259 | 0.206601 | −0.03901 |
| 235849_at | 0.000618 | 0.000307 | 0.179952 | 0.028983 | −0.008491 |
| 209075_s_at | 0.000663 | 0.002555 | 0.230579 | 0.287793 | −0.023881 |
| 241999_at | −0.000223 | −0.000862 | −0.137044 | −0.171298 | 0.008051 |
| 218392_x_at | −0.001114 | 0.000291 | −0.333757 | 0.028255 | 0.009694 |
| 226179_at | 0.002114 | −0.002531 | 0.479971 | −0.186042 | −0.005261 |
| 209735_at | 0.000897 | 0.002074 | 0.254366 | 0.190356 | −0.023135 |
| 233123_at | 0.002508 | 0.0077 | 0.376859 | 0.374555 | −0.077314 |
| 206087_x_at | 0.000725 | 0.000859 | 0.236663 | 0.09077 | −0.013276 |
| 226648_at | 0.000684 | 0.003583 | 0.201255 | 0.341361 | −0.030929 |
| 218487_at | 0.001281 | 0.002722 | 0.405185 | 0.278621 | −0.031452 |

REFERENCES FOR EXAMPLES 2-4

1. Torti S V, Torti F M. Ironing out cancer. Cancer Res 2011; 71(5):1511-4.
2. Stevens R G, Jones D Y, Micozzi M S, Taylor P R. Body iron stores and the risk of cancer. The New England journal of medicine 1988; 319(16):1047-52.
3. Stevens R G, Graubard B I, Micozzi M S, Neriishi K, Blumberg B S. Moderate elevation of body iron level and increased risk of cancer occurrence and death. International journal of cancer 1994; 56(3):364-9.
4. Siegers C P, Bumann D, Baretton G, Younes M. Dietary iron enhances the tumor rate in dimethylhydrazine-induced colon carcinogenesis in mice. Cancer Lett 1988; 41(3):251-6.
5. Smith A G, Francis J E, Carthew P. Iron as a synergist for hepatocellular carcinoma induced by polychlorinated biphenyls in Ah-responsive C57BL/10ScSn mice. Carcinogenesis 1990; 11(3):437-44.
6. Hann H W, Stahlhut M W, Blumberg B S. Iron nutrition and tumor growth: decreased tumor growth in iron-deficient mice. Cancer Res 1988; 48(15):4168-70.
7. Hann H W, Stahlhut M W, Menduke H. Iron enhances tumor growth. Observation on spontaneous mammary tumors in mice. Cancer 1991; 68(11):2407-10.
8. Kovacevic Z, Kalinowski D S, Lovejoy D B, Quach P, Wong J, Richardson D R. Iron Chelators: Development of Novel Compounds with High and Selective Anti-Tumour Activity. Curr Drug Deliv.
9. Buss J L, Greene B T, Turner J, Torti F M, Torti S V. Iron chelators in cancer chemotherapy. Curr Top Med Chem 2004; 4(15):1623-35.
10. Pinnix Z K, Miller L D, Wang W, et al. Ferroportin and iron regulation in breast cancer progression and prognosis. Sci Transl Med 2010; 2(43):43-56.
11. Nemeth E, Tuttle M S, Powelson J, et al. Hepcidin regulates cellular iron efflux by binding to ferroportin and inducing its internalization. Science 2004; 306(5704): 2090-3.
12. Ashburner M, Ball C A, Blake J A, et al. Gene ontology: tool for the unification of biology. The Gene Ontology Consortium. Nat Genet 2000; 25(1):25-9.
13. Recalcati S, Locati M, Marini A, et al. Differential regulation of iron homeostasis during human macrophage polarized activation. Eur J Immunol 2009; 40(3):824-35.
14. Hower V, Mendes P, Torti F M, et al. A general map of iron metabolism and tissue-specific subnetworks. Mol Biosyst 2009; 5(5):422-43.
15. Bair E, Tibshirani R. Semi-supervised methods to predict patient survival from gene expression data. PLoS Biol 2004; 2(4):E108.
16. Sorlie T, Perou C M, Tibshirani R, et al. Gene expression patterns of breast carcinomas distinguish tumor subclasses with clinical implications. Proceedings of the National Academy of Sciences of the United States of America 2001; 98(19):10869-74.
17. Sorlie T, Tibshirani R, Parker J, et al. Repeated observation of breast tumor subtypes in independent gene expression data sets. Proceedings of the National Academy of Sciences of the United States of America 2003; 100(14):8418-23.
18. Hu Z, Fan C, Oh D S, et al. The molecular portraits of breast tumors are conserved across microarray platforms. BMC Genomics 2006; 7:96.
19. Feder J N, Penny D M, Irrinki A, et al. The hemochromatosis gene product complexes with the transferrin receptor and lowers its affinity for ligand binding. Proceedings of the National Academy of Sciences of the United States of America 1998; 95(4):1472-7.
20. Zhang A S, Davies P S, Carlson H L, Enns C A. Mechanisms of HFE-induced regulation of iron homeostasis: Insights from the W81A HFE mutation. Proceedings of the National Academy of Sciences of the United States of America 2003; 100(16):9500-5.
21. Roy C N, Penny D M, Feder J N, Enns C A. The hereditary hemochromatosis protein, HFE, specifically regulates transferrin-mediated iron uptake in HeLa cells. The Journal of biological chemistry 1999; 274(13):9022-8.
22. Schmidt P J, Toran P T, Giannetti A M, Bjorkman P J, Andrews N C. The transferrin receptor modulates Hfe-dependent regulation of hepcidin expression. Cell metabolism 2008; 7(3):205-14.
23. Faulk W P, Hsi B L, Stevens P J. Transferrin and transferrin receptors in carcinoma of the breast. 1980; 2(8191):390-2.
24. Forsbeck K, Bjelkenkrantz K, Nilsson K. Role of iron in the proliferation of the established human tumor cell lines U-937 and K-562: effects of suramin and a lipophilic iron chelator (PIH). Scandinavian journal of haematology 1986; 37(5):429-37.

25. Forsbeck K, Nilsson K. The dynamic morphology of the transferrin-transferrin receptor system in human leukaemia/lymphoma cell lines and its relation to iron metabolism and cell proliferation. Scandinavian journal of haematology 1985; 35(2):145-54.
26. Vostrejs M, Moran P L, Seligman P A. Transferrin synthesis by small cell lung cancer cells acts as an autocrine regulator of cellular proliferation. The Journal of clinical investigation 1988; 82(1):331-9.
27. Shan L, Hao Y, Wang S, et al. Visualizing head and neck tumors in vivo using near-infrared fluorescent transferrin conjugate. Mol Imaging 2008; 7(1):42-9.
28. Weinberg E D. The role of iron in cancer. Eur J Cancer Prev 1996; 5(1):19-36.
29. Vecchi M, Confalonieri S, Nuciforo P, et al. Breast cancer metastases are molecularly distinct from their primary tumors. Oncogene 2008; 27(15):2148-58.
30. Lundgren K, Holm C, Landberg G. Hypoxia and breast cancer: prognostic and therapeutic implications. Cell Mol Life Sci 2007; 64(24):3233-47.
31. Parker J S, Mullins M, Cheang M C, et al. Supervised risk predictor of breast cancer based on intrinsic subtypes. J Clin Oncol 2009; 27(8):1160-7.
32. Nielsen T O, Parker J S, Leung S, et al. A comparison of PAM50 intrinsic subtyping with immunohistochemistry and clinical prognostic factors in tamoxifen-treated estrogen receptor-positive breast cancer. Clin Cancer Res; 16(21):5222-32.
33. Irizarry R A, Bolstad B M, Collin F, Cope L M, Hobbs B, Speed T P. Summaries of Affymetrix GeneChip probe level data. Nucleic Acids Res 2003; 31(4):e15.
34. Fan C, Oh D S, Wessels L, et al. Concordance among gene-expression-based predictors for breast cancer. N Engl J Med 2006; 355(6):560-9.

Example 5

Prognostic IHA Markers for Prostate Cancer

The ability to identify prostate cancer patients who will relapse is perhaps the most compelling clinical question in prostate cancer, or at least the one that will have the most direct and immediate application to patients. Although Gleason grade and PSA can identify the likelihood of progression for groups of patients, these measurements do not function with sufficient precision on individual patients to guide individual treatment decisions. This is particularly true for prostate cancer patients diagnosed with intermediate Gleason grades and PSA levels, where the probability of relapse remains sufficiently high that most patients opt for definitive radiation treatment or prostatectomy. Nonetheless, it is generally acknowledged that a proportion of these patients might not require treatment due to the indolence of their cancers. A biomarker that could identify prostate cancers with a low risk of relapse would spare patients substantial morbidity associated with treatment.

As described in the previous examples, genetic analysis of IHA marker gene expression levels in target tumor tissues provides the clinician with a significant prognostic indicator for assessing risk of recurrent disease. Accordingly, analyzing prostate cancer tissue for expression levels of the various IHA markers set forth in Tables I, II, III and IV is also encompassed within the present invention. Thus, analyzing expression levels in the iron import and iron export dyads, as well as assessing expression levels of the IRGS should provide an indication of a patients risk for metastatic cancer. Indeed, any of the subcombinations of markers listed in Table IV would be appropriate for this purpose.

Our analysis of publicly available datasets (ref 6,7) indicates that ferroportin expression is down-regulated in prostate cancer compared to controls (FIG. 26A). We also observed that ferroportin expression is reduced in prostate metastases compared to the primary tumor (FIG. 26B). In additional experiments, prostate cancer specimens were sectioned and stained with a commercial FP antibody and evaluated by a clinical pathologist. The marked reduction of FP in prostate cancers was evident (FIG. 27). Arrows point to examples of brown FP staining in normal prostate (left panel). No discernible staining was seen in the prostate cancer (right panel), consistent with decreased FPN protein in prostate cancer.

The ferroportin gene is methylated in prostate cancer compared to normal prostate: using Wake Forest Cancer Genomics dataset of genome-wide methylation profiles comparing 19 prostate cancer samples to four normal prostate tissue samples, we determined that the ferroportin gene is hypermethylated in prostate cancer compared to normal prostate tissue, providing one possible mechanistic explanation for the decreased expression in prostate cancer.

The work presented in Examples 1-4 in breast and ovarian cancer is also directly relevant: we showed that among lymph node positive breast cancer patients, there was a subset of high ferroportin expressing tumors that had nearly a 90% 5 year survival [1]. Such women probably should not be exposed to extensive treatments. These same analytic techniques will be applied to prostate tumors. In aggregate, our data (See FIG. 5) suggest that ferroportin expression is reduced in prostate cancer compared to normal prostate, and that expression correlates with prostate cancer grade and metastases.

REFERENCES FOR EXAMPLE 5

1 Pinnix, Z. K., Miller, L. D., Wang, W., D'Agostino, R., Jr., Kute, T., Willingham, M. C., Hatcher, H., Tesfay, L., Sui, G., Di, X., Torti, S. V. and Torti, F. M. (2010) Ferroportin and iron regulation in breast cancer progression and prognosis. Sci Transl Med. 2, 43ra56
2 Gorlov, I. P., Sircar, K., Zhao, H., Maity, S. N., Navone, N. M., Gorlova, O. Y., Troncoso, P., Pettaway, C. A., Byun, J. Y. and Logothetis, C. J. (2010) Prioritizing genes associated with prostate cancer development. BMC Cancer. 10, 599
3 Luo, J. H., Yu, Y. P., Cieply, K., Lin, F., Deflavia, P., Dhir, R., Finkelstein, S., Michalopoulos, G. and Becich, M. (2002) Gene expression analysis of prostate cancers. Mol Carcinog. 33, 25-35
4 Singh, D., Febbo, P. G., Ross, K., Jackson, D. G., Manola, J., Ladd, C., Tamayo, P., Renshaw, A. A., D'Amico, A. V., Richie, J. P., Lander, E. S., Loda, M., Kantoff, P. W., Golub, T. R. and Sellers, W. R. (2002) Gene expression correlates of clinical prostate cancer behavior. Cancer Cell. 1, 203-209
5 Welsh, J. B., Sapinoso, L. M., Su, A. I., Kern, S. G., Wang-Rodriguez, J., Moskaluk, C. A., Frierson, H. F., Jr. and Hampton, G. M. (2001) Analysis of gene expression identifies candidate markers and pharmacological targets in prostate cancer. Cancer Res. 61, 5974-5978
6 Tomlins, S. A., Mehra, R., Rhodes, D. R., Cao, X., Wang, L., Dhanasekaran, S. M., Kalyana-Sundaram, S., Wei, J. T., Rubin, M. A., Pienta, K. J., Shah, R. B. and Chinnaiyan, A. M. (2007) Integrative molecular concept modeling of prostate cancer progression. Nat Genet. 39, 41-51

7 Varambally, S., Yu, J., Laxman, B., Rhodes, D. R., Mehra, R., Tomlins, S. A., Shah, R. B., Chandran, U., Monzon, F. A., Becich, M. J., Wei, J. T., Pienta, K. J., Ghosh, D., Rubin, M. A. and Chinnaiyan, A. M. (2005) Integrative genomic and proteomic analysis of prostate cancer reveals signatures of metastatic progression. Cancer Cell. 8, 393-406

8 Torti, S. V. and Torti, F. M. (2011) Ironing out cancer. Cancer Res. 71, 1511-1514

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A method for detecting protein biomarkers for breast cancer in a patient, said method comprising;
   a) obtaining a biological sample from a human patient; and
   b) detecting whether iron homeostasis protein biomarkers consisting of hepcidin, ferroportin, hemochromatosis gene (HFE), transferrin receptor (TFRC), cytochrome B reductase (CYBRD1), scavenger receptor class A, member 5 (SCARA5), ferritin light polypeptide (FTL), iron response element binding protein 2 (IREB2), transferrin (TF), transmembrane protease, serine 6 (TMPRSS6), ferritin, heavy polypeptide (FTH1), six transmembrane epithelial antigen of the prostate 1 (STEAP1), six transmembrane epithelial antigen of the prostate 2 (STEAP2), iron-sulfur cluster scaffold homolog (ISCU), and sideroflexin 1 (SFXN1) are present in said sample by contacting said sample with detectably labeled anti-biomarker antibodies or immunologically specific fragments thereof and detecting formation of specific binding pairs between said breast cancer biomarkers and said antibodies or immunologically specific fragments thereof.

2. A method for detecting nucleic acid biomarkers for breast cancer in a patient, said method comprising;
   a) obtaining a biological sample from a human patient; and
   b) detecting whether iron homeostasis biomarker encoding nucleic acids consisting of hepcidin, ferroportin, hemochromatosis gene (HFE), transferrin receptor (TFRC), cytochrome B reductase (CYBRD1), scavenger receptor class A, member 5 (SCARA5), ferritin light polypeptide (FTL), iron response element binding protein 2 (IREB2), transferrin (TF), transmembrane protease, serine 6 (TMPRSS6), ferritin, heavy polypeptide (FTH1), six transmembrane epithelial antigen of the prostate 1 (STEAP1), six transmembrane epithelial antigen of the prostate 2 (STEAP2), iron-sulfur cluster scaffold homolog (ISCU), and sideroflexin 1 (SFXN1) are present in said sample by contacting said sample with detectably labeled nucleic acid probes or primers which form specific binding complexes with or amplify said nucleic acids encoding said iron homeostasis biomarkers.

3. A kit for detecting biomarkers for breast cancer in a patient consisting of
   a) labeled antibodies immunologically specific for iron homeostasis protein biomarkers consisting of hepcidin, ferroportin, hemochromatosis gene (HFE), transferrin receptor (TFRC), cytochrome B reductase (CYBRD1), scavenger receptor class A, member 5 (SCARA5), ferritin light polypeptide (FTL), iron response element binding protein 2 (IREB2), transferrin (TF), transmembrane protease, serine 6 (TMPRSS6), ferritin, heavy polypeptide (FTH1), six transmembrane epithelial antigen of the prostate 1 (STEAP1), six transmembrane epithelial antigen of the prostate 2 (STEAP2), iron-sulfur cluster scaffold homolog (ISCU), and sideroflexin 1 (SFXN1) for detecting expression levels of said iron homeostasis protein biomarkers in a sample obtained from said patient, wherein said labeled antibodies form specific binding pairs with said iron homeostasis protein biomarkers, and wherein said labeled antibodies are suitable for flow cytometric analysis, immunohistochemical detection, or immunoblot analysis, and/or labeled nucleic acids which specifically hybridize to iron homeostasis biomarkers encoding nucleic acids consisting of hepcidin, ferroportin, hemochromatosis gene (HFE), transferrin receptor (TFRC), cytochrome B reductase (CYBRD1), scavenger receptor class A, member 5 (SCARA5), ferritin light polypeptide (FTL), iron response element binding protein 2 (IREB2), transferrin (TF), transmembrane protease, serine 6 (TMPRSS6), ferritin, heavy polypeptide (FTH1), six transmembrane epithelial antigen of the prostate 1 (STEAP1), six transmembrane epithelial antigen of the prostate 2 (STEAP2), iron-sulfur cluster scaffold homolog (ISCU), and sideroflexin 1 (SFXN1) for detecting expression levels of said iron homeostasis biomarkers in a sample obtained from said patient, wherein said labeled nucleic acids form specific binding complexes with or amplify said iron homeostasis biomarkers encoding nucleic acids, and wherein said labeled nucleic acids are suitable for performance of in situ hybridization assay, hybridization assay, gel electrophoresis, RT-PCR, real time PCR, or microarray analysis,
   b) instructional materials comprising ranges of iron homeostasis biomarker expression levels associated with aggressive metastatic breast cancer and ranges of expression levels associated with non-aggressive non-metastatic breast cancer, and
   c) immunospecific labeled antibodies or specifically hybridizing labeled nucleic acids for detecting one or more of estrogen receptor (ER), her2-neu, and progesterone receptor.

4. The method of claim 1, wherein ratios of at least two markers selected from the group consisting of ferroportin/hepcidin, HFE/TFRC, CYBRD1/TFRC and CYBRD1/SCARA5 are determined.

5. The method of claim 1 wherein detection levels of Ferroportin, CYBRD1, STEAP1, STEAP2, ISCU and TFRC protein levels in said sample are provided in a report.

6. A method for detecting biomarkers associated with long-term survival of a prostate cancer patient without the recurrence of cancer, consisting of:
   a) obtaining a biological sample for a patient;
   b) detecting in said sample iron homeostasis markers consisting of ferroportin, hepcidin, hemochromatosis gene (HFE), transferrin receptor (TFRC), cytochrome B reductase (CYBRD1) and scavenger receptor class A, member 5 (SCARA5), ferritin light polypeptide (FTL), iron response element binding protein 2 (IREB2), transferrin (TF), transmembrane protease, serine 6 (TMPRSS6) and ferritin, heavy polypeptide (FTH1) six transmembrane epithelial antigen of the prostate 1 (STEAP1), six transmembrane epithelial antigen of the prostate 2 (STEAP2), iron-sulfur cluster scaffold homolog (ISCU), sideroflexin 1 (SFXN1), solute carrier family 25, member 37 (SLC25A37), amyloid beta (A4) precursor protein (APP), hypoxia inducible factor 1, alpha subunit inhibitor (HIFIAN), aminolevulinate dehydratase (ALAD), low density lipoprotein receptor-related protein 2 (LRP2), solute carrier family 22, member 17 (SLC22A17), ferrochelatase (FECH), uroporpyrinogen decarboxylase (UROD), feline leukemia virus subgroup C cellular receptor 1 (FLVCR1), glutaredoxin 5, metal-regulatory transcription factor 1 (MTF1), heme oxygenase 2 (HMOX2), iron-sulfur cluster assembly 1 homolog (ISCA1), STEAP family member 4), F-box and leucine rich repeat protein 5 (FBXL5), transferrin receptor 2 (TFR2), cytosolic iron sulfur protein assembly 1 (CIAO1), bone morphogenic protein 6 (BMP6), solute carrier family 11, member 1 (SLC11A1), hypoxia inducible factor 1 (HIF1A), and solute carrier family 46 (SLC46A1) in said sample, by contacting said sample with detectably labeled antibodies or fragments thereof immunologically specific for iron homeostasis protein biomarkers and/or detectably labeled nucleic acid primers or probes which hybridize with iron homeostasis encoding nucleic acids, and detecting formation of specific binding pairs between said proteins and antibodies and/or specific binding pairs between said probes or primers and said iron homeostasis encoding nucleic acids.

7. The method of claim 6, wherein said labeled antibody or fragment thereof is suitable for detection of protein biomarkers via a method selected from the group consisting of flow cytometric analysis, immunohisto-chemical detection and immunoblot analysis.

8. The method of claim 6, wherein said detectably labeled probe or primer which specifically hybridizes to said nucleic acid biomarker is suitable for performing a method selected from the group consisting of in situ hybridization assay, hybridization assay, gel electrophoresis, RT-PCR, real time PCR, and microarray analysis.

\* \* \* \* \*

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
acctcgctgg tggtacagaa tgtt                                              24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
agcaggaagt gagaacccat ccat                                              24

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gaaggtgaag gtcggagtc                                                    19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gaagatggtg atgggatttc                                                   20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
aggctttgcc tttccaactt cagc                                              24

<210> SEQ ID NO 6
<211> LENGTH: 24
<212> TYPE: DNA
<213> ORGANISM: Artificial Sequence
```

```
<220> FEATURE:
<223> OTHER INFORMATION: Primer

<400> SEQUENCE: 6
aacaggagtg caaggaactg gaga                                              24

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gtgtggcatc tggttggagt ttca                                              24

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
aacaggagtg caaggaactg gaga                                              24

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ctttgtcctg gtgagcacat ctga                                              24

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
atcctctctg gcggttgtga tct                                               23

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
ctgcaacccc aggacagag                                                    19

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggaataaata aggaagggag ggg                                               23
```